United States Patent
Wilcke et al.

(10) Patent No.: US 10,745,398 B2
(45) Date of Patent: Aug. 18, 2020

(54) 2-(HET)ARYL-SUBSTITUTED FUSED HETEROCYCLE DERIVATIVES AS PESTICIDES

(71) Applicant: Bayer CropScience Aktiengesellschaft, Monheim am Rhein (DE)

(72) Inventors: David Wilcke, Düsseldorf (DE); Rüdiger Fischer, Pulheim (DE); Dominik Hager, Monheim (DE); Nina Kausch-Busies, Bergisch Gladbach (DE); Laura Hoffmeister, Düsseldorf (DE); Kerstin Ilg, Köln (DE); Ulrich Görgens, Ratingen (DE); Daniela Portz, Vettweiß (DE); Andreas Turberg, Haan (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 115 days.

(21) Appl. No.: 15/763,168

(22) PCT Filed: Sep. 23, 2016

(86) PCT No.: PCT/EP2016/072697
§ 371 (c)(1),
(2) Date: Mar. 26, 2018

(87) PCT Pub. No.: WO2017/055185
PCT Pub. Date: Apr. 6, 2017

(65) Prior Publication Data
US 2018/0303097 A1 Oct. 25, 2018

(30) Foreign Application Priority Data
Sep. 28, 2015 (EP) .................................... 15187145

(51) Int. Cl.
C07D 471/04 (2006.01)
A01N 43/653 (2006.01)
A01N 43/90 (2006.01)
C07D 401/14 (2006.01)

(52) U.S. Cl.
CPC ......... *C07D 471/04* (2013.01); *A01N 43/653* (2013.01); *A01N 43/90* (2013.01); *C07D 401/14* (2013.01)

(58) Field of Classification Search
CPC .. C07D 471/04; C07D 498/04; C07D 401/14; C07D 403/14; A01N 43/90; A01N 43/653
See application file for complete search history.

(56) References Cited

U.S. PATENT DOCUMENTS

2012/0328569 A1* 12/2012 McComas ............ A61K 31/343
424/85.7

FOREIGN PATENT DOCUMENTS

| WO | 2010/125985 A1 | 11/2010 |
|----|----------------|---------|
| WO | 2012/074135 A1 | 6/2012 |
| WO | 2012/086848 A1 | 6/2012 |
| WO | 2013/018928 A1 | 2/2013 |
| WO | 2013/191113 A1 | 12/2013 |
| WO | 2014/142292 A1 | 9/2014 |
| WO | 2014/148451 A1 | 9/2014 |
| WO | 2015/000715 A1 | 1/2015 |
| WO | 2015/002211 A1 | 1/2015 |
| WO | 2015/071180 A1 | 5/2015 |
| WO | 2015/091945 A1 | 6/2015 |
| WO | 2015/121136 A1 | 8/2015 |
| WO | 2015/133603 A1 | 9/2015 |
| WO | 2015/198817 A1 | 12/2015 |
| WO | 2015/198859 A1 | 12/2015 |
| WO | 2016/005263 A1 | 1/2016 |
| WO | 2016/020286 A1 | 2/2016 |
| WO | 2016/023954 A2 | 2/2016 |
| WO | 2016/026848 A1 | 2/2016 |
| WO | 2016/039441 A1 | 3/2016 |
| WO | 2016/041819 A1 | 3/2016 |
| WO | 2016/046071 A1 | 3/2016 |
| WO | 2016/124563 A1 | 8/2016 |
| WO | 2016/124577 A1 | 8/2016 |

OTHER PUBLICATIONS

International Search Report of International Patent Application No. PCT/EP2016/072697 dated Dec. 6, 2016.

* cited by examiner

*Primary Examiner* — John Pak
(74) *Attorney, Agent, or Firm* — McBee Moore & Vanik IP, LLC

(57) ABSTRACT

The invention relates to novel compounds of the formula (I)

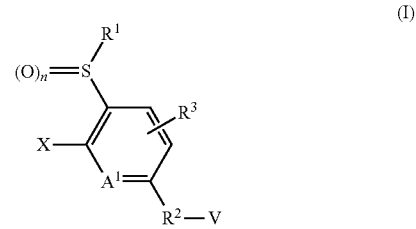

in which $R^1$, $R^2$, $R^3$, $A^1$, V, X and n have the meanings given above, to their use as acaricides and/or insecticides for controlling animal pests and to processes and intermediates for their preparation.

13 Claims, No Drawings

2-(HET)ARYL-SUBSTITUTED FUSED HETEROCYCLE DERIVATIVES AS PESTICIDES

CROSS REFERENCE TO RELATED APPLICATIONS

This application is a National Stage entry of International Application No. PCT/EP2016/072697 filed 23 Sep. 2016, which claims priority to European Patent Application No. 15187145.6, filed 28 Sep. 2015.

BACKGROUND

Field of the Invention

The present invention relates to novel 2-(het)aryl-substituted fused heterocycle derivatives of the formula (I), to the use thereof as acaricides and/or insecticides for controlling animal pests, particularly arthropods and especially insects and arachnids, and to processes and intermediates for preparation thereof.

Description of Related Art

Fused heterocycle derivatives with insecticidal properties are already described in the literature, e.g. in WO 2010/125985, WO 2012/074135, WO 2012/086848, WO 2013/018928, WO 2013/191113, WO 2014/142292, WO 2014/148451, WO 2015/000715, EP 15153943.4, EP 15153948.3, WO 2015/121136, WO 2015/133603, WO 2015/198859, WO 2015/002211, WO 2015/071180, WO 2015/091945, WO 2016/005263, WO 2015/198817, WO 2016/041819, WO 2016/039441, WO 2016/026848, WO 2016/023954, WO 2016/020286 and WO 2016/046071.

However, the active compounds already known according to the documents cited above have some disadvantages on application, whether because they exhibit only a narrow range of application or because they do not have satisfactory insecticidal or acaricidal activity.

SUMMARY

Novel 2-(het)aryl-substituted fused heterocycle derivatives have now been found, and these have advantages over the compounds already known, examples of which are better biological or environmental properties, a wider range of application methods, better insecticidal or acaricidal activity, and also good compatibility with crop plants. The 2-(het)aryl-substituted fused heterocycle derivatives can be used in combination with further agents for improving efficacy, especially against insects that are difficult to control.

The present invention therefore provides novel compounds of the formula (I)

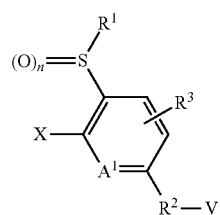

(I)

in which (configuration 1)
$A^1$ represents nitrogen, $=N^+(O^-)-$ or $=C(R^4)-$,
$R^1$ represents $(C_1-C_6)$-alkyl, $(C_1-C_6)$haloalkyl, $(C_1-C_6)$cyanoalkyl, $(C_1-C_6)$hydroxyalkyl, $(C_1-C_6)$alkoxy-$(C_1-C_6)$alkyl, $(C_1-C_6)$haloalkoxy-$(C_1-C_6)$alkyl, $(C_2-C_6)$alkenyl, $(C_2-C_6)$alkenyloxy-$(C_1-C_6)$alkyl, $(C_2-C_6)$haloalkenyloxy-$(C_1-C_6)$alkyl, $(C_2-C_6)$haloalkenyl, $(C_2-C_6)$cyanoalkenyl, $(C_2-C_6)$alkynyl, $(C_2-C_6)$alkynyloxy-$(C_1-C_6)$alkyl, $(C_2-C_6)$haloalkynyloxy-$(C_1-C_6)$alkyl, $(C_2-C_6)$haloalkynyl, $(C_2-C_6)$cyanoalkynyl, $(C_3-C_8)$cycloalkyl, $(C_3-C_8)$cycloalkyl-$(C_3-C_8)$cycloalkyl, $(C_1-C_6)$alkyl-$(C_3-C_8)$cycloalkyl, halo$(C_3-C_8)$cycloalkyl, amino, $(C_1-C_6)$alkylamino, di-$(C_1-C_6)$alkylamino, $(C_3-C_8)$cycloalkylamino, $(C_1-C_6)$alkylcarbonylamino, $(C_1-C_6)$alkylthio-$(C_1-C_6)$alkyl, $(C_1-C_6)$haloalkylthio-$(C_1-C_6)$alkyl, $(C_1-C_6)$alkylsulphinyl-$(C_1-C_6)$alkyl, $(C_1-C_6)$haloalkylsulphinyl-$(C_1-C_6)$alkyl, $(C_1-C_6)$alkylsulphonyl-$(C_1-C_6)$alkyl, $(C_1-C_6)$haloalkylsulphonyl-$(C_1-C_6)$alkyl, $(C_1-C_6)$alkoxy-$(C_1-C_6)$alkylthio-$(C_1-C_6)$alkyl, $(C_1-C_6)$alkoxy-$(C_1-C_6)$alkylsulphinyl-$(C_1-C_6)$alkyl, $(C_1-C_6)$alkoxy-$(C_1-C_6)$alkylsulphonyl-$(C_1-C_6)$alkyl, $(C_1-C_6)$alkylcarbonyl-$(C_1-C_6)$alkyl, $(C_1-C_6)$haloalkylcarbonyl-$(C_1-C_6)$alkyl, $(C_1-C_6)$alkoxycarbonyl-$(C_1-C_6)$alkyl, $(C_1-C_6)$haloalkoxycarbonyl-$(C_1-C_6)$alkyl, $(C_1-C_6)$alkylsulphonylamino, aminosulphonyl-$(C_1-C_6)$alkyl, $(C_1-C_6)$alkylaminosulphonyl-$(C_1-C_6)$alkyl, di-$(C_1-C_6)$alkylaminosulphonyl-$(C_1-C_6)$alkyl, or represents the following groups in each case optionally mono- or polysubstituted by identical or different aryl, hetaryl- or heterocyclyl substituents: $(C_1-C_6)$alkyl, $(C_1-C_6)$alkoxy, $(C_2-C_6)$alkenyl, $(C_2-C_6)$alkynyl, $(C_3-C_8)$cycloalkyl, where aryl, hetaryl or heterocyclyl can be in each case optionally mono- or polysubstituted by the following identical or different substituents: halogen, cyano, nitro, hydroxy, amino, carboxy, carbamoyl, aminosulphonyl, $(C_1-C_6)$alkyl, $(C_3-C_6)$cycloalkyl, $(C_1-C_6)$alkoxy, $(C_1-C_6)$haloalkyl, $(C_1-C_6)$haloalkoxy, $(C_1-C_6)$alkylthio, $(C_1-C_6)$alkylsulphinyl, $(C_1-C_6)$alkylsulphonyl, $(C_1-C_6)$alkylsulphimino, $(C_1-C_6)$alkylsulphimino-$(C_1-C_6)$alkyl, $(C_1-C_6)$alkylsulphimino-$(C_2-C_6)$alkylcarbonyl, $(C_1-C_6)$alkylsulphoximino, $(C_1-C_6)$alkylsulphoximino-$(C_1-C_6)$alkyl, $(C_1-C_6)$alkylsulphoximino-$(C_2-C_6)$alkylcarbonyl, $(C_1-C_6)$alkoxycarbonyl, $(C_1-C_6)$alkylcarbonyl, $(C_3-C_6)$trialkylsilyl or benzyl or $R^1$ represents aryl, hetaryl or heterocyclyl, each of which is optionally mono- or polysubstituted by identical or different substituents from the group consisting of halogen, cyano, nitro, hydroxy, amino, carboxy, carbamoyl, $(C_1-C_6)$alkyl, $(C_3-C_8)$cycloalkyl, $(C_1-C_6)$-alkoxy, $(C_1-C_6)$haloalkyl, $(C_1-C_6)$haloalkoxy, $(C_1-C_6)$alkylthio, $(C_1-C_6)$alkylsulphinyl, $(C_1-C_6)$alkylsulphonyl, $(C_1-C_6)$alkylsulphimino, $(C_1-C_6)$alkylsulphimino-$(C_1-C_6)$alkyl, $(C_1-C_6)$alkylsulphimino-$(C_2-C_6)$alkylcarbonyl, $(C_1-C_6)$alkylsulphoximino, $(C_1-C_6)$alkylsulphoximino-$(C_1-C_6)$alkyl, $(C_1-C_6)$alkylsulphoximino-$(C_2-C_6)$alkylcarbonyl, $(C_1-C_6)$alkoxycarbonyl, $(C_1-C_6)$alkylcarbonyl, $(C_3-C_6)$trialkylsilyl, $(=O)$ (only in the case of heterocyclyl) and $(=O)_2$ (only in the case of heterocyclyl), $R^2$ represents a saturated, partially saturated or heteroaromatic ring which is optionally mono- or polysubstituted by identical or different substituents, and in which at least one carbon atom is replaced by a heteroatom, where in each case optionally at least one carbonyl group may be present and/or where possible substituents are in each case as follows: cyano, carboxyl, halogen, nitro, acetyl, hydroxy, amino, SCN, tri-$(C_1-C_6)$alkylsilyl, $(C_1-C_6)$alkyl, ($C_1$-$C_6$)haloalkyl, ($C_1$-$C_6$)cyanoalkyl, ($C_1$-$C_6$)hydroxyalkyl, hydroxycarbonyl-($C_1$-$C_6$)-alkoxy, ($C_1$-$C_6$)alkoxycarbonyl-($C_1$-$C_6$)alkyl, ($C_1$-$C_6$)alkoxy-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)haloalkynyl, ($C_2$-$C_6$)cyanoalkynyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl ($C_1$-$C_6$)alkoxy, ($C_1$-$C_6$)haloalkoxy, ($C_1$-$C_6$)cyanoalkoxy, ($C_1$-$C_6$)alkoxycarbonyl-($C_1$-$C_6$)alkoxy, ($C_1$-$C_6$)alkoxy-($C_1$-$C_6$)alkoxy, ($C_1$-$C_6$)alkoxyimino, —N=C(H)—O($C_1$-$C_6$)alkyl, —C(H)=N—O($C_1$-$C_6$)alkyl, ($C_1$-$C_6$)haloalkyl-($C_1$-$C_6$)alkoxyimino, ($C_1$-$C_6$)alkylthio, ($C_1$-$C_6$)haloalkylthio, ($C_1$-$C_6$)alkoxy-($C_1$-$C_6$)alkylthio, ($C_1$-$C_6$)alkylthio-($C_1$-$C_6$)alkyl, ($C_1$-$C_6$)alkylsulphinyl, ($C_1$-$C_6$)haloalkylsulphinyl, ($C_1$-$C_6$)alkoxy-($C_1$-$C_6$)alkylsulphinyl, ($C_1$-$C_6$)alkylsulphinyl-($C_1$-$C_6$)alkyl, ($C_1$-$C_6$)alkylsulphonyl, ($C_1$-$C_6$)haloalkylsulphonyl, ($C_1$-$C_6$)alkoxy-($C_1$-$C_6$)alkylsulphonyl, ($C_1$-$C_6$)alkylsulphonyl-($C_1$-$C_6$)alkyl, ($C_1$-$C_6$)alkylsulphonyloxy, ($C_1$-$C_6$)alkylcarbonyl, ($C_1$-$C_6$)haloalkylcarbonyl, ($C_1$-$C_6$)alkylcarbonyloxy, ($C_1$-$C_6$)alkoxycarbonyl, ($C_1$-$C_6$)haloalkoxycarbonyl, aminocarbonyl, ($C_1$-$C_6$)alkylaminocarbonyl, di-($C_1$-$C_6$)alkylaminocarbonyl, ($C_2$-$C_6$)alkenylaminocarbonyl, di-($C_2$-$C_6$)-alkenylaminocarbonyl, ($C_3$-$C_8$)cycloalkylaminocarbonyl, ($C_1$-$C_6$)alkylsulphonylamino, ($C_1$-$C_6$)alkylamino, di-($C_1$-$C_6$)alkylamino, aminosulphonyl, ($C_1$-$C_6$)alkylaminosulphonyl, di-($C_1$-$C_6$)alkylaminosulphonyl, ($C_1$-$C_6$)alkylsulphoximino, aminothiocarbonyl, ($C_1$-$C_6$)alkylaminothiocarbonyl, di-($C_1$-$C_6$)alkylaminothiocarbonyl, ($C_3$-$C_8$)cycloalkylamino, ($C_1$-$C_6$)alkylcarbonylamino, V represents a saturated, partially saturated or heteroaromatic ring which is optionally mono- or polysubstituted by identical or different substituents, and in which at least one carbon atom is replaced by a heteroatom, or represents an aromatic ring mono- or polysubstituted by identical or different substituents, where in each case optionally at least one carbonyl group may be present and/or where possible substituents are in each case as follows: cyano, carboxyl, halogen, nitro, acetyl, hydroxy, amino, SCN, tri-($C_1$-$C_6$)alkylsilyl, ($C_1$-$C_6$)alkyl, ($C_1$-$C_6$)haloalkyl, ($C_1$-$C_6$)cyanoalkyl, ($C_1$-$C_6$)hydroxyalkyl, hydroxycarbonyl-($C_1$-$C_6$)-alkoxy, ($C_1$-$C_6$)alkoxycarbonyl-($C_1$-$C_6$)alkyl, ($C_1$-$C_6$)alkoxy-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)haloalkynyl, ($C_2$-$C_6$)cyanoalkynyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl ($C_1$-$C_6$)alkoxy, ($C_1$-$C_6$)haloalkoxy, ($C_1$-$C_6$)cyanoalkoxy, ($C_1$-$C_6$)alkoxycarbonyl-($C_1$-$C_6$)alkoxy, ($C_1$-$C_6$)alkoxy-($C_1$-$C_6$)alkoxy, ($C_1$-$C_6$)alkoxyimino, —N=C(H)—O($C_1$-$C_6$)alkyl, —C(H)=N—O($C_1$-$C_6$)alkyl, ($C_1$-$C_6$)haloalkyl-($C_1$-$C_6$)alkoxyimino, ($C_1$-$C_6$)alkylthio, ($C_1$-$C_6$)haloalkylthio, ($C_1$-$C_6$)alkoxy-($C_1$-$C_6$)alkylthio, ($C_1$-$C_6$)alkylthio-($C_1$-$C_6$)alkyl, ($C_1$-$C_6$)alkylsulphinyl, ($C_1$-$C_6$)haloalkylsulphinyl, ($C_1$-$C_6$)alkoxy-($C_1$-$C_6$)alkylsulphinyl, ($C_1$-$C_6$)alkylsulphinyl-($C_1$-$C_6$)alkyl, ($C_1$-$C_6$)alkylsulphonyl, ($C_1$-$C_6$)haloalkylsulphonyl, ($C_1$-$C_6$)alkoxy-($C_1$-$C_6$)alkylsulphonyl, ($C_1$-$C_6$)alkylsulphonyl-($C_1$-$C_6$)alkyl, ($C_1$-$C_6$)alkylsulphonyloxy, ($C_1$-$C_6$)alkylcarbonyl, ($C_1$-$C_6$)haloalkylcarbonyl, ($C_1$-$C_6$)alkylcarbonyloxy, ($C_1$-$C_6$)alkoxycarbonyl, ($C_1$-$C_6$)haloalkoxycarbonyl, aminocarbonyl, ($C_1$-$C_6$)alkylaminocarbonyl, di-($C_1$-$C_6$)alkylaminocarbonyl, ($C_2$-$C_6$)alkenylaminocarbonyl, di-($C_2$-$C_6$)-alkenylaminocarbonyl, ($C_3$-$C_8$)cycloalkylaminocarbonyl, ($C_1$-$C_6$)alkylsulphonylamino, ($C_1$-$C_6$)alkylamino, di-($C_1$-$C_6$)alkylamino, aminosulphonyl, ($C_1$-$C_6$)alkylaminosulphonyl, di-($C_1$-$C_6$)alkylaminosulphonyl, ($C_1$-$C_6$)alkylsulphoximino, aminothiocarbonyl, ($C_1$-$C_6$)alkylaminothiocarbonyl, di-($C_1$-$C_6$)alkylaminothiocarbonyl, ($C_3$-$C_8$)cycloalkylamino, ($C_1$-$C_6$)alkylcarbonylamino, $R^3$ represents hydrogen, cyano, halogen, nitro, acetyl, hydroxy, amino, SCN, tri-($C_1$-$C_6$)alkylsilyl, ($C_3$-$C_8$)cycloalkyl, ($C_3$-$C_8$)cycloalkyl-($C_3$-$C_8$)cycloalkyl, ($C_1$-$C_6$)alkyl-($C_3$-$C_8$)cycloalkyl, halo($C_3$-$C_8$)cycloalkyl, ($C_1$-$C_6$)alkyl, ($C_1$-$C_6$)haloalkyl, ($C_1$-$C_6$)cyanoalkyl, ($C_1$-$C_6$)hydroxyalkyl, hydroxycarbonyl-($C_1$-$C_6$)-alkoxy, ($C_1$-$C_6$)alkoxycarbonyl-($C_1$-$C_6$)alkyl, ($C_1$-$C_6$)alkoxy-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)haloalkynyl, ($C_2$-$C_6$)cyanoalkynyl, ($C_1$-$C_6$)alkoxy, ($C_1$-$C_6$)haloalkoxy, ($C_1$-$C_6$)cyanoalkoxy, ($C_1$-$C_6$)alkoxycarbonyl-($C_1$-$C_6$)alkoxy, ($C_1$-$C_6$)alkoxy-($C_1$-$C_6$)alkoxy, ($C_1$-$C_6$)alkylhydroxyimino, ($C_1$-$C_6$)alkoxyimino, ($C_1$-$C_6$)alkyl-($C_1$-$C_6$)alkoxyimino, ($C_1$-$C_6$)haloalkyl-($C_1$-$C_6$)alkoxyimino, ($C_1$-$C_6$)alkylthio, ($C_1$-$C_6$)haloalkylthio, ($C_1$-$C_6$)alkoxy-($C_1$-$C_6$)alkylthio, ($C_1$-$C_6$)alkylthio-($C_1$-$C_6$)alkyl, ($C_1$-$C_6$)alkylsulphinyl, ($C_1$-$C_6$)haloalkylsulphinyl, ($C_1$-$C_6$)alkoxy-($C_1$-$C_6$)alkylsulphinyl, ($C_1$-$C_6$)alkylsulphinyl-($C_1$-$C_6$)alkyl, ($C_1$-$C_6$)alkylsulphonyl, ($C_1$-$C_6$)haloalkylsulphonyl, ($C_1$-$C_6$)alkoxy-($C_1$-$C_6$)alkylsulphonyl, ($C_1$-$C_6$)alkylsulphonyl-($C_1$-$C_6$)alkyl, ($C_1$-$C_6$)alkylsulphonyloxy, ($C_1$-$C_6$)alkylcarbonyl, ($C_1$-$C_6$)alkylthiocarbonyl, ($C_1$-$C_6$)haloalkylcarbonyl, ($C_1$-$C_6$)alkylcarbonyloxy, ($C_1$-$C_6$)alkoxycarbonyl, ($C_1$-$C_6$)halogenalkoxycarbonyl, aminocarbonyl, ($C_1$-$C_6$)alkylaminocarbonyl, ($C_1$-$C_6$)alkylaminothiocarbonyl, di-($C_1$-$C_6$)alkylaminocarbonyl, di-($C_1$-$C_6$)alkylaminothiocarbonyl, ($C_2$-$C_6$)alkenylaminocarbonyl, di-($C_2$-$C_6$)-alkenylaminocarbonyl, ($C_3$-$C_8$)cycloalkylaminocarbonyl, ($C_1$-$C_6$)alkylsulphonylamino, ($C_1$-$C_6$)alkylamino, di-($C_1$-$C_6$)alkylamino, aminosulphonyl, ($C_1$-$C_6$)alkylaminosulphonyl, di-($C_1$-$C_6$)alkylaminosulphonyl, ($C_1$-$C_6$)alkylsulphoximino, aminothiocarbonyl, ($C_1$-$C_6$)alkylaminothiocarbonyl, di-($C_1$-$C_6$)alkyl-aminothiocarbonyl, ($C_3$-$C_8$)cycloalkylamino, NHCO—($C_1$-$C_6$)alkyl (($C_1$-$C_6$)alkylcarbonylamino), represents aryl or hetaryl, each of which is optionally mono- or polysubstituted by identical or different substituents, where (in the case of hetaryl) optionally at least one carbonyl group may be present and/or where possible substituents in each case are as follows: cyano, carboxyl, halogen, nitro, acetyl, hydroxy, amino, SCN, tri-($C_1$-$C_6$)alkylsilyl, ($C_3$-$C_8$)cycloalkyl, ($C_3$-$C_8$)cycloalkyl-($C_3$-$C_8$)cycloalkyl, ($C_1$-$C_6$)alkyl-($C_3$-$C_8$)cycloalkyl, halo($C_3$-$C_8$)cycloalkyl, ($C_1$-$C_6$)alkyl, ($C_1$-$C_6$)haloalkyl, ($C_1$-$C_6$)cyanoalkyl, ($C_1$-$C_6$)hydroxyalkyl, hydroxycarbonyl-($C_1$-$C_6$)-alkoxy, ($C_1$-$C_6$)alkoxycarbonyl-($C_1$-$C_6$)alkyl, ($C_1$-$C_6$)alkoxy-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)haloalkynyl, ($C_2$-$C_6$)cyanoalkynyl, ($C_1$-$C_6$)alkoxy, ($C_1$-$C_6$)haloalkoxy, ($C_1$-$C_6$)cyanoalkoxy, ($C_1$-$C_6$)alkoxycarbonyl-($C_1$-$C_6$)alkoxy, ($C_1$-$C_6$)alkoxy-($C_1$-$C_6$)alkoxy, ($C_1$-$C_6$)alkylhydroxyimino, ($C_1$-$C_6$)alkoxyimino, ($C_1$-$C_6$)alkyl-($C_1$-$C_6$)alkoxyimino, ($C_1$-$C_6$)haloalkyl-($C_1$-$C_6$)alkoxyimino, ($C_1$-$C_6$)alkylthio, ($C_1$-$C_6$)haloalkylthio, ($C_1$-$C_6$)alkoxy-($C_1$-$C_6$)alkylthio, ($C_1$-$C_6$)alkylthio-($C_1$-$C_6$)alkyl, ($C_1$-$C_6$)alkylsulphinyl, ($C_1$-$C_6$)haloalkylsulphinyl, ($C_1$-$C_6$)alkoxy-($C_1$-$C_6$)alkylsulphinyl, ($C_1$-$C_6$)alkylsulphinyl-($C_1$-$C_6$)alkyl, ($C_1$-$C_6$)alkylsulphonyl, ($C_1$-$C_6$)haloalkylsulphonyl, ($C_1$-$C_6$)alkoxy-($C_1$-$C_6$)alkylsulphonyl, ($C_1$-$C_6$)alkylsulphonyl-($C_1$-$C_6$)alkyl, ($C_1$-$C_6$)alkylsulphonyloxy, ($C_1$-$C_6$)alkylcarbonyl, ($C_1$-$C_6$)haloalkylcarbonyl, ($C_1$-$C_6$)alkylcarbonyloxy, ($C_1$-$C_6$)alkoxycarbonyl, ($C_1$-$C_6$)haloalkoxycarbonyl, aminocarbonyl, ($C_1$-$C_6$)alkylaminocarbonyl, di-($C_1$-$C_6$)alkylaminocarbonyl, ($C_2$-$C_6$)alkenylaminocarbonyl, di-($C_2$-$C_6$)-alkenylaminocarbonyl, ($C_3$-$C_8$)cycloalkylaminocarbonyl, ($C_1$-$C_6$)alkylsulphonylamino, ($C_1$-$C_6$)alkylamino, di-($C_1$-$C_6$)alkylamino, aminosulphonyl, ($C_1$-$C_6$)alkylaminosulphonyl, di-($C_1$-$C_6$)alkylaminosulphonyl, ($C_1$-$C_6$)alkylsulphoximino, aminothiocarbonyl, ($C_1$-$C_6$)alkylaminothiocarbonyl, di-($C_1$-$C_6$)alkylaminothiocarbonyl, ($C_3$-$C_8$)cycloalkylamino, ($C_1$-$C_6$)alkylcarbonylamino, $R^4$ represents hydrogen, cyano, halogen, nitro, acetyl, hydroxy, amino, SCN, tri($C_1$-$C_6$)alkylsilyl, ($C_3$-$C_8$)cycloalkyl, ($C_3$-$C_8$)cycloalkyl-($C_3$-$C_8$)cycloalkyl, ($C_1$-$C_6$)alkyl-($C_3$-$C_8$)cycloalkyl, halo($C_3$-$C_8$)cycloalkyl, ($C_1$-$C_6$)alkyl, ($C_1$-$C_6$)haloalkyl, ($C_1$-$C_6$)cyanoalkyl, ($C_1$-$C_6$)hydroxyalkyl, hydroxycarbonyl-($C_1$-$C_6$)-alkoxy, ($C_1$-$C_6$)alkoxycarbonyl-($C_1$-$C_6$)alkyl, ($C_1$-$C_6$)alkoxy-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)haloalkynyl, ($C_2$-$C_6$)cyanoalkynyl, ($C_1$-$C_6$)alkoxy, ($C_1$-$C_6$)haloalkoxy, ($C_1$-$C_6$)cyanoalkoxy, ($C_1$-$C_6$)alkoxycarbonyl-($C_1$-$C_6$)alkoxy, ($C_1$-$C_6$)alkoxy-($C_1$-$C_6$)alkoxy, ($C_1$-$C_6$)alkylhydroxyimino, ($C_1$-$C_6$)alkoxyimino, ($C_1$-$C_6$)alkyl-($C_1$-$C_6$)alkoxyimino, ($C_1$-$C_6$)haloalkyl-($C_1$-$C_6$)alkoxyimino, ($C_1$-$C_6$)alkylthio, ($C_1$-$C_6$)haloalkylthio, ($C_1$-$C_6$)alkoxy-($C_1$-$C_6$)alkylthio, ($C_1$-$C_6$)alkylthio-($C_1$-$C_6$)alkyl, ($C_1$-$C_6$)alkylsulphinyl, ($C_1$-$C_6$)haloalkylsulphinyl, ($C_1$-$C_6$)alkoxy-($C_1$-$C_6$)alkylsulphinyl, ($C_1$-$C_6$)alkylsulphinyl-($C_1$-$C_6$)alkyl, ($C_1$-$C_6$)alkylsulphonyl, ($C_1$-$C_6$)haloalkylsulphonyl, ($C_1$-$C_6$)alkoxy-($C_1$-$C_6$)alkylsulphonyl, ($C_1$-$C_6$)alkylsulphonyl-($C_1$-$C_6$)alkyl, ($C_1$-$C_6$)alkylsulphonyloxy, ($C_1$-$C_6$)alkylcarbonyl, ($C_1$-$C_6$)alkylthiocarbonyl, ($C_1$-$C_6$)haloalkylcarbonyl, ($C_1$-$C_6$)alkylcarbonyloxy, ($C_1$-$C_6$)alkoxycarbonyl, ($C_1$-$C_6$)halogenalkoxycarbonyl, aminocarbonyl, ($C_1$-$C_6$)alkylaminocarbonyl, ($C_1$-$C_6$)alkylaminothiocarbonyl, di-($C_1$-$C_6$)alkylaminocarbonyl, di-($C_1$-$C_6$)alkylaminothiocarbonyl, ($C_2$-$C_6$)alkenylaminocarbonyl, di-($C_2$-$C_6$)-alkenylaminocarbonyl, ($C_3$-$C_8$)cycloalkylaminocarbonyl, ($C_1$-$C_6$)alkylsulphonylamino, ($C_1$-$C_6$)alkylamino, di-($C_1$-$C_6$)alkylamino, aminosulphonyl, ($C_1$-$C_6$)alkylaminosulphonyl, di-($C_1$-$C_6$)alkylaminosulphonyl, ($C_1$-$C_6$)alkylsulphoximino, aminothiocarbonyl, ($C_1$-$C_6$)alkylaminothiocarbonyl, di-($C_1$-$C_6$)alkyl-aminothiocarbonyl, ($C_3$-$C_8$)cycloalkylamino, or NHCO—($C_1$-$C_6$)alkyl (($C_1$-$C_6$)alkylcarbonylamino), X represents a partially saturated or saturated heterocyclic or heteroaromatic 8-, 9-, 10-, 11- or 12-membered fused bicyclic or tricyclic ring system, where optionally at least one carbonyl group can be present and/or where the ring system is optionally mono- or polysubstituted by identical or different substituents, and where the substituents, independently of one another, can be selected from hydrogen, cyano, halogen, nitro, acetyl, hydroxy, amino, SCN, tri ($C_1$-$C_6$)alkylsilyl, ($C_3$-$C_8$)cycloalkyl, ($C_3$-$C_8$)cycloalkyl-($C_3$-$C_8$)cycloalkyl, ($C_1$-$C_6$)alkyl-($C_3$-$C_8$)cycloalkyl, halo ($C_3$-$C_8$)cycloalkyl, ($C_1$-$C_6$)alkyl, ($C_1$-$C_6$)haloalkyl, ($C_1$-$C_6$)cyanoalkyl, ($C_1$-$C_6$)hydroxyalkyl, hydroxycarbonyl-($C_1$-$C_6$)-alkoxy, ($C_1$-$C_6$)alkoxycarbonyl-($C_1$-$C_6$)alkyl, ($C_1$-$C_6$)alkoxy-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)alkynyloxy-($C_1$-$C_4$)alkyl, ($C_2$-$C_6$)haloalkynyl, ($C_2$-$C_6$)cyanoalkynyl, ($C_1$-$C_6$)alkoxy, ($C_1$-$C_6$)haloalkoxy, ($C_1$-$C_6$)haloalkoxy-($C_1$-$C_6$)alkyl, ($C_2$-$C_6$)alkenyloxy-($C_1$-$C_6$)alkyl, ($C_2$-$C_6$)haloalkenyloxy-($C_1$-$C_6$)alkyl, ($C_1$-$C_6$)cyanoalkoxy, ($C_1$-$C_6$)alkoxycarbonyl-($C_1$-$C_6$)alkoxy, ($C_1$-$C_6$)alkoxy-($C_1$-$C_6$)alkoxy, ($C_1$-$C_6$)alkylhydroxyimino, ($C_1$-$C_6$)alkoxyimino, ($C_1$-$C_6$)alkyl-($C_1$-$C_6$)alkoxyimino, ($C_1$-$C_6$)haloalkyl-($C_1$-$C_6$)alkoxyimino, ($C_1$-$C_6$)alkylthio, ($C_1$-$C_6$)haloalkylthio, ($C_1$-$C_6$)alkoxy-($C_1$-$C_6$)alkylthio, ($C_1$-$C_6$)alkylthio-($C_1$-$C_6$)alkyl, ($C_1$-$C_6$)alkylsulphinyl, ($C_1$-$C_6$)haloalkylsulphinyl, ($C_1$-$C_6$)alkoxy-($C_1$-$C_6$)alkylsulphinyl, ($C_1$-$C_6$)alkylsulphinyl-($C_1$-$C_6$)alkyl, ($C_1$-$C_6$)alkylsulphonyl, ($C_1$-$C_6$)haloalkylsulphonyl, ($C_1$-$C_6$)alkoxy-($C_1$-$C_6$)alkylsulphonyl, ($C_1$-$C_6$)alkylsulphonyl-($C_1$-$C_6$)alkyl, ($C_1$-$C_6$)alkylsulphonyloxy, ($C_1$-$C_6$)alkylcarbonyl, ($C_1$-$C_6$)alkylcarbonyl-($C_1$-$C_6$)alkyl, ($C_1$-$C_6$)alkylthiocarbonyl, ($C_1$-$C_6$)haloalkylcarbonyl, ($C_1$-$C_6$)alkylcarbonyloxy, ($C_1$-$C_6$)alkoxycarbonyl, ($C_1$-$C_6$)haloalkoxycarbonyl, aminocarbonyl, ($C_1$-$C_6$)alkylaminocarbonyl, ($C_1$-$C_6$)alkylaminothiocarbonyl, di-($C_1$-$C_6$)alkylaminocarbonyl, di-($C_1$-$C_6$)alkylaminothiocarbonyl, ($C_2$-$C_6$)alkenylaminocarbonyl, di-($C_2$-$C_6$)-alkenylaminocarbonyl, ($C_3$-$C_8$)cycloalkylaminocarbonyl, ($C_1$-$C_6$)alkylsulphonylamino, ($C_1$-$C_6$)alkylamino, di-($C_1$-$C_6$)alkylamino, aminosulphonyl, ($C_1$-$C_6$)alkylaminosulphonyl, di-($C_1$-$C_6$)alkylaminosulphonyl, ($C_1$-$C_6$)alkylsulphoximino, aminothiocarbonyl, ($C_1$-$C_6$)alkylaminothiocarbonyl, di-($C_1$-$C_6$)alkylaminothiocarbonyl, ($C_3$-$C_8$)cycloalkylamino, NHCO—($C_1$-$C_6$)alkyl (($C_1$-$C_6$)alkylcarbonylamino), or where the substituents independently of one another may be selected from phenyl or a 5- or 6-membered heteroaromatic ring, where phenyl or the ring may optionally be mono- or polysubstituted by identical or different substituents from the group consisting of $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $NO_2$, $C_1$-$C_4$-alkoxy, $C_1$-$C_4$-haloalkoxy, n represents 0, 1 or 2.

DETAILED DESCRIPTION OF A PREFERRED EMBODIMENT

It has additionally been found that the compounds of the formula (I) have very good efficacy as pesticides, preferably as insecticides and/or acaricides, and additionally generally have very good plant compatibility, in particular with respect to crop plants.

A general definition of the compounds of the invention is provided by the formula (I). Preferred substituents or ranges of the radicals given in the formulae mentioned above and below are illustrated hereinafter:

Configuration 2

$A^1$ represents nitrogen, $=N^+(O^-)-$ or $=C(R^4)-$, $R^1$ preferably represents ($C_1$-$C_4$)alkyl, ($C_1$-$C_4$)hydroxyalkyl, ($C_1$-$C_4$)haloalkyl, ($C_1$-$C_4$)cyanoalkyl, ($C_1$-$C_4$)alkoxy-($C_1$-$C_4$)alkyl, ($C_1$-$C_4$)haloalkoxy-($C_1$-$C_4$)alkyl, ($C_2$-$C_4$)alkenyl, ($C_2$-$C_4$)alkenyloxy-($C_1$-$C_4$)alkyl, ($C_2$-$C_4$)haloalkenyloxy-($C_1$-$C_4$)alkyl, ($C_2$-$C_4$)haloalkenyl, ($C_2$-$C_4$)cyanoalkenyl, ($C_2$-$C_4$)alkynyl, ($C_2$-$C_4$)alkynyloxy-($C_1$-$C_4$)alkyl, ($C_2$-$C_4$)haloalkynyloxy-($C_1$-$C_4$)alkyl, ($C_2$-$C_4$)haloalkynyl, ($C_2$-$C_4$)cyanoalkynyl, ($C_3$-$C_6$)cycloalkyl, ($C_3$-$C_6$)cycloalkyl($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkylamino, di-($C_1$-$C_4$)alkylamino, ($C_3$-$C_6$)cycloalkylamino, ($C_1$-$C_4$)alkylcarbonylamino, ($C_1$-$C_4$)alkylthio-($C_1$-$C_4$)alkyl, ($C_1$-$C_4$)haloalkylthio-($C_1$-$C_4$)alkyl, ($C_1$-$C_4$)alkylsulphinyl-($C_1$-$C_4$)alkyl, ($C_1$-$C_4$)haloalkylsulphinyl-($C_1$-$C_4$)alkyl, ($C_1$-$C_4$)alkylsulphonyl- ($C_1$-$C_4$)alkyl, ($C_1$-$C_4$)alkylcarbonyl-($C_1$-$C_4$)alkyl, ($C_1$-$C_4$)haloalkylcarbonyl-($C_1$-$C_4$)alkyl, ($C_1$-$C_4$)alkylsulphonylamino, or represents ($C_1$-$C_4$)alkyl, ($C_1$-$C_4$)alkoxy, ($C_2$-$C_4$)alkenyl, ($C_2$-$C_4$)alkynyl, ($C_3$-$C_6$)cycloalkyl, each of which is optionally mono- or disubstituted by identical or different substituents from the group consisting of aryl, hetaryl and heterocyclyl, where aryl, hetaryl and heterocyclyl may in each case optionally be mono- or disubstituted by identical or different substituents from the group consisting of halogen, cyano, carbamoyl, aminosulphonyl, ($C_1$-$C_4$)-alkyl, ($C_3$-$C_4$)cycloalkyl, ($C_1$-$C_4$)alkoxy, ($C_1$-$C_4$)haloalkyl, ($C_1$-$C_4$)haloalkoxy, ($C_1$-$C_4$)alkylthio, ($C_1$-$C_4$)alkylsulphinyl, ($C_1$-$C_4$)alkylsulphonyl, ($C_1$-$C_4$)alkylsulphimino, or $R^1$ preferably represents aryl, hetaryl or heterocyclyl, each of which is optionally mono- or disubstituted by identical or different substituents from the group consisting of halogen, cyano, carbamoyl, ($C_1$-$C_4$)alkyl, ($C_3$-$C_6$)cycloalkyl, ($C_1$-$C_4$)-alkoxy, ($C_1$-$C_4$)haloalkyl, ($C_1$-$C_4$)haloalkoxy, ($C_1$-$C_4$)alkylthio, ($C_1$-$C_4$)alkylsulphinyl, ($C_1$-$C_4$)alkylsulphonyl, ($C_1$-$C_4$)alkylsulphimino, ($C_1$-$C_4$)alkylsulphoximino, ($C_1$-$C_4$)alkylcarbonyl, ($C_3$-$C_4$)trialkylsilyl, (=O) (only in the case of heterocyclyl) and (=O)$_2$ (only in the case of heterocyclyl), $R^2$ preferably represents a saturated, partially saturated or heteroaromatic ring which is optionally mono- or disubstituted by identical or different substituents, in which at least one carbon atom is replaced by a heteroatom from the group consisting of N, O and S, where in each case optionally at least one carbonyl group may be present and/or where possible substituents are in each case: cyano, halogen, nitro, acetyl, amino, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, ($C_1$-$C_4$)alkoxy, ($C_1$-$C_4$)haloalkoxy, ($C_1$-$C_4$)cyanoalkoxy, ($C_1$-$C_4$)alkoxy-($C_1$-$C_4$)alkoxy, ($C_1$-$C_4$)alkoxyimino, —N=C(H)—O($C_1$-$C_4$)alkyl, —C(H)=N—O($C_1$-$C_4$)alkyl, ($C_1$-$C_4$)haloalkyl-($C_1$-$C_4$)alkoxyimino, ($C_1$-$C_4$)alkylthio, ($C_1$-$C_4$)haloalkylthio, ($C_1$-$C_4$)alkylthio-($C_1$-$C_4$)alkyl, ($C_1$-$C_4$)alkylsulphinyl, ($C_1$-$C_4$)haloalkylsulphinyl, ($C_1$-$C_4$)alkylsulphinyl-($C_1$-$C_4$)alkyl, ($C_1$-$C_4$)alkylsulphonyl, ($C_1$-$C_4$)haloalkylsulphonyl, ($C_1$-$C_4$)alkylsulphonyl-($C_1$-$C_4$)alkyl, ($C_1$-$C_4$)alkylsulphonyloxy, ($C_1$-$C_4$)alkylcarbonyl, ($C_1$-$C_4$)haloalkylcarbonyl, aminocarbonyl, ($C_1$-$C_4$)alkylaminocarbonyl, di-($C_1$-$C_4$)alkylaminocarbonyl, ($C_1$-$C_4$)alkylsulphonylamino, ($C_1$-$C_4$)alkylamino, di-($C_1$-$C_4$)alkylamino, aminosulphonyl, ($C_1$-$C_4$)alkylaminosulphonyl, di-($C_1$-$C_4$)alkylaminosulphonyl, ($C_1$-$C_4$)alkylcarbonylamino, V preferably represents a saturated, partially saturated or heteroaromatic ring which is optionally mono- or disubstituted by identical or different substituents, and in which at least one carbon atom is replaced by a heteroatom from the group N, O or S, or represents an aromatic ring optionally mono- or disubstituted by identical or different substituents, where in each case optionally at least one carbonyl group may be present and/or where possible substituents are in each case as follows: cyano, halogen, nitro, acetyl, amino, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, ($C_1$-$C_4$)alkoxy, ($C_1$-$C_4$)haloalkoxy, ($C_1$-$C_4$)cyanoalkoxy, ($C_1$-$C_4$)alkoxy-($C_1$-$C_4$)alkoxy, ($C_1$-$C_4$)alkoxyimino, —N=C(H)—O($C_1$-$C_4$)alkyl, —C(H)=N—O($C_1$-$C_4$)alkyl, ($C_1$-$C_4$)haloalkyl-($C_1$-$C_4$)alkoxyimino, ($C_1$-$C_4$)alkylthio, ($C_1$-$C_4$)haloalkylthio, ($C_1$-$C_4$)alkylthio-($C_1$-$C_4$)alkyl, ($C_1$-$C_4$)alkylsulphinyl, ($C_1$-$C_4$)haloalkylsulphinyl, ($C_1$-$C_4$)alkylsulphinyl-($C_1$-$C_4$)alkyl, ($C_1$-$C_4$)alkylsulphonyl, ($C_1$-$C_4$)haloalkylsulphonyl, ($C_1$-$C_4$)alkylsulphonyl-($C_1$-$C_4$)alkyl, ($C_1$-$C_4$)alkylsulphonyloxy, ($C_1$-$C_4$)alkylcarbonyl, ($C_1$-$C_4$)haloalkylcarbonyl, aminocarbonyl, ($C_1$-$C_4$)alkylaminocarbonyl, di-($C_1$-$C_4$)alkylaminocarbonyl, ($C_1$-$C_4$)alkylsulphonylamino, ($C_1$-$C_4$)alkylamino, di-($C_1$-$C_4$)alkylamino, aminosulphonyl, ($C_1$-$C_4$)alkylaminosulphonyl, di-($C_1$-$C_4$)alkylaminosulphonyl, ($C_1$-$C_4$)alkylcarbonylamino, $R^3$ preferably represents hydrogen, cyano, halogen, nitro, acetyl, hydroxy, amino, SCN, tri($C_1$-$C_4$)alkylsilyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)halolkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkoxy-($C_1$-$C_4$)alkoxy, ($C_1$-$C_4$)alkylhydroxyimino, ($C_1$-$C_4$)alkoxyimino, ($C_1$-$C_4$)alkyl-($C_1$-$C_4$)alkoxyimino, ($C_1$-$C_4$)haloalkyl-($C_1$-$C_4$)alkoxyimino, ($C_1$-$C_4$)alkylthio, ($C_1$-$C_4$)haloalkylthio, ($C_1$-$C_4$)alkylthio-($C_1$-$C_4$)alkyl, ($C_1$-$C_4$)alkylsulphinyl, ($C_1$-$C_4$)haloalkylsulphinyl, ($C_1$-$C_4$)alkylsulphinyl-($C_1$-$C_4$)alkyl, ($C_1$-$C_4$)alkylsulphonyl, ($C_1$-$C_4$)haloalkylsulphonyl, ($C_1$-$C_4$)alkylsulphonyl-($C_1$-$C_4$)alkyl, ($C_1$-$C_4$)alkylsulphonyloxy, ($C_1$-$C_4$)alkylcarbonyl, ($C_1$-$C_4$)haloalkylcarbonyl, aminocarbonyl, aminothiocarbonyl, ($C_1$-$C_4$)alkylaminocarbonyl, di-($C_1$-$C_4$)alkylaminocarbonyl, ($C_1$-$C_4$)alkylsulphonylamino, ($C_1$-$C_4$)alkylamino, di-($C_1$-$C_4$)alkylamino, aminosulphonyl, ($C_1$-$C_4$)alkylaminosulphonyl, di-($C_1$-$C_4$)alkylaminosulphonyl, aminothiocarbonyl, NHCO—($C_1$-$C_4$)alkyl (($C_1$-$C_4$)alkylcarbonylamino), furthermore preferably represents phenyl or hetaryl, each of which is optionally mono- or disubstituted by identical or different substituents, where (in the case of hetaryl) optionally at least one carbonyl group may be present and/or where possible substituents are in each case as follows: cyano, halogen, nitro, acetyl, amino, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkoxy-($C_1$-$C_4$)alkoxy, ($C_1$-$C_4$)alkylhydroxyimino, ($C_1$-$C_4$)alkoxyimino, ($C_1$-$C_4$)alkyl-($C_1$-$C_4$)alkoxyimino, ($C_1$-$C_4$)haloalkyl-($C_1$-$C_4$)alkoxyimino, ($C_1$-$C_4$)alkylthio, ($C_1$-$C_4$)haloalkylthio, ($C_1$-$C_4$)alkylthio-($C_1$-$C_4$)alkyl, ($C_1$-$C_4$)alkylsulphinyl, ($C_1$-$C_4$)haloalkylsulphinyl, ($C_1$-$C_4$)alkylsulphinyl-($C_1$-$C_4$)alkyl, ($C_1$-$C_4$)alkylsulphonyl, ($C_1$-$C_4$)haloalkylsulphonyl, ($C_1$-$C_4$)alkylsulphonyl-($C_1$-$C_4$)alkyl, ($C_1$-$C_4$)alkylsulphonyloxy, ($C_1$-$C_4$)alkylcarbonyl, ($C_1$-$C_4$)haloalkylcarbonyl, aminocarbonyl, ($C_1$-$C_4$)alkylaminocarbonyl, di-($C_1$-$C_4$)alkylaminocarbonyl, ($C_1$-$C_4$)alkylsulphonylamino, ($C_1$-$C_4$)alkylamino, di-($C_1$-$C_4$)alkylamino, aminosulphonyl, ($C_1$-$C_4$)alkylaminosulphonyl, di-($C_1$-$C_4$)alkylaminosulphonyl, NHCO—($C_1$-$C_4$)alkyl (($C_1$-$C_4$)alkylcarbonylamino), $R^4$ preferably represents hydrogen, cyano, halogen, nitro, acetyl, hydroxy, amino, SCN, tri($C_1$-$C_4$)alkylsilyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)halolkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkoxy-($C_1$-$C_4$)alkoxy, ($C_1$-$C_4$)alkylhydroxyimino, ($C_1$-$C_4$)alkoxyimino, ($C_1$-$C_4$)alkyl-($C_1$-$C_4$)alkoxyimino, ($C_1$-$C_4$)haloalkyl-($C_1$-$C_4$)alkoxyimino, ($C_1$-$C_4$)alkylthio, ($C_1$-$C_4$)haloalkylthio, ($C_1$-$C_4$)alkylthio-($C_1$-$C_4$)alkyl, ($C_1$-$C_4$)alkylsulphinyl, ($C_1$-$C_4$)haloalkylsulphinyl, ($C_1$-$C_4$)alkylsulphinyl-($C_1$-$C_4$)alkyl, ($C_1$-$C_4$)alkylsulphonyl, ($C_1$-$C_4$)haloalkylsulphonyl, ($C_1$-$C_4$)alkylsulphonyl-($C_1$-$C_4$)alkyl, ($C_1$-$C_4$)alkylsulphonyloxy, ($C_1$-$C_4$)alkylcarbonyl, ($C_1$-$C_4$)haloalkylcarbonyl, aminocarbonyl, aminothiocarbonyl, ($C_1$-$C_4$)alkylaminocarbonyl, di-($C_1$-$C_4$)alkylaminocarbonyl, ($C_1$-$C_4$)alkylsulphonylamino, ($C_1$-$C_4$)alkylamino, di-($C_1$-$C_4$)alkylamino, aminosulphonyl, ($C_1$-$C_4$)alkylaminosulphonyl, di-($C_1$-$C_4$)alkylaminosulphonyl, aminothiocarbonyl or NHCO—($C_1$-$C_4$)alkyl (($C_1$-$C_4$)alkylcarbonylamino), X preferably represents a heteroaromatic 8-, 9-, 10-, 11- or 12-membered fused bicyclic or tricyclic ring system, where the ring system is optionally mono- or polysubstituted by identical or different substituents, and where the substituents, independently of one another, can be selected from hydrogen, cyano, halogen, nitro, acetyl, hydroxy, amino, SCN, tri-($C_1$-$C_6$)alkylsilyl, ($C_3$-$C_8$)cycloalkyl, ($C_3$-$C_8$)cycloalkyl-($C_3$-$C_8$)cycloalkyl, ($C_1$-$C_6$)alkyl-($C_3$-$C_8$)cycloalkyl, halo($C_3$-$C_8$)cycloalkyl, ($C_1$-$C_6$)alkyl, ($C_1$-$C_6$)haloalkyl, ($C_1$-$C_6$)cyanoalkyl, ($C_1$-$C_6$)hydroxyalkyl, ($C_1$-$C_6$)alkoxy-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)alkynyloxy-($C_1$-$C_4$)alkyl, ($C_2$-$C_6$)haloalkynyl, ($C_1$-$C_6$)alkoxy, ($C_1$-$C_6$)haloalkoxy, ($C_1$-$C_6$)haloalkoxy-($C_1$-$C_6$)alkyl, ($C_2$-$C_6$)alkenyloxy-($C_1$-$C_6$)alkyl, ($C_2$-$C_6$)haloalkenyloxy-($C_1$-$C_6$)alkyl, ($C_1$-$C_6$)cyanoalkoxy, ($C_1$-$C_6$)alkoxy-($C_1$-$C_6$)alkoxy, ($C_1$-$C_6$)alkylhydroxyimino, ($C_1$-$C_6$)alkoxyimino, ($C_1$-$C_6$)alkyl-($C_1$-$C_6$)alkoxyimino, ($C_1$-$C_6$)alkylthio, ($C_1$-$C_6$)haloalkylthio, ($C_1$-$C_6$)alkoxy-($C_1$-$C_6$)alkylthio, ($C_1$-$C_6$)alkylthio-($C_1$-$C_6$)alkyl, ($C_1$-$C_6$)alkylsulphinyl, ($C_1$-$C_6$)haloalkylsulphinyl, ($C_1$-$C_6$)alkoxy-($C_1$-$C_6$)alkylsulphinyl, ($C_1$-$C_6$)alkylsulphinyl-($C_1$-$C_6$)alkyl, ($C_1$-$C_6$)alkylsulphonyl, ($C_1$-$C_6$)haloalkylsulphonyl, ($C_1$-$C_6$)alkoxy-($C_1$-$C_6$)alkylsulphonyl, ($C_1$-$C_6$)alkylsulphonyl-($C_1$-$C_6$)alkyl, ($C_1$-$C_6$)alkylsulphonyloxy, ($C_1$-$C_6$)alkylcarbonyl, ($C_1$-$C_6$)alkylcarbonyl-($C_1$-$C_6$)alkyl, ($C_1$-$C_6$)alkylthiocarbonyl, ($C_1$-$C_6$)haloalkylcarbonyl, ($C_1$-$C_6$)alkylcarbonyloxy, ($C_1$-$C_6$)alkoxycarbonyl, ($C_1$-$C_6$)haloalkoxycarbonyl, aminocarbonyl, ($C_1$-$C_6$)alkylaminocarbonyl, ($C_1$-$C_6$)alkylaminothiocarbonyl, di-($C_1$-$C_6$)alkylaminocarbonyl, di-($C_1$-$C_6$)alkylaminothiocarbonyl, ($C_3$-$C_8$)cycloalkylaminocarbonyl, ($C_1$-$C_6$)alkylsulphonylamino, ($C_1$-$C_6$)alkylamino, di-($C_1$-$C_6$)alkylamino, aminosulphonyl, ($C_1$-$C_6$)alkylaminosulphonyl, di-($C_1$-$C_6$)alkylaminosulphonyl, ($C_1$-$C_6$)alkylsulphoximino, aminothiocarbonyl, ($C_1$-$C_6$)alkylaminothiocarbonyl, di-($C_1$-$C_6$)alkylaminothiocarbonyl, ($C_3$-$C_8$)cycloalkylamino, NHCO—($C_1$-$C_6$)alkyl (($C_1$-$C_6$)alkylcarbonylamino), or where the substituents independently of one another may be selected from phenyl or a 5- or 6-membered heteroaromatic ring, where phenyl or the ring may optionally be mono- or polysubstituted by identical or different substituents from the group consisting of $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $C_1$-$C_4$-alkoxy, $C_1$-$C_4$-haloalkoxy, n preferably represents 0, 1 or 2.

Configuration 3-1

$A^1$ particularly preferably represents nitrogen or =C($R^4$)—, $R^1$ particularly preferably represents ($C_1$-$C_4$)alkyl, ($C_1$-$C_4$)hydroxyalkyl, ($C_1$-$C_4$)haloalkyl, ($C_2$-$C_4$)alkenyl, ($C_2$-$C_4$)haloalkenyl, ($C_2$-$C_4$)alkynyl, ($C_2$-$C_4$)haloalkynyl, ($C_3$-$C_6$)cycloalkyl, ($C_1$-$C_4$)alkylthio-($C_1$-$C_4$)alkyl, ($C_1$-$C_4$)alkylsulphinyl-($C_1$-$C_4$)alkyl or ($C_1$-$C_4$)alkylsulphonyl-($C_1$-$C_4$)alkyl, $R^2$—V particularly preferably represents a 5- or 6-membered ring optionally mono- or disubstituted by identical or different substituents from the series Q-1 to Q-80, where possible substituents are in each case: cyano, halogen, ($C_1$-$C_4$)alkyl, ($C_1$-$C_4$)alkoxy or ($C_1$-$C_4$)haloalkoxy,

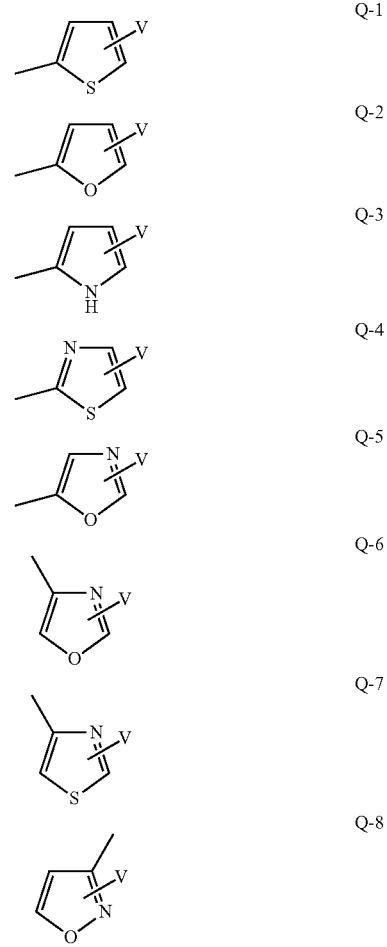

| | | | |
|---|---|---|---|
| 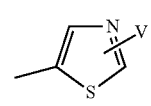 | Q-9 | 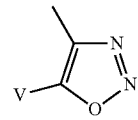 | Q-23 |
| 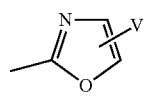 | Q-10 | 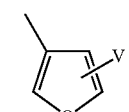 | Q-24 |
| 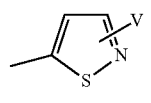 | Q-11 | 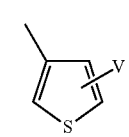 | Q-25 |
| 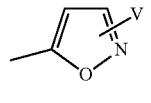 | Q-12 | 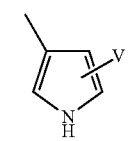 | Q-26 |
| 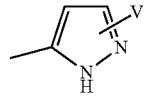 | Q-13 | 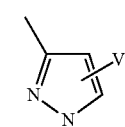 | Q-27 |
| 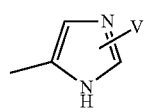 | Q-14 | 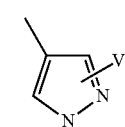 | Q-28 |
| 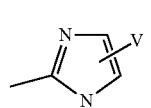 | Q-15 | 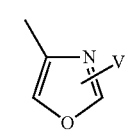 | Q-29 |
| 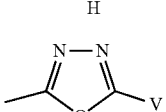 | Q-16 | 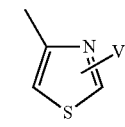 | Q-30 |
| 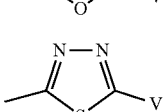 | Q-17 | 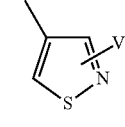 | Q-31 |
| 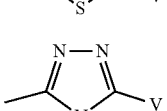 | Q-18 | 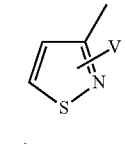 | Q-32 |
| 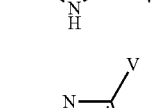 | Q-19 | 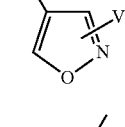 | Q-33 |
| 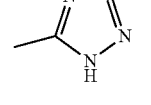 | Q-20 | 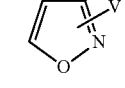 | Q-34 |
| 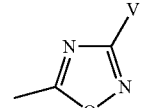 | Q-21 | | |
| 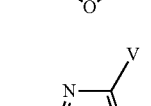 | Q-22 | | |
| 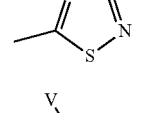 | | | |
| 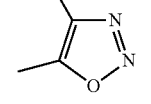 | | | |

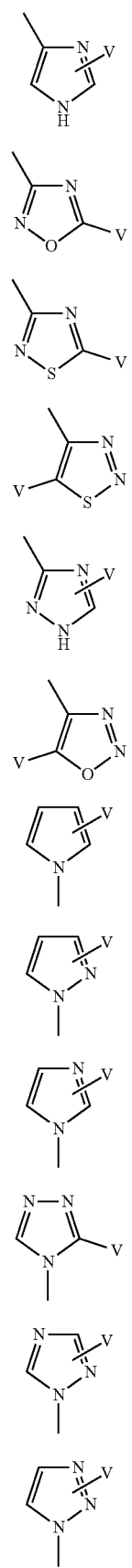
Q-35
Q-36
Q-37
Q-38
Q-39
Q-40
Q-41
Q-42
Q-43
Q-44
Q-45
Q-46
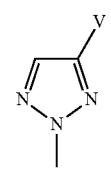 Q-47
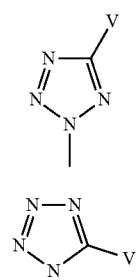 Q-48
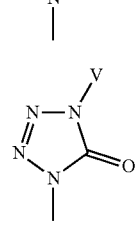 Q-49
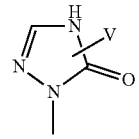 Q-50
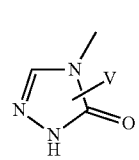 Q-51
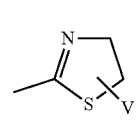 Q-52
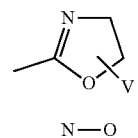 Q-53
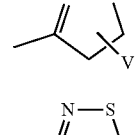 Q-54
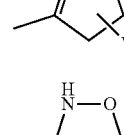 Q-55
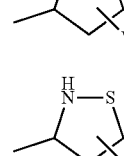 Q-56
 Q-57
 Q-58

Q-59 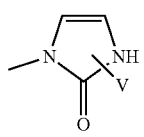
Q-60 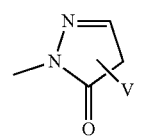
Q-61 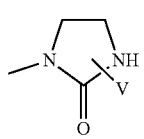
Q-62 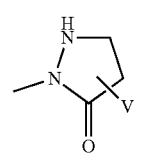
Q-63 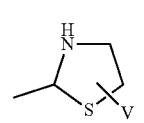
Q-64 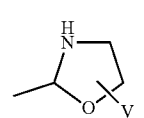
Q-65 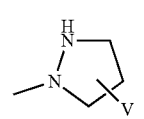
Q-66 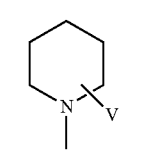
Q-67 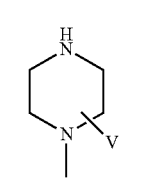
Q-68 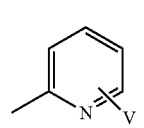
Q-69 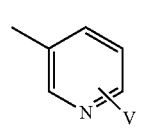
Q-70 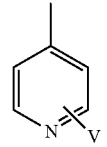
Q-71 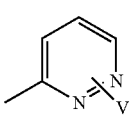
Q-72 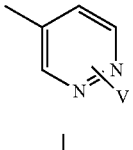
Q-73 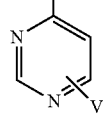
Q-74 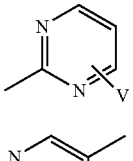
Q-75 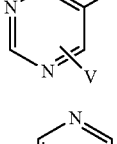
Q-76 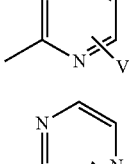
Q-77 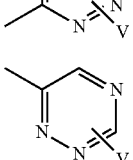
Q-78 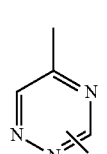
Q-79 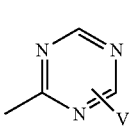
Q-80
where
V particularly preferably represents a 5- or 6-membered ring optionally mono- or disubstituted by identical or different substituents from the series V-1 to V-101, where possible substituents are in each case: cyano, halogen, $(C_1-C_4)$alkyl, $(C_1-C_4)$alkoxy or $(C_1-C_4)$haloalkoxy,

| | |
|---|---|
| 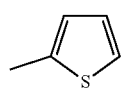 V-1 | 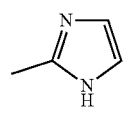 V-15 |
| 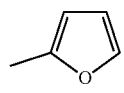 V-2 | 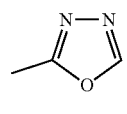 V-16 |
| 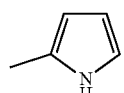 V-3 | 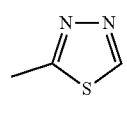 V-17 |
| 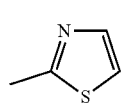 V-4 | 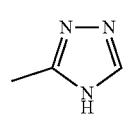 V-18 |
| 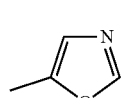 V-5 | 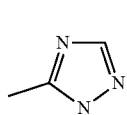 V-19 |
| 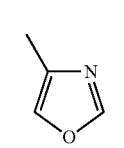 V-6 | 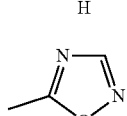 V-20 |
| 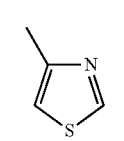 V-7 | 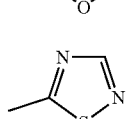 V-21 |
| 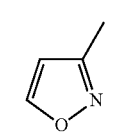 V-8 | 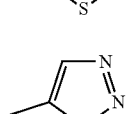 V-22 |
| 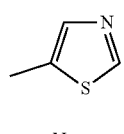 V-9 | 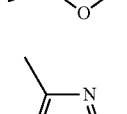 V-23 |
| 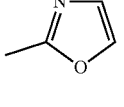 V-10 | 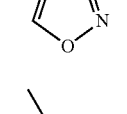 V-24 |
| 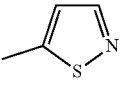 V-11 | 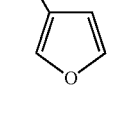 V-25 |
| 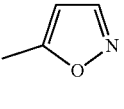 V-12 | 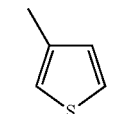 V-26 |
| 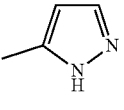 V-13 | 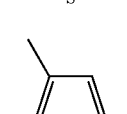 V-27 |
| 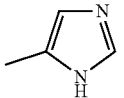 V-14 | 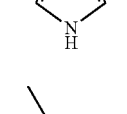 |

-continued
V-28 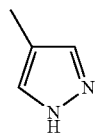
V-29 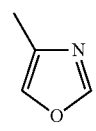
V-30 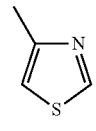
V-31 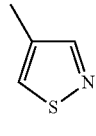
V-32 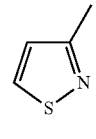
V-33 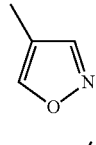
V-34 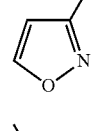
V-35 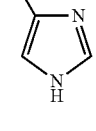
V-36 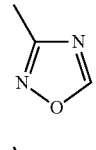
V-37 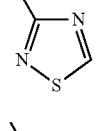
V-38 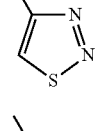
V-39 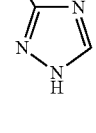
-continued
V-40 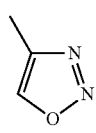
V-41 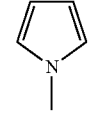
V-42 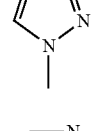
V-43 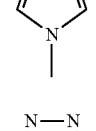
V-44 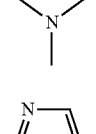
V-45 
V-46 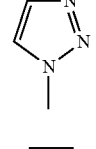
V-47 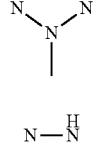
V-48 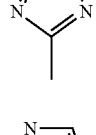
V-49 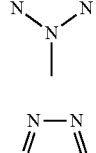
V-50

-continued
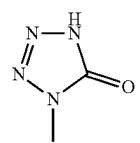 V-51
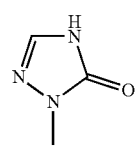 V-52
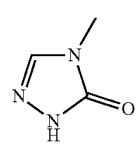 V-53
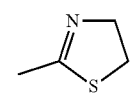 V-54
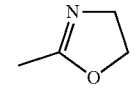 V-55
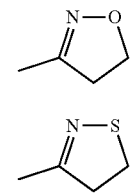 V-56
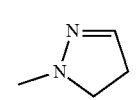 V-57
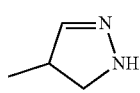 V-58
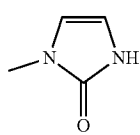 V-59
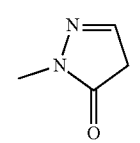 V-60
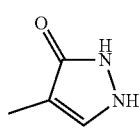 V-61
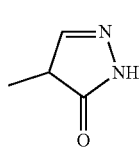 V-62
V-63
-continued
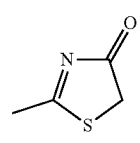 V-64
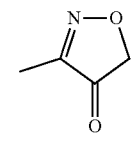 V-65
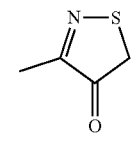 V-66
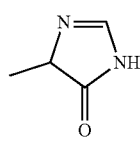 V-67
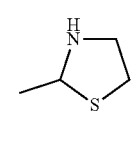 V-68
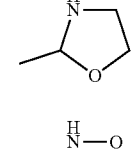 V-69
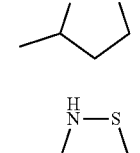 V-70
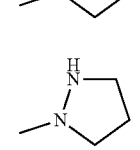 V-71
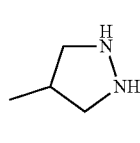 V-72
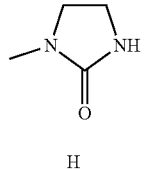 V-73
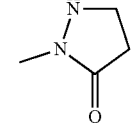 V-74
V-75

-continued
V-76 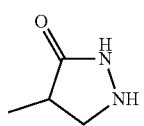
V-77 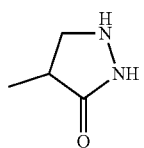
V-78 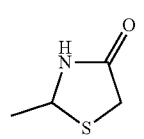
V-79 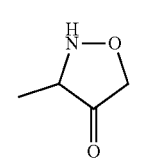
V-80 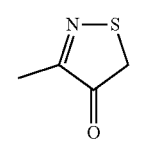
V-81 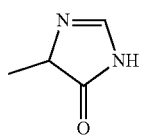
V-82 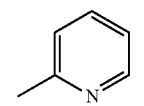
V-83 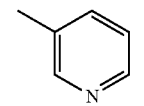
V-84 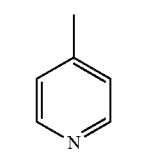
V-85 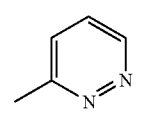
V-86 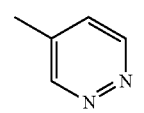
-continued
V-87 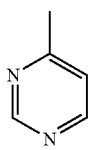
V-88 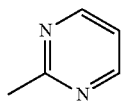
V-89 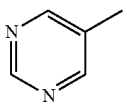
V-90 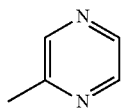
V-91 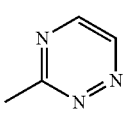
V-92 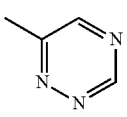
V-93 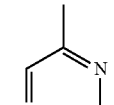
V-94 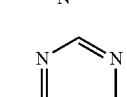
V-95 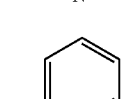
V-96 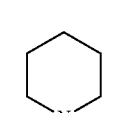
V-97 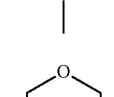
V-98 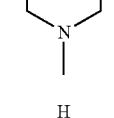
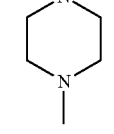

-continued

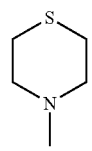
V-99

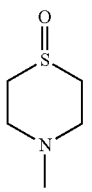
V-100

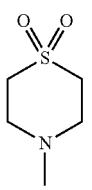
V-101

R³ particularly preferably represents hydrogen, cyano, halogen, nitro, hydroxy, amino, SCN, tri-$(C_1-C_4)$alkylsilyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo$(C_3-C_6)$cycloalkyl, $(C_1-C_4)$alkyl, $(C_1-C_4)$haloalkyl, $(C_1-C_4)$cyanoalkyl, $(C_1-C_4)$alkoxy-$(C_1-C_4)$alkyl, $(C_2-C_4)$alkenyl, $(C_2-C_4)$haloalkenyl, $(C_2-C_4)$cyanoalkenyl, $(C_2-C_4)$alkynyl, $(C_2-C_4)$haloalkynyl, $(C_2-C_4)$cyanoalkynyl, $(C_1-C_4)$alkoxy, $(C_1-C_4)$haloalkoxy, $(C_1-C_4)$cyanoalkoxy, $(C_1-C_4)$alkylhydroxyimino, $(C_1-C_4)$alkoxyimino, $(C_1-C_4)$alkyl-$(C_1-C_4)$alkoxyimino, $(C_1-C_4)$alkylthio, $(C_1-C_4)$haloalkylthio, $(C_1-C_4)$alkylsulphinyl, $(C_1-C_4)$haloalkylsulphinyl, $(C_1-C_4)$alkylsulphonyl, $(C_1-C_4)$haloalkylsulphonyl, $(C_1-C_4)$alkylsulphonyloxy, $(C_1-C_4)$alkylcarbonyl, $(C_1-C_4)$haloalkylcarbonyl, aminocarbonyl, $(C_1-C_4)$alkylaminocarbonyl, di-$(C_1-C_4)$alkylaminocarbonyl, $(C_1-C_4)$alkylsulphonylamino, $(C_1-C_4)$alkylamino, di-$(C_1-C_4)$alkylamino, aminosulphonyl, $(C_1-C_4)$alkylaminosulphonyl, di-$(C_1-C_4)$alkylaminosulphonyl or NHCO—$(C_1-C_4)$alkyl ($(C_1-C_4)$alkylcarbonylamino), R⁴ particularly preferably represents hydrogen, halogen, cyano or $(C_1-C_4)$alkyl, X particularly preferably represents a heteroaromatic 9-membered or 12-membered fused bicyclic or tricyclic ring system from the series consisting of H1 to H20,

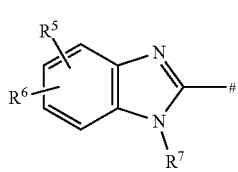
H1

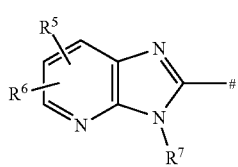
H2

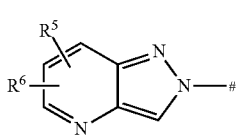
H3

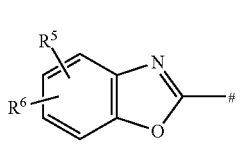
H4

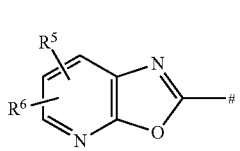
H5

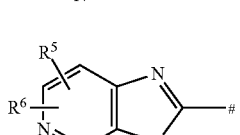
H6

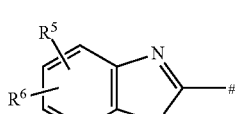
H7

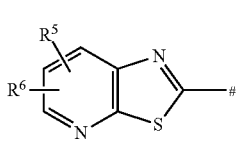
H8

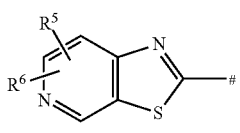
H9

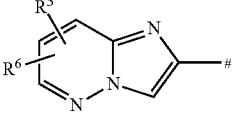
H10

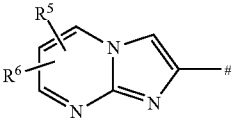
H11

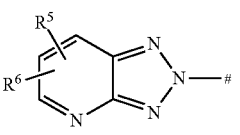
H12

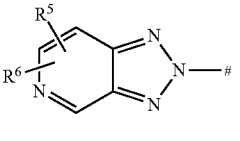
H13

H14 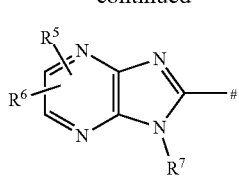

H15 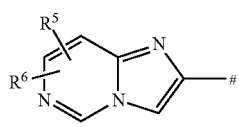

H16 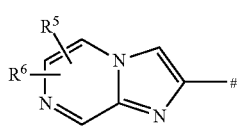

H17 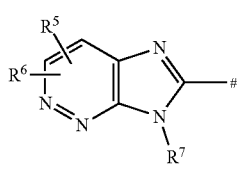

H18 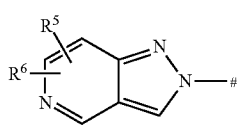

H19 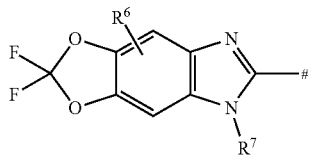

H20 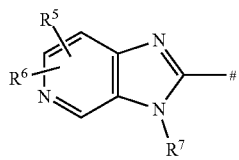

$R^5$, $R^6$ independently of one another particularly preferably represent hydrogen, cyano, halogen, $(C_1$-$C_4)$alkyl, $(C_1$-$C_4)$haloalkyl, $(C_2$-$C_4)$alkenyl, $(C_2$-$C_4)$haloalkenyl, $(C_2$-$C_4)$alkynyl, $(C_2$-$C_4)$haloalkynyl, $(C_3$-$C_6)$cycloalkyl, $(C_3$-$C_6)$cycloalkyl-$(C_3$-$C_6)$cycloalkyl, $(C_1$-$C_4)$alkyl-$(C_3$-$C_6)$cycloalkyl, $(C_1$-$C_4)$alkoxy, $(C_1$-$C_4)$haloalkoxy, $(C_1$-$C_4)$alkoxyimino, $(C_1$-$C_4)$alkylthio, $(C_1$-$C_4)$haloalkylthio, $(C_1$-$C_4)$alkylsulphinyl, $(C_1$-$C_4)$haloalkylsulphinyl, $(C_1$-$C_4)$alkylsulphonyl, $(C_1$-$C_4)$haloalkylsulphonyl, $(C_1$-$C_4)$alkylsulphonyloxy, $(C_1$-$C_4)$alkylcarbonyl, $(C_1$-$C_4)$haloalkylcarbonyl, aminocarbonyl, $(C_1$-$C_4)$alkylaminocarbonyl, di-$(C_1$-$C_4)$alkylaminocarbonyl, $(C_1$-$C_4)$alkylsulphonylamino, $(C_1$-$C_4)$alkylamino, di-$(C_1$-$C_4)$alkylamino, aminosulphonyl, $(C_1$-$C_4)$alkylaminosulphonyl or di-$(C_1$-$C_4)$alkylaminosulphonyl, $R^7$ particularly preferably represents $(C_1$-$C_4)$alkyl, $(C_1$-$C_4)$haloalkyl, $(C_1$-$C_4)$cyanoalkyl, $(C_1$-$C_4)$hydroxyalkyl, $(C_1$-$C_4)$alkoxy-$(C_1$-$C_4)$alkyl, $(C_1$-$C_4)$haloalkoxy-$(C_1$-$C_4)$alkyl, $(C_2$-$C_4)$alkenyl, $(C_2$-$C_4)$alkenyloxy-$(C_1$-$C_4)$alkyl, $(C_2$-$C_4)$haloalkenyloxy-$(C_1$-$C_4)$alkyl, $(C_2$-$C_4)$cyanoalkenyl, $(C_2$-$C_4)$alkynyl, $(C_2$-$C_4)$alkynyloxy-$(C_1$-$C_4)$alkyl, $(C_2$-$C_4)$haloalkynyl, $(C_3$-$C_6)$cycloalkyl, $(C_3$-$C_6)$cycloalkyl-$(C_3$-$C_6)$cycloalkyl, $(C_1$-$C_4)$alkyl-$(C_3$-$C_6)$cycloalkyl, halo$(C_3$-$C_6)$cycloalkyl, $(C_1$-$C_4)$alkylthio-$(C_1$-$C_4)$alkyl, $(C_1$-$C_4)$alkylsulphinyl-$(C_1$-$C_4)$alkyl, $(C_1$-$C_4)$alkylsulphonyl-$(C_1$-$C_4)$alkyl or $(C_1$-$C_4)$alkylcarbonyl-$(C_1$-$C_4)$alkyl, n particularly preferably represents 0, 1 or 2.

In the particularly preferred embodiment, $R^2$ can be optionally mono- or disubstituted, additionally to V, by identical or different substituents selected from cyano, halogen, $(C_1$-$C_4)$alkyl, $(C_1$-$C_4)$alkoxy or $(C_1$-$C_4)$haloalkoxy.

Configuration 3-2

$A^1$, $R^1$, $R^3$, $R^4$, X, $R^5$, $R^6$, $R^7$ and n have the meanings given in configuration 3-1 and $R^2$—V particularly preferably represents a 5- or 6-membered ring optionally mono- or disubstituted by identical or different substituents from the series Q-1 to Q-80, where possible substituents are in each case: cyano, halogen, $(C_1$-$C_4)$alkyl, $(C_1$-$C_4)$haloalkyl, $(C_1$-$C_4)$alkoxy or $(C_1$-$C_4)$haloalkoxy, Q-1 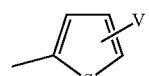

Q-2 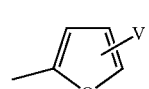

Q-3 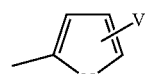

Q-4 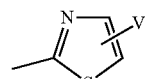

Q-5 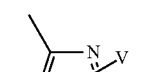

Q-6 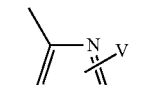

Q-7 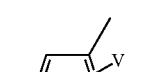

Q-8 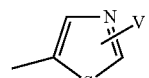

Q-9 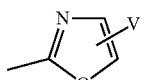

Q-10

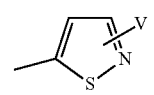 Q-11
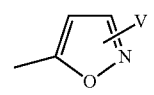 Q-12
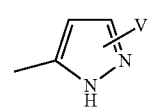 Q-13
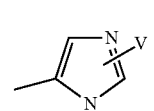 Q-14
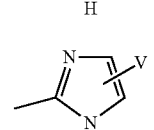 Q-15
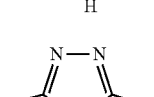 Q-16
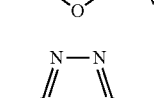 Q-17
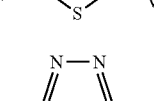 Q-18
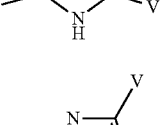 Q-19
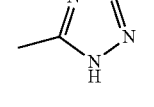 Q-20
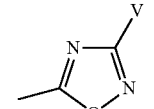 Q-21
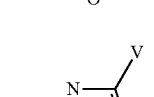 Q-22
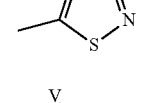 Q-23
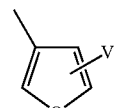 Q-24
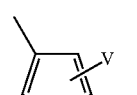 Q-25
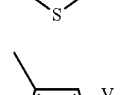 Q-26
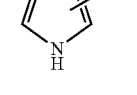 Q-27
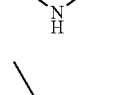 Q-28
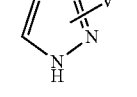 Q-29
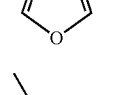 Q-30
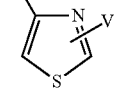 Q-31
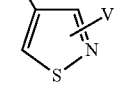 Q-32
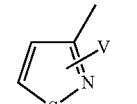 Q-33
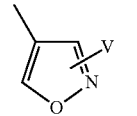 Q-34
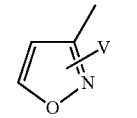 Q-35
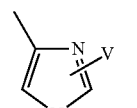

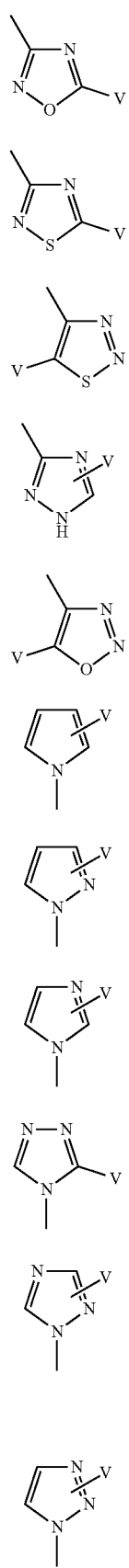
Q-36
Q-37
Q-38
Q-39
Q-40
Q-41
Q-42
Q-43
Q-44
Q-45
Q-46
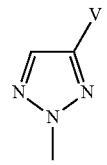
Q-47
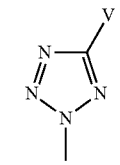
Q-48
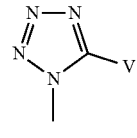
Q-49
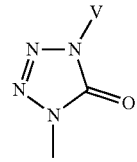
Q-50
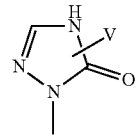
Q-51
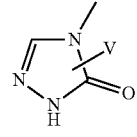
Q-52
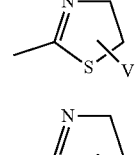
Q-53
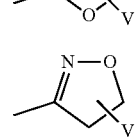
Q-54
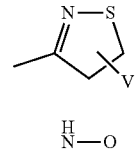
Q-55
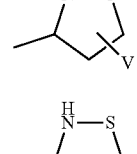
Q-56
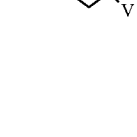
Q-57
Q-58

Q-59 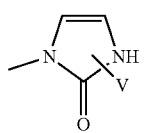
Q-60 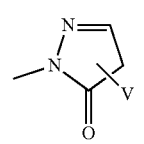
Q-61 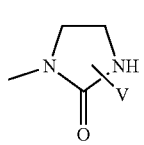
Q-62 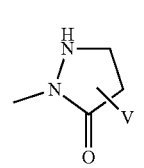
Q-63 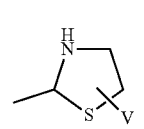
Q-64 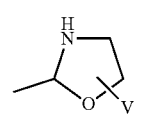
Q-65 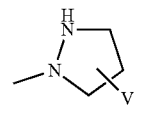
Q-66 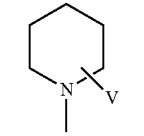
Q-67 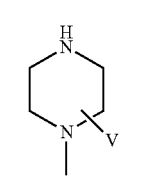
Q-68 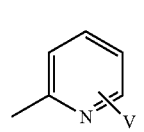
Q-69 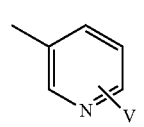
Q-70 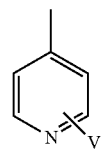
Q-71 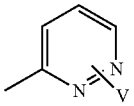
Q-72 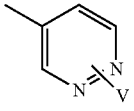
Q-73 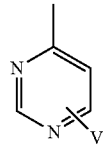
Q-74 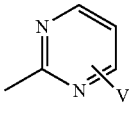
Q-75 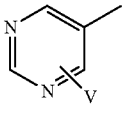
Q-76 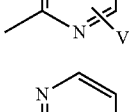
Q-77 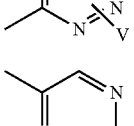
Q-78 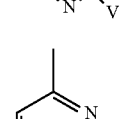
Q-79 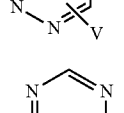
Q-80 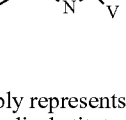
where
V particularly preferably represents a 5- or 6-membered ring optionally mono- or disubstituted by identical or different substituents from the series V-1 to V-101, where possible substituents are in each case: cyano, halogen, $(C_1-C_4)$alkyl, $(C_1-C_4)$haloalkyl, $(C_1-C_4)$alkoxy or $(C_1-C_4)$haloalkoxy, V-1 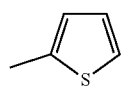
V-2 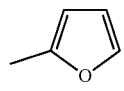
V-3 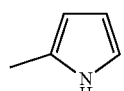
V-4 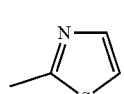
V-5 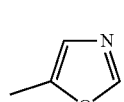
V-6 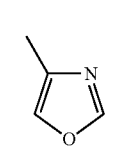
V-7 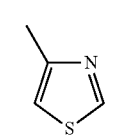
V-8 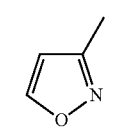
V-9 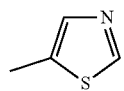
V-10 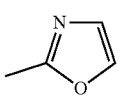
V-11 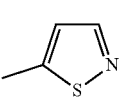
V-12 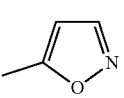
V-13 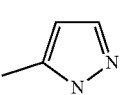
V-14 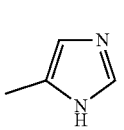
-continued
V-15 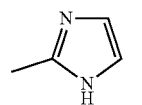
V-16 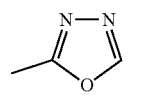
V-17 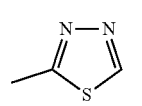
V-18 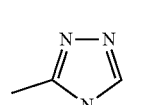
V-19 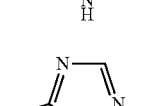
V-20 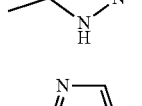
V-21 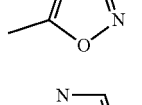
V-22 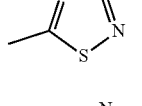
V-23 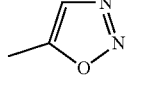
V-24 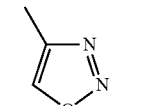
V-25 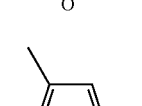
V-26 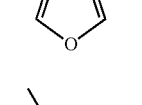
V-27 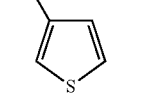

| | | |
|---|---|---|
| V-28 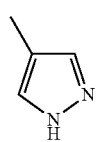 | V-40 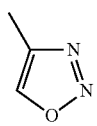 | |
| V-29 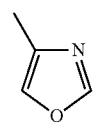 | V-41 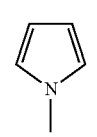 | |
| V-30 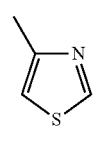 | V-42 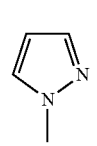 | |
| V-31 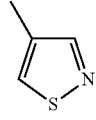 | V-43 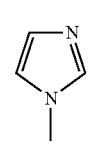 | |
| V-32 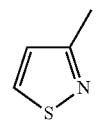 | V-44 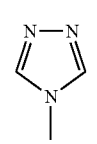 | |
| V-33 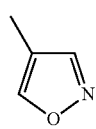 | V-45 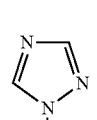 | |
| V-34 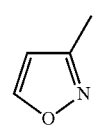 | V-46 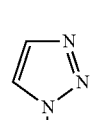 | |
| V-35 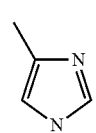 | V-47 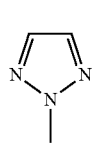 | |
| V-36 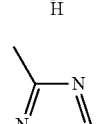 | V-48 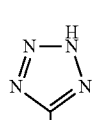 | |
| V-37 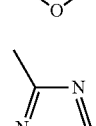 | V-49 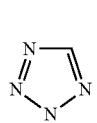 | |
| V-38 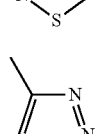 | V-50 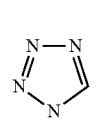 | |
| V-39 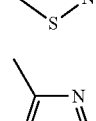 | | |

-continued
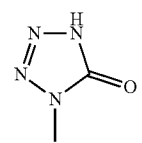 V-51
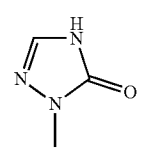 V-52
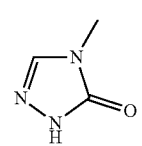 V-53
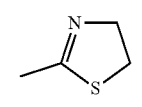 V-54
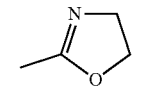 V-55
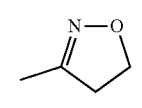 V-56
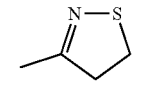 V-57
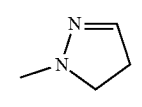 V-58
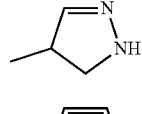 V-59
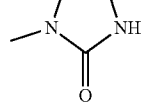 V-60
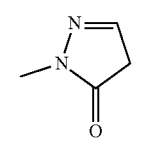 V-61
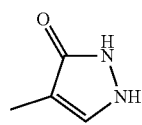 V-62
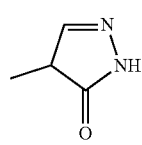 V-63
-continued
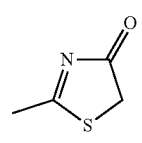 V-64
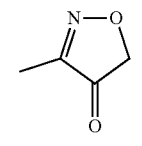 V-65
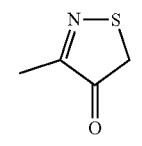 V-66
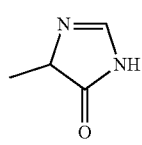 V-67
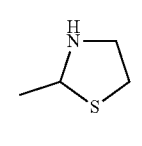 V-68
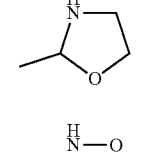 V-69
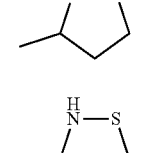 V-70
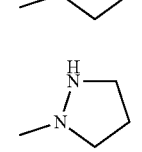 V-71
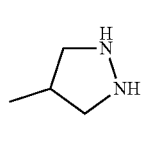 V-72
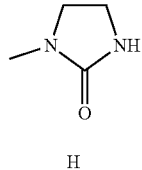 V-73
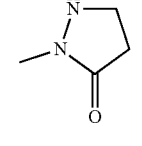 V-74
V-75

| | | |
|---|---|---|
| 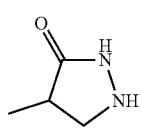 | V-76 | 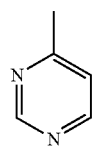 V-87 |
| 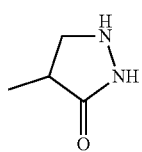 | V-77 | 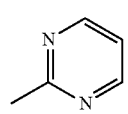 V-88 |
| 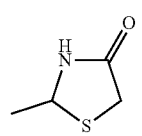 | V-78 | 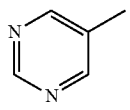 V-89 |
| 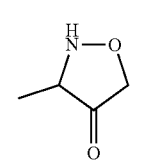 | V-79 | 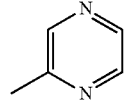 V-90 |
| 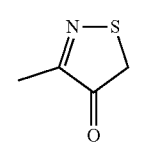 | V-80 | 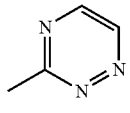 V-91 |
| 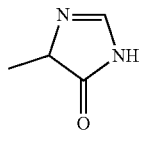 | V-81 | 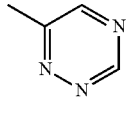 V-92 |
| 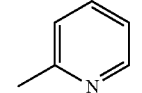 | V-82 | 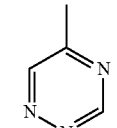 V-93 |
| 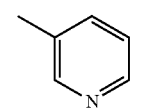 | V-83 | 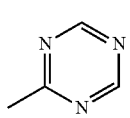 V-94 |
| 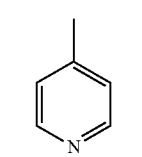 | V-84 | 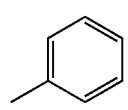 V-95 |
| 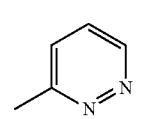 | V-85 | 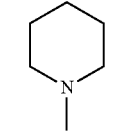 V-96 |
| 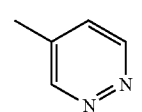 | V-86 | 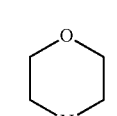 V-97 |
| | | 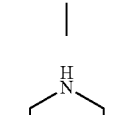 |
| | | 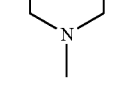 V-98 |

V-99

V-100

V-101

In the particularly preferred embodiment, $R^2$ can be optionally mono- or disubstituted, additionally to V, by identical or different substituents selected from cyano, halogen, $(C_1$-$C_4)$alkyl, $(C_1$-$C_4)$haloalkyl, $(C_1$-$C_4)$alkoxy or $(C_1$-$C_4)$haloalkoxy.

Configuration 4-1

$A^1$ very particularly preferably represents nitrogen or =C($R^4$)—, $R^1$ very particularly preferably represents methyl, ethyl, n-propyl, isopropyl, cyclopropyl, n-butyl, isobutyl, tert-butyl, cyclobutyl, fluoromethyl, difluoromethyl, trifluoromethyl, fluoroethyl, difluoroethyl, trifluoroethyl, tetrafluoroethyl or pentafluoroethyl, $R^2$—V very particularly preferably represents an optionally monosubstituted 5- or 6-membered ring from the series Q-1, Q-2, Q-3, Q-4, Q-5, Q-6, Q-7, Q-8, Q-9, Q-10, Q-12, Q-13, Q-14, Q-15, Q-16, Q-17, Q-24, Q-25, Q-26, Q-27, Q-28, Q-29, Q-30, Q-34, Q-35, Q-41, Q-42, Q-43, Q-44, Q-45, Q-46, Q-47, Q-48, Q-49, Q-50, Q-51, Q-52, Q-55, Q-59, Q-61, Q-66, Q-67, Q-68, Q-69, Q-70, Q-71, Q-72, Q-73, Q-74 or Q-75, where possible substituents are in each case: cyano, fluorine, chlorine, methyl, ethyl, n-propyl, isopropyl, n-butyl, isobutyl, tert-butyl, methoxy or trifluoromethoxy, where V very particularly preferably represents a ring optionally mono- or disubstituted by identical or different substituents selected from cyano, fluorine, chlorine, bromine, methyl, ethyl, n-propyl, isopropyl, n-butyl, isobutyl, tert-butyl, methoxy or trifluoromethoxy, selected from V-1, V-2, V-3, V-4, V-5, V-6, V-7, V-9, V-10, V-16, V-17, V-18, V-19, V-20, V-21, V-24, V-25, V-27, V-28, V-29, V-30, V-35, V-36, V-39, V-42, V-43, V-44, V-45, V-46, V-47, V-48, V-49, V-50, V-51, V-52, V-53, V-60, V-82, V-83, V-84, V-85, V-86, V-87, V-88, V-89, V-90, V-91, V-92, V-93, V-94, V-95, V-96, V-97, V-98, V-99, V-100 or V-101, $R^3$ very particularly preferably represents hydrogen, cyano, halogen, $(C_1$-$C_4)$alkyl, $(C_1$-$C_4)$haloalkyl, $(C_1$-$C_4)$haloalkoxy, $(C_1$-$C_4)$alkylthio, $(C_1$-$C_4)$alkylsulphinyl, $(C_1$-$C_4)$alkylsulphonyl, $(C_1$-$C_4)$haloalkylthio, $(C_1$-$C_4)$haloalkylsulphinyl, $(C_1$-$C_4)$haloalkylsulphonyl or NHCO—$(C_1$-$C_4)$alkyl ($(C_1$-$C_4)$alkylcarbonylamino), X very particularly preferably represents a heteroaromatic 9-membered or 12-membered fused bicyclic or tricyclic ring system from the series H1, H2, H3, H4, H5, H6, H7, H8, H9, H10, H11, H12, H13, H14, H15, H16, H17, H18, H19, or H20, $R^4$ very particularly preferably represents hydrogen, fluorine, chlorine, bromine or cyano, $R^5$ very particularly preferably represents fluorine, chlorine, fluoromethyl, difluoromethyl, trifluoromethyl, fluoroethyl, difluoroethyl, trifluoroethyl, tetrafluoroethyl, pentafluoroethyl, trifluoromethoxy, difluorochloromethoxy, dichlorofluoromethoxy, trifluoromethylthio, trifluoromethylsulphonyl or trifluoromethylsulphinyl, $R^6$ very particularly preferably represents hydrogen, $R^7$ very particularly preferably represents methyl, ethyl, n-propyl, isopropyl, n-butyl, isobutyl, tert-butyl, methoxymethyl or methoxyethyl, n very particularly preferably represents 0, 1 or 2.

In the very particularly preferred embodiment, $R^2$ can be optionally monosubstituted, additionally to V, by cyano, fluorine, chlorine, methyl, ethyl, n-propyl, isopropyl, n-butyl, isobutyl, tert-butyl, methoxy or trifluoromethoxy.

Configuration 4-2

$A^1$, $R^1$, $R^3$, $R^4$, X, $R^5$, $R^6$, $R^7$ and n have the meanings given in configuration 4-1 and $R^2$—V very particularly preferably represents an optionally monosubstituted 5- or 6-membered ring from the series Q-1, Q-2, Q-3, Q-4, Q-5, Q-6, Q-7, Q-8, Q-9, Q-10, Q-12, Q-13, Q-14, Q-15, Q-16, Q-17, Q-24, Q-25, Q-26, Q-27, Q-28, Q-29, Q-30, Q-34, Q-35, Q-41, Q-42, Q-43, Q-44, Q-45, Q-46, Q-47, Q-48, Q-49, Q-50, Q-51, Q-52, Q-55, Q-59, Q-61, Q-66, Q-67, Q-68, Q-69, Q-70, Q-71, Q-72, Q-73, Q-74 or Q-75, where possible substituents are in each case: cyano, fluorine, chlorine, methyl, ethyl, n-propyl, isopropyl, n-butyl, isobutyl, tert-butyl, trifluoromethyl, methoxy or trifluoromethoxy, where V very particularly preferably represents a ring optionally mono- or disubstituted by identical or different substituents selected from cyano, fluorine, chlorine, bromine, methyl, ethyl, n-propyl, isopropyl, n-butyl, isobutyl, tert-butyl, trifluoromethyl, methoxy or trifluoromethoxy, selected from V-1, V-2, V-3, V-4, V-5, V-6, V-7, V-9, V-10, V-16, V-17, V-18, V-19, V-20, V-21, V-24, V-25, V-27, V-28, V-29, V-30, V-35, V-36, V-39, V-42, V-43, V-44, V-45, V-46, V-47, V-48, V-49, V-50, V-51, V-52, V-53, V-60, V-82, V-83, V-84, V-85, V-86, V-87, V-88, V-89, V-90, V-91, V-92, V-93, V-94, V-95, V-96, V-97, V-98, V-99, V-100 or V-101.

In the very particularly preferred embodiment, $R^2$ can be optionally monosubstituted, additionally to V, by cyano, fluorine, chlorine, methyl, ethyl, n-propyl, isopropyl, n-butyl, isobutyl, tert-butyl, trifluoromethyl, methoxy or trifluoromethoxy.

Configuration 5-1

$A^1$ with emphasis represents nitrogen, $R^1$ with emphasis represents ethyl, $R^2$—V with emphasis represents a ring from the series Q-42, Q-50, Q-51, Q-52, Q-59 or Q-61, where V with emphasis represents a ring optionally mono- or disubstituted by identical substituents selected from fluorine, chlorine or bromine from the series V-82 or V-95, $R^3$ with emphasis represents hydrogen, X with emphasis represents a heteroaromatic ring system from the series H20, $R^5$ with emphasis represents trifluoromethyl, $R^6$ with emphasis represents hydrogen,
$R^7$ with emphasis represents methyl,
n with emphasis represents 2.
Configuration 5-2
$A^1$ with emphasis represents nitrogen,
$R^1$ with emphasis represents ethyl,
$R^2$—V with emphasis represents a ring optionally monosubstituted by chlorine or trifluoromethyl from the series Q-12, Q-27, Q-28, Q-42, Q-45, Q-50, Q-51, Q-52, Q-59 or Q-61,
where
V with emphasis represents a ring optionally mono- or disubstituted by identical or different substituents selected from fluorine, chlorine or bromine from the series V-2, V-82, V-83 or V-95,
$R^3$ with emphasis represents hydrogen,
X with emphasis represents a heteroaromatic ring system from the series H1, H2, H15 or H20,
$R^5$ with emphasis represents trifluoromethyl,
$R^6$ with emphasis represents hydrogen,
$R^7$ with emphasis represents methyl,
n with emphasis represents 2.

In the emphasized embodiment, $R^2$ can be optionally monosubstituted, additionally to V, by chlorine or trifluoromethyl.

The substitution at rings Q-1 to Q-80 and also V-1 to V-101 can be by substitution of hydrogen at the carbon atom and/or at the nitrogen atom.

In a preferred embodiment, the invention relates to compounds of the formula (I) where X represents H1 and $R^1$, $R^2$, $R^3$, $R^5$, $R^6$, $R^7$, $A^1$, V, X and n have the meanings given in configuration (3-1) or configuration (3-2) or configuration (4-1) or configuration (4-2) or configuration (5-1) or configuration (5-2).

In a preferred embodiment, the invention relates to compounds of the formula (I) where X represents H2 and $R^1$, $R^2$, $R^3$, $R^5$, $R^6$, $R^7$, $A^1$, V, X and n have the meanings given in configuration (3-1) or configuration (3-2) or configuration (4-1) or configuration (4-2) or configuration (5-1) or configuration (5-2).

In a preferred embodiment, the invention relates to compounds of the formula (I) where X represents H3 and $R^1$, $R^2$, $R^3$, $R^5$, $R^6$, V, X and n have the meanings given in configuration (3-1) or configuration (3-2) or configuration (4-1) or configuration (4-2) or configuration (5-1) or configuration (5-2).

In a preferred embodiment, the invention relates to compounds of the formula (I) where X represents H4 and $R^1$, $R^2$, $R^3$, $R^5$, $R^6$, $A^1$ V, X and n have the meanings given in configuration (3-1) or configuration (3-2) or configuration (4-1) or configuration (4-2) or configuration (5-1) or configuration (5-2).

In a preferred embodiment, the invention relates to compounds of the formula (I) where X represents H5 and $R^1$, $R^2$, $R^3$, $R^5$, $R^6$, $A^1$ V, X and n have the meanings given in configuration (3-1) or configuration (3-2) or configuration (4-1) or configuration (4-2) or configuration (5-1) or configuration (5-2).

In a preferred embodiment, the invention relates to compounds of the formula (I) where X represents H6 and $R^1$, $R^2$, $R^3$, $R^5$, $R^6$, $A^1$ V, X and n have the meanings given in configuration (3-1) or configuration (3-2) or configuration (4-1) or configuration (4-2) or configuration (5-1) or configuration (5-2).

In a preferred embodiment, the invention relates to compounds of the formula (I) where X represents H7 and $R^1$, $R^2$, $R^3$, $R^5$, $R^6$, $A^1$ V, X and n have the meanings given in configuration (3-1) or configuration (3-2) or configuration (4-1) or configuration (4-2) or configuration (5-1) or configuration (5-2).

In a preferred embodiment, the invention relates to compounds of the formula (I) where X represents H8 and $R^1$, $R^2$, $R^3$, $R^5$, $R^6$, $A^1$ V, X and n have the meanings given in configuration (3-1) or configuration (3-2) or configuration (4-1) or configuration (4-2) or configuration (5-1) or configuration (5-2).

In a preferred embodiment, the invention relates to compounds of the formula (I) where X represents H9 and $R^1$, $R^2$, $R^3$, $R^5$, $R^6$, $A^1$ V, X and n have the meanings given in configuration (3-1) or configuration (3-2) or configuration (4-1) or configuration (4-2) or configuration (5-1) or configuration (5-2).

In a preferred embodiment, the invention relates to compounds of the formula (I) where X represents H10 and $R^1$, $R^2$, $R^3$, $R^5$, $R^6$, $A^1$ V, X and n have the meanings given in configuration (3-1) or configuration (3-2) or configuration (4-1) or configuration (4-2) or configuration (5-1) or configuration (5-2).

In a preferred embodiment, the invention relates to compounds of the formula (I) where X represents H11 and $R^1$, $R^2$, $R^3$, $R^5$, $R^6$, $A^1$ V, X and n have the meanings given in configuration (3-1) or configuration (3-2) or configuration (4-1) or configuration (4-2) or configuration (5-1) or configuration (5-2).

In a preferred embodiment, the invention relates to compounds of the formula (I) where X represents H12 and $R^1$, $R^2$, $R^3$, $R^5$, $R^6$, $R^7$, $A^1$, V, X and n have the meanings given in configuration (3-1) or configuration (3-2) or configuration (4-1) or configuration (4-2) or configuration (5-1) or configuration (5-2).

In a preferred embodiment, the invention relates to compounds of the formula (I) where X represents H13 and $R^1$, $R^2$, $R^3$, $R^5$, $R^6$, $A^1$ V, X and n have the meanings given in configuration (3-1) or configuration (3-2) or configuration (4-1) or configuration (4-2) or configuration (5-1) or configuration (5-2).

In a preferred embodiment, the invention relates to compounds of the formula (I) where X represents H14 and $R^1$, $R^2$, $R^3$, $R^5$, $R^6$, $R^7$, $A^1$, V, X and n have the meanings given in configuration (3-1) or configuration (3-2) or configuration (4-1) or configuration (4-2) or configuration (5-1) or configuration (5-2).

In a preferred embodiment, the invention relates to compounds of the formula (I) where X represents H15 and $R^1$, $R^2$, $R^3$, $R^5$, $R^6$, $A^1$ V, X and n have the meanings given in configuration (3-1) or configuration (3-2) or configuration (4-1) or configuration (4-2) or configuration (5-1) or configuration (5-2).

In a preferred embodiment, the invention relates to compounds of the formula (I) where X represents H16 and $R^1$, $R^2$, $R^3$, $R^5$, $R^6$, $A^1$ V, X and n have the meanings given in configuration (3-1) or configuration (3-2) or configuration (4-1) or configuration (4-2) or configuration (5-1) or configuration (5-2).

In a preferred embodiment, the invention relates to compounds of the formula (I) where X represents H17 and $R^1$, $R^2$, $R^3$, $R^5$, $R^6$, $R^7$, $A^1$, V, X and n have the meanings given in configuration (3-1) or configuration (3-2) or configuration (4-1) or configuration (4-2) or configuration (5-1) or configuration (5-2).

In a preferred embodiment, the invention relates to compounds of the formula (I) where X represents H18 and $R^1$, $R^2$, $R^3$, $R^5$, $R^6$, $A^1$ V, X and n have the meanings given in configuration (3-1) or configuration (3-2) or configuration (4-1) or configuration (4-2) or configuration (5-1) or configuration (5-2).

In a preferred embodiment, the invention relates to compounds of the formula (I) where X represents H19 and $R^1$, $R^2$, $R^3$, $R^5$, $R^6$, $R^7$, $A^1$, V, X and n have the meanings given in configuration (3-1) or configuration (3-2) or configuration (4-1) or configuration (4-2) or configuration (5-1) or configuration (5-2).

In a preferred embodiment, the invention relates to compounds of the formula (I) where X represents H20 and $R^1$, $R^2$, $R^3$, $R^5$, $R^6$, $R^7$, $A^1$, V, X and n have the meanings given in configuration (3-1) or configuration (3-2) or configuration (4-1) or configuration (4-2) or configuration (5-1) or configuration (5-2).

In the preferred definitions, unless stated otherwise, halogen is selected from the series consisting of fluorine, chlorine, bromine and iodine, preferably in turn from the series consisting of fluorine, chlorine and bromine.

In the particularly preferred definitions, unless stated otherwise, halogen is selected from the series consisting of fluorine, chlorine, bromine and iodine, preferably in turn from the series consisting of fluorine, chlorine and bromine.

In the context of the present invention, unless defined differently elsewhere, the term "alkyl", either on its own or else in combination with further terms, for example haloalkyl, is understood to mean a radical of a saturated aliphatic hydrocarbon group which has 1 to 12 carbon atoms and may be branched or unbranched. Examples of $C_1$-$C_{12}$-alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl, n-heptyl, n-octyl, n-nonyl, n-decyl, n-undecyl and n-dodecyl. From among these alkyl radicals, particular preference is given to $C_1$-$C_6$-alkyl radicals. Special preference is given to $C_1$-$C_4$-alkyl radicals.

According to the invention, unless defined differently elsewhere, the term "alkenyl", either on its own or else in combination with further terms, is understood to mean a straight-chain or branched $C_2$-$C_{12}$-alkenyl radical which has at least one double bond, for example vinyl, allyl, 1-propenyl, isopropenyl, 1-butenyl, 2-butenyl, 3-butenyl, 1,3-butadienyl, 1-pentenyl, 2-pentenyl, 3-pentenyl, 4-pentenyl, 1,3-pentadienyl, 1-hexenyl, 2-hexenyl, 3-hexenyl, 4-hexenyl, 5-hexenyl and 1,4-hexadienyl. Among these, preference is given to $C_2$-$C_6$-alkenyl radicals and particular preference to $C_2$-$C_4$-alkenyl radicals.

According to the invention, unless defined differently elsewhere, the term "alkynyl", either on its own or else in combination with further terms, is understood to mean a straight-chain or branched $C_2$-$C_{12}$-alkynyl radical which has at least one triple bond, for example ethynyl, 1-propynyl and propargyl. Among these, preference is given to $C_3$-$C_6$-alkynyl radicals and particular preference to $C_3$-$C_4$-alkynyl radicals. The alkynyl radical may also contain at least one double bond.

According to the invention, unless defined differently elsewhere, the term "cycloalkyl", either on its own or else in combination with further terms, is understood to mean a $C_3$-$C_8$-cycloalkyl radical, for example cyclopropyl, cyclobutyl, cyclopentyl, cyclohexyl, cycloheptyl and cyclooctyl. Among these, preference is given to $C_3$-$C_6$-cycloalkyl radicals.

The term "alkoxy", either on its own or else in combination with further terms, for example haloalkoxy, is understood to mean in the present case an O-alkyl radical, where the term "alkyl" is as defined above.

Halogen-substituted radicals, for example haloalkyl, are mono- or polyhalogenated, up to the maximum number of possible substituents. In the case of polyhalogenation, the halogen atoms can be identical or different. In this case, halogen is fluorine, chlorine, bromine or iodine, especially fluorine, chlorine or bromine.

Unless stated otherwise, optionally substituted radicals may be mono- or polysubstituted, where the substituents in the case of polysubstitutions may be the same or different.

The radical definitions or elucidations given above in general terms or within ranges of preference apply to the end products and correspondingly to the starting materials and intermediates. These radical definitions can be combined with one another as desired, i.e. including combinations between the respective ranges of preference.

Preference according to the invention is given to using compounds of the formula (I) which contain a combination of the meanings listed above as being preferred.

Particular preference according to the invention is given to using compounds of the formula (I) which contain a combination of the meanings listed above as being particularly preferred.

Very particular preference according to the invention is given to using compounds of the formula (I) which contain a combination of the meanings listed above as being very particularly preferred.

Most preference according to the invention is given to using compounds of the formula (I) which contain a combination of the meanings listed above as being most preferable.

Depending on the nature of the substituents, the compounds of the formula (I) may be in the form of geometric and/or optically active isomers or corresponding isomer mixtures in different compositions. These stereoisomers are, for example, enantiomers, diastereomers, atropisomers or geometric isomers. The invention therefore encompasses pure stereoisomers and any mixtures of these isomers.

The compounds of the formula (I) according to the invention can be obtained by the processes shown in the following schemes:

Process A

The compounds of the formula (I) in which X represents H1, H2, H4, H5, H6, H7, H8, H9, H14, H19 or H20 can be prepared by known methods, for example analogously to the processes described in WO2009/131237, WO2010/125985, WO2011/043404, WO2011/040629, WO2012/086848, WO2013/018928 or WO2015/000715.

The general process for preparing compounds of the formula (I) in which X is H1, H2, H4, H5, H6, H7, H8, H9, H14, H19 or H20 is described below by reference to Example H2, H5 and H8.

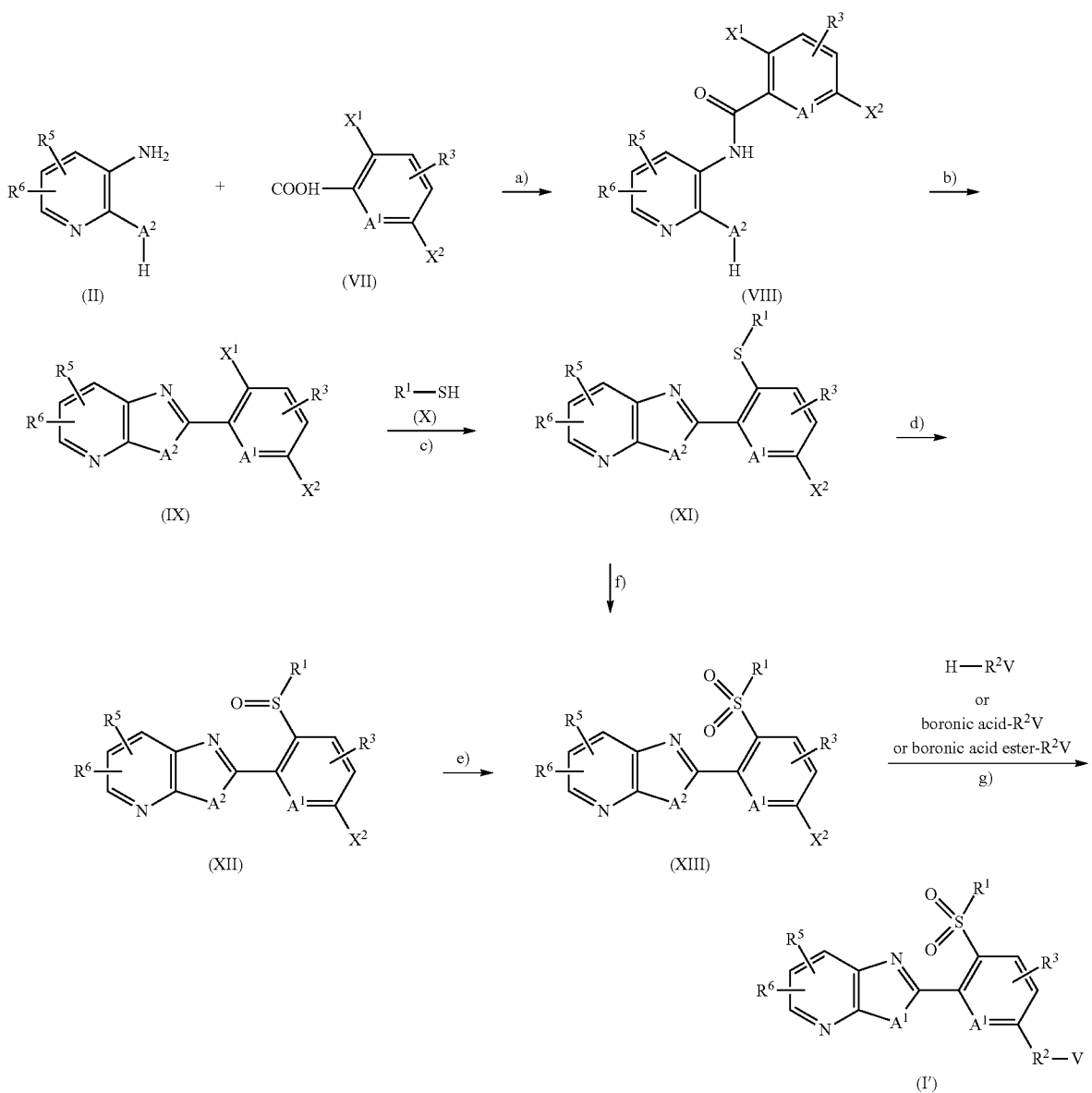

The radicals $R^1$, $R^2$, $R^3$, $R^5$, $R^6$, $A^1$ and V have the meanings described above, $A^2$ represents —N—$R^7$, O or S, where $R^7$ has the meaning described above and $X^1$ and $X^2$ represent halogen.

Step a)

The compounds of the formula (VIII) can be prepared in analogy to the process described in U.S. Pat. No. 5,576,335 by the reaction of compounds of the formula (II) with a carboxylic acid of the formula (VII) in the presence of a condensing agent or a base.

Compounds of the formula (II) are either commercially available or can be prepared by known methods, for example analogously to the processes described in US2003/69257 or WO2006/65703.

Carboxylic acids of the formula (VII) are either commercially available or can be prepared by known methods, for example analogously to the processes described in US2010/234604, WO2012/61926 or Bioorganic and Medicinal Chemistry Letters, 18 (2008), 5023-5026.

The reaction of the compounds of the formula (II) with carboxylic acids of the formula (VII) can be effected neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane; halogenated hydrocarbons, for example dichloromethane, chloroform, carbon tetrachloride, 1,2-dichloroethane or chlorobenzene; nitriles, for example acetonitrile or propionitrile; aromatic hydrocarbons, for example toluene or xylene; aprotic polar solvents, for example N,N-dimethylformamide or N-methylpyrrolidone, or nitrogen-containing compounds, for example pyridine.

Suitable condensing agents are, for example, carbodiimides such as 1-(3-dimethylaminopropyl)-3-ethylcarbodiimide hydrochloride (EDCI) or 1,3-dicyclohexylcarbodiimide.

Suitable bases are inorganic bases which are typically used in such reactions. Preference is given to using bases selected by way of example from the group consisting of acetates, phosphates, carbonates and hydrogencarbonates of alkali metals or alkaline earth metals. Particular preference is given here to sodium acetate, sodium phosphate, potassium phosphate, caesium carbonate, sodium carbonate, potassium carbonate, sodium hydrogencarbonate, potassium hydrogencarbonate.

The reaction can be carried out under reduced pressure, at atmospheric pressure or under elevated pressure and at temperatures of 0° C. to 180° C.; with preference, the reaction is carried out at atmospheric pressure and temperatures of 20 to 140° C.

Step b)

The compounds of the formula (IX) can be prepared by condensing the compounds of the formula (VIII), for example analogously to the processes described in WO2012/86848.

The conversion to compounds of the formula (IX) can be effected neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; halogenated hydrocarbons, for example dichloromethane, chloroform, carbon tetrachloride, 1,2-dichloroethane or chlorobenzene; nitriles, for example acetonitrile or propionitrile; aromatic hydrocarbons, for example toluene or xylene; aprotic polar solvents, for example N,N-dimethylformamide or N-methylpyrrolidone, or nitrogen compounds, for example pyridine.

The reaction can be carried out in the presence of a condensing agent, an acid, a base or a chlorinating agent.

Examples of suitable condensing agents are carbodiimides such as 1-(3-dimethylaminopropyl)-3-ethylcarbodiimide hydrochloride (EDCI) or 1,3-dicyclohexylcarbodiimide; anhydrides such as acetic anhydride, trifluoroacetic anhydride; a mixture of triphenylphosphine, a base and carbon tetrachloride, or a mixture of triphenylphosphine and an azo diester, for example diethylazodicarboxylic acid.

Examples of suitable acids which can be used in the reaction described are sulphonic acids such as para-toluenesulphonic acid; carboxylic acids such as acetic acid, or polyphosphoric acids.

Examples of suitable bases are nitrogen heterocycles such as pyridine, picoline, 2,6-lutidine, 1,8-diazabicyclo[5.4.0]-7-undecene (DBU); tertiary amines such as triethylamine and N,N-diisopropylethylamine; inorganic bases such as potassium phosphate, potassium carbonate and sodium hydride.

An example of a suitable chlorinating agent is phosphorus oxychloride.

The reaction can be carried out under reduced pressure, atmospheric pressure or under elevated pressure and at temperatures of 0° C. to 200° C.

Step c)

The compounds of the formula (XI) can be prepared by reacting the compounds of the formula (IX) with the compounds of the formula (X) in the presence of a base.

Mercaptan derivatives of the formula (X), for example methyl mercaptan, ethyl mercaptan or isopropyl mercaptan, are either commercially available or can be prepared by known methods, for example analogously to the processes described in US2006/25633, US2006/111591, U.S. Pat. No. 2,820,062, Chemical Communications, 13 (2000), 1163-1164 or Journal of the American Chemical Society, 44 (1922), p. 1329.

The conversion to compounds of the formula (XI) can be effected neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; nitriles, for example acetonitrile or propionitrile; aromatic hydrocarbons, for example toluene or xylene; aprotic polar solvents, for example N,N-dimethylformamide, N-methylpyrrolidone or dimethyl sulphoxide.

Examples of suitable bases are inorganic bases from the group consisting of acetates, phosphates and carbonates of alkali metals or alkaline earth metals. Preference is given here to caesium carbonate, sodium carbonate and potassium carbonate. Further suitable bases are alkali metal hydrides, for example sodium hydride.

The reaction can be carried out under reduced pressure, at atmospheric pressure or under elevated pressure, and at temperatures of 0° C. to 200° C.

Step d)

The compounds of the formula (XII) can be prepared by oxidizing the compounds of the formula (XI). The oxidation is generally carried out in a solvent selected from customary solvents which are inert under the prevailing reaction conditions. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide, meta-chloroperbenzoic acid or sodium periodate.

The reaction can be carried out under reduced pressure, at atmospheric pressure or under elevated pressure, and at temperatures of from −20° C. to 120° C.

Step e)

The compounds of the formula (XIII) can be prepared by oxidizing the compounds of the formula (XII). The oxidation is generally carried out in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide and meta-chloroperbenzoic acid.

The reaction can be carried out under reduced pressure, at atmospheric pressure or under elevated pressure, and at temperatures of from −20° C. to 120° C.

Step f)

The compounds of the formula (XIII) can also be prepared in a one-step process by oxidizing the compounds of the formula (XI). The oxidation is generally carried out in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide and meta-chloroperbenzoic acid.

The reaction can be carried out under reduced pressure, at atmospheric pressure or under elevated pressure, and at temperatures of from −20° C. to 120° C.

Step g)

The preparation of compounds of the formula (I') in which $R^2$—V represents a bi-cycle attached to the remainder of the molecule via nitrogen can take place for example from compounds of the formula (XIII) for which $X^2$ preferably represents halogen from the series chlorine or bromine, by methods known in the literature (see, for example, Journal of Organic Chemistry (2010), 69, 5578), e.g. in the presence of copper(I) iodide and basic reaction auxiliaries, for example trans-N,N'-dimethylcyclohexane-1,2-diamine and potassium carbonate, in a suitable solvent or diluent.

The required compounds of the formula H—$R^2$V are either commercially available or can be prepared by known methods.

Useful solvents or diluents include all inert organic solvents, for example aliphatic or aromatic hydrocarbons. Preference is given to using toluene. Furthermore, the coupling can take place from compounds of the formula (XIII), for which $X^2$ preferably represents halogen from the series fluorine, chlorine or bromine, without metal catalysis in the presence of a suitable base such as, for example, potassium carbonate or caesium carbonate in a suitable solvent or diluent. Useful solvents or diluents include all inert organic solvents, for example aliphatic or aromatic hydrocarbons. Preference is given here to using acetonitrile or dimethylformamide.

Compounds of the formula (I') for which $R^2$—V represents a bi-cycle attached to the remainder of the molecule via carbon can be prepared for example from compounds of the formula (XIII), for which $X^2$ preferably represents halogen from the series chlorine or bromine, by generally known methods (cf. *Chem. Rev.* 1995, 95, 2457-2483; *Tetrahedron* 2002, 58, 9633-9695; *Metal-Catalyzed Cross-Coupling Reactions* (Eds.: A. de Meijere, F. Diederich), 2nd ed., Wiley-VCH, Weinheim, 2004).

For example, compounds of the formula (XIII) in which $X^2$ preferably represents chlorine or bromine can be reacted with suitable arylboronic acids or esters thereof by known methods (cf. WO2010071819) in the presence of suitable catalysts from the series of the transition metal salts to give compounds of the formula (I'). Examples of preferred coupling catalysts include palladium catalysts such as [1,1'-bis(diphenylphosphino)ferrocene]dichloropalladium(II) or tetrakis(triphenylphosphine)palladium. Suitable basic reaction auxiliaries used to conduct the processes are preferably carbonates of sodium or potassium.

Some of the (hetero)arylboronic acids or (hetero)arylboronic esters required are known and/or commercially available, or they can be prepared by generally known methods (cf. *Boronic Acids* (eds.: D. G. Hall), $2^{nd}$ ed., Wiley-VCH, Weinheim, 2011).

The reaction according to step g) can also take place starting from compounds of the formulae (XI) or (XII).

Process B

The general process for preparing compounds of the formula (I) in which X is H1, H2, H4, H5, H6, H7, H8, H9, H14, H19 or H20 is described below by reference to Example H2, H5 and H8.

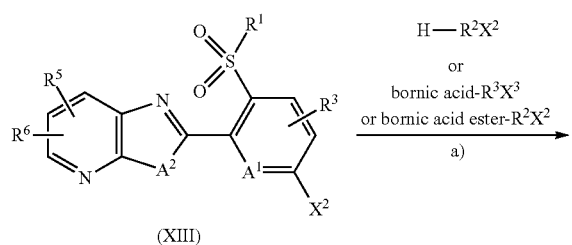

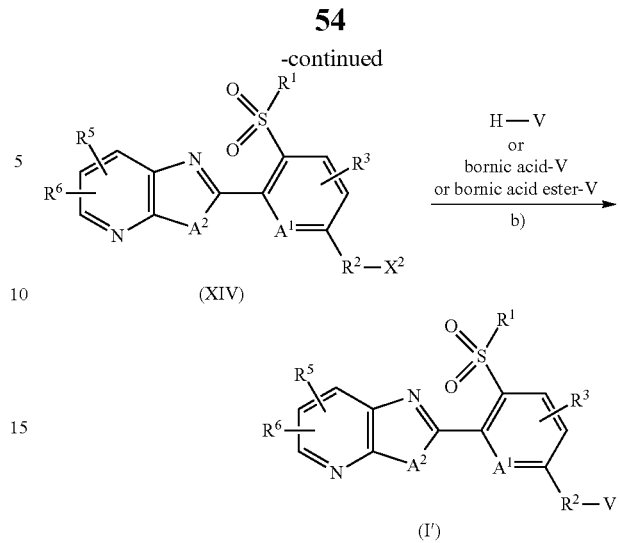

The radicals $R^1$, $R^2$, $R^3$, $R^5$, $R^6$, $A^1$ and V have the meanings described above, $A^2$ represents —N—$R^7$, O or S, where $R^7$ has the meaning described above and $X^1$ and $X^2$ represent halogen.

Step a)

The preparation of compounds of the formula (XIV) in which $R^2$—$X^2$ represents a ring attached to the remainder of the molecule via nitrogen can take place for example from compounds of the formula (XIII) for which $X^1$ is preferably halogen from the series chlorine or bromine, by methods known in the literature (see, for example, Journal of Organic Chemistry (2010), 69, 5578), e.g. in the presence of copper (I) iodide and basic reaction auxiliaries, for example trans-N,N'-dimethylcyclohexane-1,2-diamine and potassium carbonate, in a suitable solvent or diluent. Useful solvents or diluents include all inert organic solvents, for example aliphatic or aromatic hydrocarbons. Preference is given to using toluene. Furthermore, the coupling can take place from compounds of the formula (XIII), for which $X^1$ preferably represents halogen from the series fluorine, chlorine or bromine, without metal catalysis in the presence of a suitable base such as, for example, potassium carbonate or caesium carbonate in a suitable solvent or diluent. Useful solvents or diluents include all inert organic solvents, for example aliphatic or aromatic hydrocarbons. Preference is given here to using acetonitrile or dimethylformamide.

The required compounds of the formula H—$R^2X^2$ are either commercially available or can be prepared by known methods.

Compounds of the formula (XIV) for which $R^2$—$X^2$ represents a ring attached to the remainder of the molecule via carbon can be prepared for example from compounds of the formula (XIII), for which $X^1$ preferably represents halogen from the series chlorine or bromine, by generally known methods (cf. *Chem. Rev.* 1995, 95, 2457-2483; *Tetrahedron* 2002, 58, 9633-9695; *Metal-Catalyzed Cross-Coupling Reactions* (Eds.: A. de Meijere, F. Diederich), 2nd ed., Wiley-VCH, Weinheim, 2004).

For example, compounds of the formula (XIII) in which $X^1$ preferably represents chlorine or bromine can be reacted with suitable arylboronic acids or esters thereof by known methods (cf. WO2010071819) in the presence of suitable catalysts from the series of the transition metal salts to give compounds of the formula (XIV). Examples of preferred coupling catalysts include palladium catalysts such as [1,1'-bis(diphenylphosphino)ferrocene]dichloropalladium(II) or tetrakis(triphenylphosphine)palladium. Suitable basic reaction auxiliaries used to conduct the processes are preferably carbonates of sodium or potassium.

Some of the (hetero)arylboronic acids or (hetero)arylboronic esters required are known and/or commercially available, or they can be prepared by generally known methods (cf. *Boronic Acids* (eds.: D. G. Hall), $2^{nd}$ ed., Wiley-VCH, Weinheim, 2011).

Step b)

The preparation of compounds of the formula (I') in which $R^2$—V represents a bi-cycle attached to the remainder of the molecule via nitrogen can take place for example from compounds of the formula (XIV) for which $X^2$ preferably represents halogen from the series chlorine or bromine, by methods known in the literature (see, for example, Journal of Organic Chemistry (2010), 69, 5578), e.g. in the presence of copper(I) iodide and basic reaction auxiliaries, for example trans-N,N'-dimethylcyclohexane-1,2-diamine and potassium carbonate, in a suitable solvent or diluent. Useful solvents or diluents include all inert organic solvents, for example aliphatic or aromatic hydrocarbons. Preference is given to using toluene. Furthermore, the coupling can take place from compounds of the formula (XIV), for which $X^2$ preferably represents halogen from the series fluorine, chlorine or bromine, without metal catalysis in the presence of a suitable base such as, for example, potassium carbonate or caesium carbonate in a suitable solvent or diluent. Useful solvents or diluents include all inert organic solvents, for example aliphatic or aromatic hydrocarbons. Preference is given here to using acetonitrile or dimethylformamide.

The required compounds of the formula H—V are either commercially available or can be prepared by known methods.

Compounds of the formula (I') for which $R^2$—V represents a bi-cycle attached to the remainder of the molecule via carbon can be prepared for example from compounds of the formula (XIV), for which $X^2$ preferably represents halogen from the series chlorine or bromine, by generally known methods (cf. *Chem. Rev.* 1995, 95, 2457-2483; *Tetrahedron* 2002, 58, 9633-9695; *Metal-Catalyzed Cross-Coupling Reactions* (Eds.: A. de Meijere, F. Diederich), 2nd ed., Wiley-VCH, Weinheim, 2004).

For example, compounds of the formula (XIV) in which $X^2$ preferably represents chlorine or bromine can be reacted with suitable arylboronic acids or esters thereof by known methods (cf. WO2010071819) in the presence of suitable catalysts from the series of the transition metal salts to give compounds of the formula (I'). Examples of preferred coupling catalysts include palladium catalysts such as [1,1'-bis(diphenylphosphino)ferrocene]dichloropalladium(II) or tetrakis(triphenylphosphine)palladium. Suitable basic reaction auxiliaries used to conduct the processes are preferably carbonates of sodium or potassium.

Some of the (hetero)arylboronic acids or (hetero)arylboronic esters required are known and/or commercially available, or they can be prepared by generally known methods (cf. *Boronic Acids* (eds.: D. G. Hall), $2^{nd}$ ed., Wiley-VCH, Weinheim, 2011).

Process C

The compounds of the formula (I) in which X represents H10, H11, H15 or H16 can be prepared by known methods, for example analogously to the processes described in US2009/203705, US2012/258951, WO2013/3298 or J. Med. Chem. 31, (1988) 1590-1595.

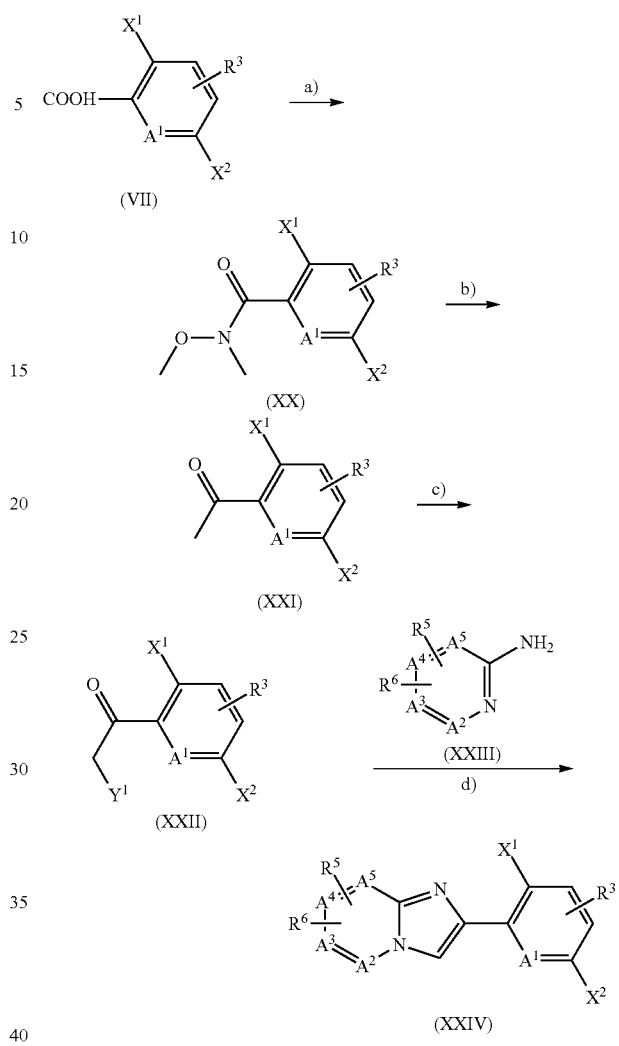

The radicals $A^1$, $R^3$, $R^5$ and $R^6$ have the meanings described above. $X^1$, $X^2$ and $Y^1$ represent halogen. $A^2$, $A^3$, $A^4$ and $A^5$ independently of one another represent CH or N (where $A^2$, $A^3$, $A^4$ and $A^5$ do not simultaneously represent N).

Step a)

Carboxylic acids of the formula (VII) are converted analogously to the process described in WO2011/75643 or EP-A-2671582 in the presence of O,N-dimethylhydroxylamine hydrochloride into Weinreb amides of the formula (XX).

Carboxylic acids of the formula (VII) are either commercially available or can be prepared by known methods, for example analogously to the processes described in US2010/234604, WO2012/61926 or Bioorganic and Medicinal Chemistry Letters, 18 (2008), 5023-5026.

Step b, c)

Compounds of the formula (XX) can then be converted by known methods, for example analogously to the process described in WO2011/75643, using a Grignard reagent such as, for example, methylmagnesium bromide into ketones of the formula (XXI). Subsequent halogenation analogous to the known methods described for example in US2012/302573 or in Eur. J. Org. Chem. 2013, 1551-1557 affords compounds of the formula (XXII).

Step d)

The compounds of the formula (XXIV) can be prepared by cyclizing the compounds of the formula (XXII) with amines of the formula (XXIII). The cyclization is carried out, for example, in ethanol, acetonitrile, chloroform, tert-Butanol or N,N-dimethylformamide according to known methods analogously, for example, to the processes described in WO2005/66177, WO2012/88411, WO2013/3298, US2009/203705, US2012/258951, WO2012/168733, WO2014/187762 or J. Med. Chem. 31 (1988) 1590-1595.

The compounds of the formula (XXIII) are commercially available.

The further conversion of compounds of the formula (XXIV) to compounds of the formula (I) is carried out analogously to processes A to B.

Process D

The compounds of the formula (I) in which X represents H17 can be prepared by known methods, for example analogously to the processes described in WO2014/142292.

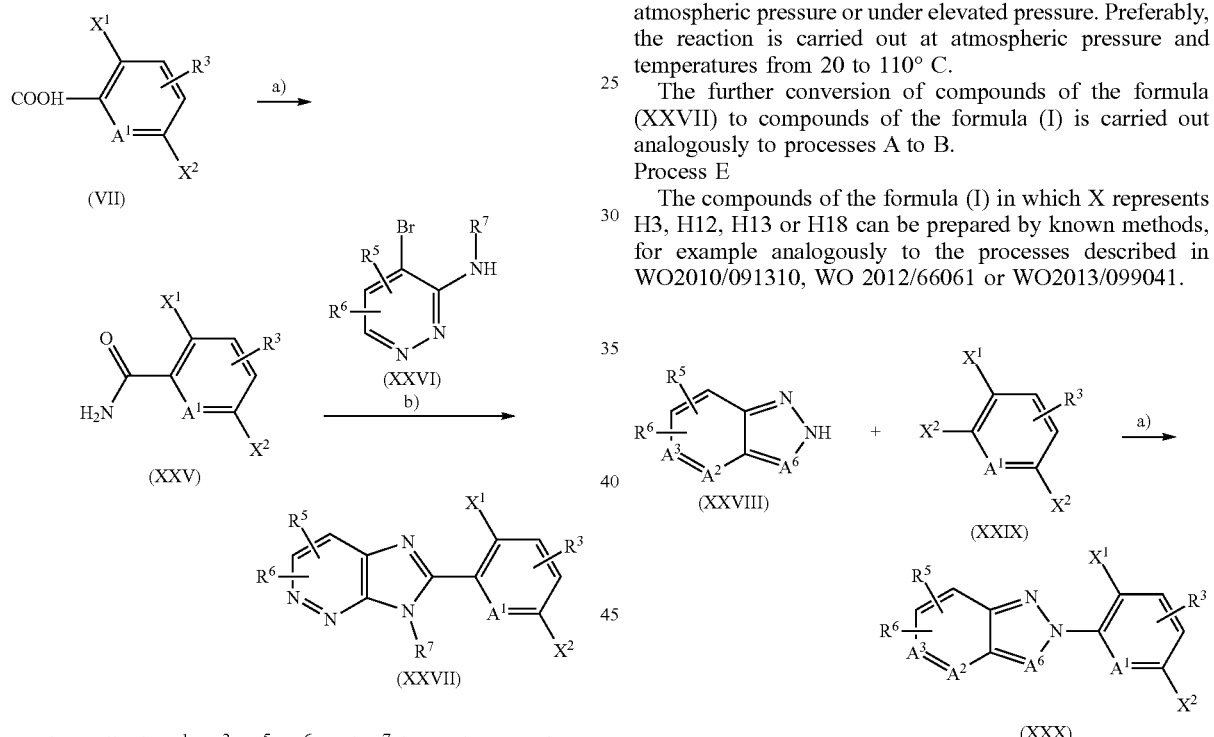

(VII)

(XXV)

(XXVI)

(XXVII)

The radicals $A^1$, $R^3$, $R^5$, $R^6$ and $R^7$ have the meanings described above. $X^1$ and $X^2$ represent halogen.

Step a)

The compounds of the formula (XXV) can be prepared in analogy to the process described in U.S. Pat. No. 5,374,646 or Bioorganic and Medicinal Chemistry Letters 2003, 13, 1093-1096 by reacting compounds of the formula (VII) with an ammonia source in the presence of a condensing agent.

Carboxylic acids of the formula (VII) are either commercially available or can be prepared by known methods, for example analogously to the processes described in US2010/234604, WO2012/61926 or Bioorganic and Medicinal Chemistry Letters, 18 (2008), 5023-5026.

The reaction of the compounds of the formula (VII) with the ammonia source is preferably carried out in a solvent selected from customary solvents which are inert under the prevailing reaction conditions. Preference is given to ethers such as, for example, dioxane or tetrahydrofuran.

A suitable condensing agent is, for example, carbonyldiimidazole.

The reaction can be carried out under reduced pressure, at atmospheric pressure or under elevated pressure. Preferably, the reaction is carried out at atmospheric pressure and temperatures from 20 to 70° C.

Step b)

The compounds of the formula (XXVII) can be prepared in analogy to the process described in WO2014/142292 by reacting compounds of the formula (XXV) with compounds of the formula (XXVI) in the presence of a palladium catalyst in basic media.

Compounds of the formula (XXVI) can be prepared, for example, analogously to the processes described in WO2014/142292. Suitable for use as palladium catalyst may be, for example, [1,1'-bis-(diphenylphosphino)ferrocene]dichloropalladium(II). Frequently, the bases used are inorganic bases such as potassium tert-butoxide.

The reaction is carried out in a solvent. Frequently, use is made of toluene.

The reaction can be carried out under reduced pressure, at atmospheric pressure or under elevated pressure. Preferably, the reaction is carried out at atmospheric pressure and temperatures from 20 to 110° C.

The further conversion of compounds of the formula (XXVII) to compounds of the formula (I) is carried out analogously to processes A to B.

Process E

The compounds of the formula (I) in which X represents H3, H12, H13 or H18 can be prepared by known methods, for example analogously to the processes described in WO2010/091310, WO 2012/66061 or WO2013/099041.

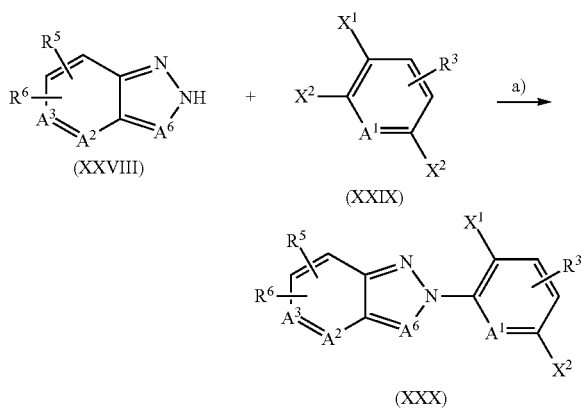

(XXVIII)

(XXIX)

(XXX)

The radicals $A^1$, $R^3$, $R^5$ and $R^6$ have the meanings described above. $A^2$, $A^3$ and $A^6$ independently of one another represent CH or N (where $A^2$ and $A^3$ cannot simultaneously represent N). $X^1$, $X^2$ and $X^3$ represent halogen.

Step a)

The compounds of the formula (XXX) can be prepared by reacting compounds of the formula (XXVIII) with compounds of the formula (XXIX) by means of palladium-catalysed N-arylation, e.g. analogously to the processes described in Angewandte Chemie Int. Ed. 2011, 50, 8944-8947.

Compounds of the formula (XXVIII) are either commercially available or can be prepared by known methods, for example analogously to the processes described in WO2005/100353, WO 2012/66061 or in European Journal of Medicinal Chemistry 2010, 45, 2214-2222.

Compounds of the formula (XXIX) are either commercially available or can be prepared by known methods, for example analogously to the processes described in WO2013/43518, EP-A-2168965 or in Journal of Medicinal Chemistry 2003, 46, 1449-1455.

The further conversion of compounds of the formula (XXX) to compounds of the formula (I) is carried out analogously to processes A to B.

Process F

The compounds of the formula (I) in which X represents H1, H2, H4, H5, H6, H7, H8, H9, H10, H11, H14, H15, H16, H17, H19 or H20, can alternatively be prepared according to the following method. The method is described below by reference to Example H10, H11, H15 and H16.

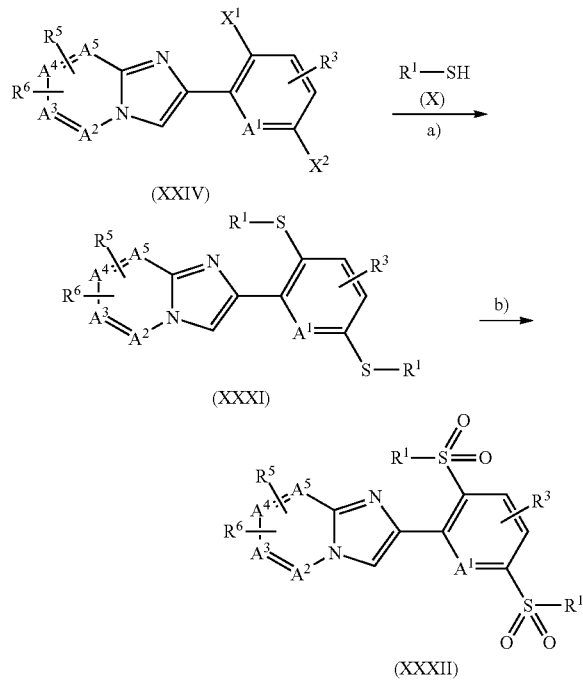

The radicals $A^1$, $R^3$, $R^5$ and $R^6$ have the meanings described above. $X^1$ and $X^2$ represent halogen. $A^2$, $A^3$, $A^4$ and $A^5$ independently of one another represent CH or N (where $A^2$, $A^3$, $A^4$ and $A^5$ do not simultaneously represent N).

Step a)

Analogously to process A, step c), the disulphide of the formula (XXXI) can also be formed instead of a sulphide from compounds of the formula (XXIV).

Step b)

The disulphide of the formula (XXXI) can be converted analogously to process A step f) to the disulphone of the formula (XXXII).

The further conversion of compounds of the formula (XXXII) to compounds of the formula (I) in which $R^2$—V represents a bi-cycle attached to the remainder of the molecule via nitrogen takes place analogously to process A, step g) in the presence of a suitable base such as, for example, potassium carbonate or caesium carbonate in a suitable solvent or diluent such as, for example, acetonitrile or dimethylformamide.

Methods and Uses

The invention also relates to methods for controlling animal pests, in which compounds of the formula (I) are allowed to act on animal pests and/or their habitat. The control of the animal pests is preferably carried out in agriculture and forestry, and in material protection. Preferably excluded from this are methods for the surgical or therapeutic treatment of the human or animal body and diagnostic methods carried out on the human or animal body.

The invention further relates to the use of the compounds of the formula (I) as pesticides, especially crop protection agents.

In the context of the present application, the term "pesticide" also always encompasses the term "crop protection agent".

The compounds of the formula (I), given good plant tolerance, favourable homeotherm toxicity and good environmental compatibility, are suitable for protecting plants and plant organs against biotic and abiotic stress factors, for increasing harvest yields, for improving the quality of the harvested material and for controlling animal pests, especially insects, arachnids, helminths, nematodes and molluscs, which are encountered in agriculture, in horticulture, in animal husbandry, in aquatic cultures, in forests, in gardens and leisure facilities, in the protection of stored products and of materials, and in the hygiene sector.

In the context of the present patent application, the term "hygiene" is understood as meaning the entirety of all measures, processes and procedures whose aim it is to prevent disorders—in particular infective diseases—and to serve to keep humans, animals and/or the environment healthy and/or to maintain cleanliness. According to the invention, this includes in particular measures for cleaning, disinfecting and sterilizing, for example, textiles or hard surfaces, mainly made of glass, wood, concrete, porcelain, ceramic, plastic or else made of metal(s), and keeping them clean of hygiene pests and/or their faeces. Excluded according to the invention are in this respect again processes for the surgical or therapeutic treatment of the human or animal body and diagnostic processes undertaken on the human or animal body.

The term "hygiene sector" thus includes all areas, technical fields and commercial utilizations in which such hygiene measures, processes and procedures are of importance, for example hygiene in kitchens, bakeries, airports, baths, swimming pools, shopping centres, hotels, hospitals, stables, etc.

Accordingly, the term "hygiene pest" is understood as meaning one or more animal pests whose presence in the hygiene sector is problematic, in particular for health reasons. Accordingly, the main aim is to minimize or prevent hygiene pests or contact therewith in the hygiene sector. This can be effected, in particular, by using a pesticide, where the agent can be employed both prophylactically and only in the case of infestation to control the pest. It is also possible to use agents which act by avoiding or reducing contact with the pest. Hygiene pests are, for example, the organisms mentioned below.

Thus, the term "hygiene protection" includes all actions which serve to maintain and/or improve such hygiene measures, processes and procedures.

The compounds of the formula (I) can preferably be used as pesticides. They are active against normally sensitive and resistant species and also against all or some stages of development. The abovementioned pests include:

pests from the phylum of the Arthropoda, especially from the class of the Arachnida, for example *Acarus* spp., for example *Acarus siro, Aceria kuko, Aceria sheldoni, Aculops* spp., *Aculus* spp., for example *Aculus fockeui, Aculus*

*schlechtendali, Amblyomma* spp., *Amphitetranychus viennensis, Argas* spp., *Boophilus* spp., *Brevipalpus* spp., for example *Brevipalpus phoenicis, Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., for example *Eotetranychus hicoriae, Epitrimerus pyri, Eutetranychus* spp., for example *Eutetranychus banksi, Eriophyes* spp., for example *Eriophyes pyri, Glycyphagus domesticus, Halotydeus destructor, Hemitarsonemus* spp., for example *Hemitarsonemus latus* (=*Polyphagotarsonemus latus*), *Hyalomma* spp., *Ixodes* spp., *Latrodectus* spp., *Loxosceles* spp., *Neutrombicula autumnalis, Nuphersa* spp., *Oligonychus* spp., for example *Oligonychus coffeae, Oligonychus coniferarum, Oligonychus ilicis, Oligonychus indicus, Oligonychus mangiferus, Oligonychus pratensis, Oligonychus punicae, Oligonychus yothersi, Ornithodorus* spp., *Ornithonyssus* spp., *Panonychus* spp., for example *Panonychus citri* (=*Metatetranychus citri*), *Panonychus ulmi* (=*Metatetranychus ulmi*), *Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., for example *Tarsonemus confusus, Tarsonemus pallidus, Tetranychus* spp., for example *Tetranychus canadensis, Tetranychus cinnabarinus, Tetranychus turkestani, Tetranychus urticae, Trombicula alfreddugesi, Vaejovis* spp., *Vasates lycopersici;* from the class of the Chilopoda, for example *Geophilus* spp., *Scutigera* spp.;

from the order or the class of the Collembola, for example *Onychiurus armatus; Sminthurus viridis;* from the class of the Diplopoda, for example *Blaniulus guttulatus;* from the class of the Insecta, for example from the order of the Blattodea, for example *Blatta orientalis, Blattella asahinai, Blattella germanica, Leucophaea maderae, Loboptera decipiens, Neostylopyga rhombifolia, Panchlora* spp., *Parcoblatta* spp., *Periplaneta* spp., for example *Periplaneta americana, Periplaneta australasiae, Pycnoscelus surinamensis, Supella longipalpa;* from the order of the Coleoptera for example *Acalymma vittatum, Acanthoscelides obtectus, Adoretus* spp., *Aethina tumida, Agelastica alni, Agriotes* spp., for example *Agriotes linneatus, Agriotes mancus, Alphitobius diaperinus, Amphimallon solstitialis, Anobium punctatum, Anoplophora* spp., *Anthonomus* spp., for example *Anthonomus grandis, Anthrenus* spp., *Apion* spp., *Apogonia* spp., *Atomaria* spp., for example *Atomaria linearis, Attagenus* spp., *Baris caerulescens, Bruchidius obtectus, Bruchus* spp., for example *Bruchus pisorum, Bruchus rufimanus, Cassida* spp., *Cerotoma trifurcata, Ceutorrhynchus* spp., for example *Ceutorrhynchus assimilis, Ceutorrhynchus quadridens, Ceutorrhynchus rapae, Chaetocnema* spp., for example *Chaetocnema confinis, Chaetocnema denticulata, Chaetocnema ectypa, Cleonus mendicus, Conoderus* spp., *Cosmopolites* spp., for example *Cosmopolites sordidus, Costelytra zealandica, Ctenicera* spp., *Curculio* spp., for example *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus furnissi, Dermestes* spp., *Diabrotica* spp., for example *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloboderus* spp., *Epicaerus* spp., *Epilachna* spp., for example *Epilachna borealis, Epilachna varivestis, Epitrix* spp., for example *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., for example *Hypothenemus hampei, Hypothenemus obscurus, Hypothenemus pubescens, Lachnosterna consanguinea, Lasioderma serricorne, Latheticus oryzae, Lathridius* spp., *Lema* spp., *Leptinotarsa decemlineata, Leucoptera* spp., for example *Leucoptera coffeella, Lissorhoptrus oryzophilus, Listronotus* (=*Hyperodes*) spp., *Lixus* spp., *Luperodes* spp., *Luperomorpha xanthodera, Lyctus* spp., *Megascelis* spp., *Melanotus* spp., for example *Melanotus longulus oregonensis, Meligethes aeneus, Melolontha* spp., for example *Melolontha melolontha, Migdolus* spp., *Monochamus* spp., *Naupactus xanthographus, Necrobia* spp., *Neogalerucella* spp., *Niptus hololeucus, Oryctes rhinoceros, Oryzaephilus surinamensis, Oryzaphagus oryzae, Otiorhynchus* spp., for example *Otiorhynchus cribricollis, Otiorhynchus ligustici, Otiorhynchus ovatus, Otiorhynchus rugosostriarus, Otiorhynchus sulcatus, Oulema* spp., for example *Oulema melanopus, Oulema oryzae, Oxycetonia jucunda, Phaedon cochleariae, Phyllophaga* spp., *Phyllophaga helleri, Phyllotreta* spp., for example *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., for example *Psylliodes affinis, Psylliodes chrysocephala, Psylliodes punctulata, Ptinus* spp., *Rhizobius ventralis, Rhizopertha dominica, Rhynchophorus* spp., *Rhynchophorus ferrugineus, Rhynchophorus palmarum, Sinoxylon perforans, Sitophilus* spp., for example *Sitophilus granarius, Sitophilus linearis, Sitophilus oryzae, Sitophilus zeamais, Sphenophorus* spp., *Stegobium paniceum, Sternechus* spp., for example *Sternechus paludatus, Symphyletes* spp., *Tanymecus* spp., for example *Tanymecus dilaticollis, Tanymecus indicus, Tanymecus palliatus, Tenebrio molitor, Tenebrioides mauretanicus, Tribolium* spp., for example *Tribolium audax, Tribolium castaneum, Tribolium confusum, Trogoderma* spp., *Tychius* spp., *Xylotrechus* spp., *Zabrus* spp., for example *Zabrus tenebrioides;* from the order of the Dermaptera, for example *Anisolabis maritime, Forficula auricularia, Labidura riparia;* from the order of the Diptera for example *Aedes* spp., for example *Aedes aegypti, Aedes albopictus, Aedes sticticus, Aedes vexans, Agromyza* spp., for example *Agromyza frontella, Agromyza parvicornis, Anastrepha* spp., *Anopheles* spp., for example *Anopheles quadrimaculatus, Anopheles gambiae, Asphondylia* spp., *Bactrocera* spp., for example *Bactrocera cucurbitae, Bactrocera dorsalis, Bactrocera oleae, Bibio hortulanus, Calliphora erythrocephala, Calliphora vicina, Ceratitis capitata, Chironomus* spp., *Chrysomya* spp., *Chrysops* spp., *Chrysozona pluvialis, Cochliomya* spp., *Contarinia* spp., for example *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., for example *Culex pipiens, Culex quinquefasciatus, Culicoides* spp., *Culiseta* spp., *Cuterebra* spp., *Dacus oleae, Dasineura* spp., for example *Dasineura brassicae, Delia* spp., for example *Delia antiqua, Delia coarctata, Delia florilega, Delia platura, Delia radicum, Dermatobia hominis, Drosophila* spp., for example *Drosphila melanogaster, Drosophila suzukii, Echinocnemus* spp., *Euleia heraclei, Fannia* spp., *Gasterophilus* spp., *Glossina* spp., *Haematopota* spp., Hydrellia spp., Hydrellia griseola, Hylemya spp., Hippobosca spp., Hypoderma spp., Liriomyza spp., for example Liriomyza brassicae, Liriomyza huidobrensis, Liriomyza sativae, Lucilia spp., for example Lucilia cuprina, Lutzomyia spp., Mansonia spp., Musca spp., for example Musca domestica, Musca domestica vicina, Oestrus spp., Oscinella frit, Paratanytarsus spp., Paralauterborniella subcincta, Pegomya oder Pegomyia spp., for example Pegomya betae, Pegomya hyoscyami, Pegomya rubivora, Phlebotomus spp., Phorbia spp., Phormia spp., Piophila casei, Platyparea poeciloptera, Prodiplosis spp., Psila rosae, Rhagoletis spp., for example Rhagoletis cingulata, Rhagoletis completa, Rhagoletis fausta, Rhagoletis indifferens, Rhagoletis mendax, Rhagoletis pomonella, Sarcophaga spp., Simulium spp., for example Simulium meridionale, Stomoxys spp., Tabanus spp., Tetanops spp., Tipula spp., for example Tipula paludosa, Tipula simplex, Toxotrypana curvicauda;

from the order of the Hemiptera for example Acizzia acaciaebaileyanae, Acizzia dodonaeae, Acizzia uncatoides, Acrida turrita, Acyrthosiphon spp., for example Acyrthosiphon pisum, Acrogonia spp., Aeneolamia spp., Agonoscena spp., Aleurocanthus spp., Aleyrodes proletella, Aleurolobus barodensis, Aleurothrixus floccosus, Allocaridara malayensis, Amrasca spp., for example Amrasca bigutulla, Amrasca devastans, Anuraphis cardui, Aonidiella spp., for example Aonidiella aurantii, Aonidiella citrina, Aonidiella inornata, Aphanostigma piri, Aphis spp., for example Aphis citricola, Aphis craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis viburniphila, Arboridia apicalis, Arytainilla spp., Aspidiella spp., Aspidiotus spp., for example Aspidiotus nerii, Atanus spp., Aulacorthum solani, Bemisia tabaci, Blastopsylla occidentalis, Boreioglycaspis melaleucae, Brachycaudus helichrysi, Brachycolus spp., Brevicoryne brassicae, Cacopsylla spp., for example Cacopsylla pyricola, Calligypona marginata, Capulinia spp., Carneocephala fulgida, Ceratovacuna lanigera, Cercopidae, Ceroplastes spp., Chaetosiphon fragaefolii, Chionaspis tegalensis, Chlorita onukii, Chondracris rosea, Chromaphis juglandicola, Chrysomphalus aonidum, Chrysomphalus ficus, Cicadulina mbila, Coccomytilus halli, Coccus spp., for example Coccus hesperidum, Coccus longulus, Coccus pseudomagnoliarum, Coccus viridis, Cryptomyzus ribis, Cryptoneossa spp., Ctenarytaina spp., Dalbulus spp., Dialeurodes chittendeni, Dialeurodes citri, Diaphorina citri, Diaspis spp., Diuraphis spp., Doralis spp., Drosicha spp., Dysaphis spp., for example Dysaphis apiifolia, Dysaphis plantaginea, Dysaphis tulipae, Dysmicoccus spp., Empoasca spp., for example Empoasca abrupta, Empoasca fabae, Empoasca maligna, Empoasca solana, Empoasca stevensi, Eriosoma spp., for example Eriosoma americanum, Eriosoma lanigerum, Eriosoma pyricola, Erythroneura spp., Eucalyptolyma spp., Euphyllura spp., Euscelis bilobatus, Ferrisia spp., Fiorinia spp., Furcaspis oceanica, Geococcus coffeae, Glycaspis spp., Heteropsylla cubana, Heteropsylla spinulosa, Homalodisca coagulata, Hyalopterus arundinis, Hyalopterus pruni, Icerya spp., for example Icerya purchasi, Idiocerus spp., Idioscopus spp., Laodelphax striatellus, Lecanium spp., for example Lecanium corni (=Parthenolecanium corni), Lepidosaphes spp., for example Lepidosaphes ulmi, Lipaphis erysimi, Lopholeucaspis japonica, Lycorma delicatula, Macrosiphum spp., for example Macrosiphum euphorbiae, Macrosiphum lilii, Macrosiphum rosae, Macrosteles facifrons, Mahanarva spp., Melanaphis sacchari, Metcalfiella spp., Metcalfa pruinosa, Metopolophium dirhodum, Monellia costalis, Monelliopsis pecanis, Myzus spp., for example Myzus ascalonicus, Myzus cerasi, Myzus ligustri, Myzus ornatus, Myzus persicae, Myzus nicotianae, Nasonovia ribisnigri, Neomaskellia spp., Nephotettix spp., for example Nephotettix cincticeps, Nephotettix nigropictus, Nettigoniclla spectra, Nilaparvata lugens, Oncometopia spp., Orthezia praelonga, Oxya chinensis, Pachypsylla spp., Parabemisia myricae, Paratrioza spp., for example Paratrioza cockerelli, Parlatoria spp., Pemphigus spp., for example Pemphigus bursarius, Pemphigus populivenae, Peregrinus maidis, Perkinsiella spp., Phenacoccus spp., for example Phenacoccus madeirensis, Phloeomyzus passerinii, Phorodon humuli, Phylloxera spp., for example Phylloxera devastatrix, Phylloxera notabilis, Pinnaspis aspidistrae, Planococcus spp., for example Planococcus citri, Prosopidopsylla flava, Protopulvinaria pyriformis, Pseudaulacaspis pentagona, Pseudococcus spp., for example Pseudococcus calceolariae, Pseudococcus comstocki, Pseudococcus longispinus, Pseudococcus maritimus, Pseudococcus viburni, Psyllopsis spp., Psylla spp., for example Psylla buxi, Psylla mali, Psylla pyri, Pteromalus spp., Pulvinaria spp., Pyrilla spp., Quadraspidiotus spp., for example Quadraspidiotus juglansregiae, Quadraspidiotus ostreaeformis, Quadraspidiotus perniciosus, Quesada gigas, Rastrococcus spp., Rhopalosiphum spp., for example Rhopalosiphum maidis, Rhopalosiphum oxyacanthae, Rhopalosiphum padi, Rhopalosiphum rufiabdominale, Saissetia spp., for example Saissetia coffeae, Saissetia miranda, Saissetia neglecta, Saissetia oleae, Scaphoideus titanus, Schizaphis graminum, Selenaspidus articulatus, Sipha flava, Sitobion avenae, Sogata spp., Sogatella furcifera, Sogatodes spp., Stictocephala festina, Siphoninus phillyreae, Tenalaphara malayensis, Tetragonocephela spp., Tinocallis caryaefoliae, Tomaspis spp., Toxoptera spp., for example Toxoptera aurantii, Toxoptera citricidus, Trialeurodes vaporariorum, Trioza spp., for example Trioza diospyri, Typhlocyba spp., Unaspis spp., Viteus vitifolii, Zygina spp.;

from the suborder of the Heteroptera, for example Aelia spp., Anasa tristis, Antestiopsis spp., Boisea spp., Blissus spp., Calocoris spp., Campylomma livida, Cavelerius spp., Cimex spp., for example Cimex adjunctus, Cimex hemipterus, Cimex lectularius, Cimex pilosellus, Collaria spp., Creontiades dilutus, Dasynus piperis, Dichelops furcatus, Diconocoris hewetti, Dysdercus spp., Euschistus spp., for example Euschistus heros, Euschistus servus, Euschistus tristigmus, Euschistus variolarius, Eurydema spp., Eurygaster spp., Halyomorpha halys, Heliopeltis spp., Horcias nobilellus, Leptocorisa spp., Leptocorisa varicornis, Leptoglossus occidentalis, Leptoglossus phyllopus, Lygocoris spp., for example Lygocoris pabulinus, Lygus spp., for example Lygus elisus, Lygus hesperus, Lygus lineolaris, Macropes excavatus, Megacopta cribraria, Miridae, Monalonion atratum, Nezara spp., for example Nezara viridula, Nysius spp., Oebalus spp., Pentomidae, Piesma quadrata, Piezodorus spp., for example Piezodorus guildinii, Psallus spp., Pseudacysta persea, Rhodnius spp., Sahlbergella singularis, Scaptocoris castanea, Scotinophora spp., Stephanitis nashi, Tibraca spp., Triatoma spp.;

from the order of the Hymenoptera for example Acromyrmex spp., Athalia spp., z.B. Athalia rosae, Atta spp., Camponotus spp., Dolichovespula spp., Diprion spp., for example Diprion similis, Hoplocampa spp., for example Hoplocampa cookei, Hoplocampa testudinea, Lasius spp., Linepithema (Iridiomyrmex) humile, Monomorium pharaonis, Paratrechina spp., Paravespula spp., Plagiolepis spp., Sirex spp., Solenopsis invicta, Tapinoma spp., Technomyrmex albipes,

*Urocerus* spp., *Vespa* spp., for example *Vespa crabro, Wasmannia auropunctata, Xeris* spp.;

from the order of the Isopoda, for example *Armadillidium vulgare, Oniscus asellus, Porcellio scaber*;

from the order of the Isoptera for example *Coptotermes* spp., for example *Coptotermes formosanus, Cornitermes cumulans, Cryptotermes* spp., *Incisitermes* spp., *Kalotermes* spp., *Microtermes obesi, Nasutitermes* spp., *Odontotermes* spp., *Porotermes* spp., *Reticulitermes* spp., for example *Reticulitermes flavipes, Reticulitermes hesperus*;

from the order of the Lepidoptera for example *Achroia grisella, Acronicta major, Adoxophyes* spp., for example *Adoxophyes orana, Aedia leucomelas, Agrotis* spp., for example *Agrotis segetum, Agrotis ipsilon, Alabama* spp., for example *Alabama argillacea, Amyelois transitella, Anarsia* spp., *Anticarsia* spp., for example *Anticarsia gemmatalis, Argyroploce* spp., *Autographa* spp., *Barathra brassicae, Blastodacna atra, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., for example *Chilo plejadellus, Chilo suppressalis, Choreutis pariana, Choristoneura* spp., *Chrysodeixis chalcites, Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., for example *Cydia nigricana, Cydia pomonella, Dalaca noctuides, Diaphania* spp., *Diparopsis* spp., *Diatraea saccharalis, Earias* spp., *Ecdytolopha aurantium, Elasmopalpus lignosellus, Eldana saccharina, Ephestia* spp., for example *Ephestia elutella, Ephestia kuehniella, Epinotia* spp., *Epiphyas postvittana, Erannis* spp., *Erschoviella musculana, Etiella* spp., *Eudocima* spp., *Eulia* spp., *Eupoecilia ambiguella, Euproctis* spp., for example *Euproctis chrysorrhoea, Euxoa* spp., *Feltia* spp., *Galleria mellonella, Gracillaria* spp., *Grapholitha* spp., for example *Grapholita molesta, Grapholita prunivora, Hedylepta* spp., *Helicoverpa* spp., for example *Helicoverpa armigera, Helicoverpa zea, Heliothis* spp., for example *Heliothis virescens, Hofmannophila pseudospretella, Homoeosoma* spp., *Homona* spp., *Hyponomeuta padella, Kakivoria flavofasciata, Lampides* spp., *Laphygma* spp., *Laspeyresia molesta, Leucinodes orbonalis, Leucoptera* spp., for example *Leucoptera coffeella, Lithocolletis* spp., for example *Lithocolletis blancardella, Lithophane antennata, Lobesia* spp., for example *Lobesia botrana, Loxagrotis albicosta, Lymantria* spp., for example *Lymantria dispar, Lyonetia* spp., for example *Lyonetia clerkella, Malacosoma neustria, Maruca testulalis, Mamestra brassicae, Melanitis leda, Mocis* spp., *Monopis obviella, Mythimna separata, Nemapogon cloacellus, Nymphula* spp., *Oiketicus* spp., *Omphisa* spp., *Operophtera* spp., *Oria* spp., *Orthaga* spp., *Ostrinia* spp., for example *Ostrinia nubilalis, Panolis flammea, Parnara* spp., *Pectinophora* spp., for example *Pectinophora gossypiella, Perileucoptera* spp., *Phthorimaea* spp., for example *Phthorimaea operculella, Phyllocnistis citrella, Phyllonorycter* spp., for example *Phyllonorycter blancardella, Phyllonorycter crataegella, Pieris* spp., for example *Pieris rapae, Platynota stultana, Plodia interpunctella, Plusia* spp., *Plutella xylostella* (=*Plutella maculipennis*), *Prays* spp., *Prodenia* spp., *Protoparce* spp., *Pseudaletia* spp., for example *Pseudaletia unipuncta, Pseudoplusia includens, Pyrausta nubilalis, Rachiplusia nu, Schoenobius* spp., for example *Schoenobius bipunctifer, Scirpophaga* spp., for example *Scirpophaga innotata, Scotia segetum, Sesamia* spp., for example *Sesamia inferens, Sparganothis* spp., *Spodoptera* spp., for example *Spodoptera eradiana, Spodoptera exigua, Spodoptera frugiperda, Spodoptera praefica, Stathmopoda* spp., *Stenoma* spp., *Stomopteryx subsecivella, Synanthedon* spp., *Tecia solanivora, Thaumetopoea* spp., *Thermesia gemmatalis, Tinea cloacella, Tinea pellionella, Tineola bisselliella, Tortrix* spp., *Trichophaga tapetzella, Trichoplusia* spp., for example *Trichoplusia ni, Tryporyza incertulas, Tuta absoluta, Virachola* spp.;

from the order of the Orthoptera or Saltatoria, for example *Acheta domesticus, Dichroplus* spp., *Gryllotalpa* spp., for example *Gryllotalpa gryllotalpa, Hieroglyphus* spp., *Locusta* spp., for example *Locusta migratoria, Melanoplus* spp., for example *Melanoplus devastator, Paratlanticus ussuriensis, Schistocerca gregaria*;

from the order of the Phthiraptera, for example *Damalinia* spp., *Haematopinus* spp., *Linognathus* spp., *Pediculus* spp., *Phylloxera vastatrix, Phthirus pubis, Trichodectes* spp.;

from the order of the Psocoptera, for example *Lepinotus* spp., *Liposcelis* spp.;

from the order of the Siphonaptera, for example *Ceratophyllus* spp., *Ctenocephalides* spp., for example *Ctenocephalides canis, Ctenocephalides felis, Pulex irritans, Tunga penetrans, Xenopsylla cheopis*;

from the order of the Thysanoptera, for example *Anaphothrips obscurus, Baliothrips biformis, Chaetanaphothrips leeuweni, Drepanothrips reuteri, Enneothrips flavens, Frankliniella* spp., for example *Frankliniella fusca, Frankliniella occidentalis, Frankliniella schultzei, Frankliniella tritici, Frankliniella vaccinii, Frankliniella williamsi, Haplothrips* spp., *Heliothrips* spp., *Hercinothrips femoralis, Kakothrips* spp., *Rhipiphorothrips cruentatus, Scirtothrips* spp., *Taeniothrips cardamomi, Thrips* spp., for example *Thrips palmi, Thrips tabaci*;

from the order of the Zygentoma (=Thysanura), for example *Ctenolepisma* spp., *Lepisma saccharina, Lepismodes inquilinus, Thermobia domestica*;

from the class of the Symphyla, for example *Scutigerella* spp., for example *Scutigerella immaculata*;

pests from the phylum of the Mollusca, in particular from the class of the Bivalvia, for example *Dreissena* spp.;

and also from the class of the Gastropoda, for example *Arion* spp., for example *Arion ater rufus, Biomphalaria* spp., *Bulinus* spp., *Deroceras* spp., for example *Deroceras laeve, Galba* spp., *Lymnaea* spp., *Oncomelania* spp., *Pomacea* spp., *Succinea* spp.;

animal and human parasites from the phyla of the Platyhelminthes and Nematoda, for example *Aelurostrongylus* spp., *Amidostomum* spp., *Ancylostoma* spp, for example *Ancylostoma duodenale, Ancylostoma ceylanicum, Acylostoma braziliensis, Angiostrongylus* spp., *Anisakis* spp., *Anoplocephala* spp., *Ascaris* spp., *Ascaridia* spp., *Baylisascaris* spp., *Brugia* spp., for example *Brugia malayi, Brugia timori, Bunostomum* spp., *Capillaria* spp., *Chabertia* spp., *Clonorchis* spp., *Cooperia* spp., *Crenosoma* spp., *Cyathostoma* spp., *Dicrocoelium* spp., *Dictyocaulus* spp., for example *Dictyocaulus filaria, Diphyllobothrium* spp., for example *Diphyllobothrium latum, Dipylidium* spp., *Dirofilaria* spp., *Dracunculus* spp., for example *Dracunculus medinensis, Echinococcus* spp., for example *Echinococcus granulosus, Echinococcus multilocularis, Echinostoma* spp., *Enterobius* spp., for example *Enterobius vermicularis, Eucoleus* spp., *Fasciola* spp., *Fascioloides* spp., *Fasciolopsis* spp., *Filaroides* spp., *Gongylonema* spp., *Gyrodactylus* spp., *Habronema* spp., *Haemonchus* spp., *Heligmosomoides* spp., *Heterakis* spp., *Hymenolepis* spp., for example *Hymenolepis nana, Hyostrongylus* spp., *Litomosoides* spp., *Loa* spp., for example *Loa Loa, Metastrongylus* spp., *Metorchis* spp., *Mesocestoides* spp., *Moniezia* spp., *Muellerius* spp.,

*Necator* spp., *Nematodirus* spp., *Nippostrongylus* spp., *Oesophagostomum* spp., *Ollulanus* spp., *Onchocerca* spp, for example *Onchocerca volvulus*, *Opisthorchis* spp., *Oslerus* spp., *Ostertagia* spp., *Oxyuris* spp., *Paracapillaria* spp., *Parafilaria* spp., *Paragonimus* spp., *Paramphistomum* spp., *Paranoplocephala* spp., *Parascaris* spp., *Passalurus* spp., *Protostrongylus* spp., *Schistosoma* spp., *Setaria* spp., *Spirocerca* spp., *Stephanofilaria* spp., *Stephanurus* spp., *Strongyloides* spp., for example *Strongyloides fuelleborni*, *Strongyloides stercoralis*, *Strongylus* spp., *Syngamus* spp., *Taenia* spp., for example *Taenia saginata*, *Taenia solium*, *Teladorsagia* spp., *Thelazia* spp., *Toxascaris* spp., *Toxocara* spp., *Trichinella* spp., for example *Trichinella spiralis*, *Trichinella nativa*, *Trichinella britovi*, *Trichinella nelsoni*, *Trichinella pseudospiralis*, *Trichobilharzia* spp., *Trichostrongylus* spp., *Trichuris* spp., for example *Trichuris trichiura*, *Uncinaria* spp., *Wuchereria* spp., for example *Wuchereria bancrofti*;

plant pests from the phylum of the Nematoda, i.e. plant-parasitic nematodes, in particular *Aglenchus* spp., for example *Aglenchus agricola*, *Anguina* spp., for example *Anguina tritici*, *Aphelenchoides* spp., for example *Aphelenchoides arachidis*, *Aphelenchoides fragariae*, *Belonolaimus* spp., for example *Belonolaimus gracilis*, *Belonolaimus longicaudatus*, *Belonolaimus nortoni*, *Bursaphelenchus* spp., for example *Bursaphelenchus cocophilus*, *Bursaphelenchus eremus*, *Bursaphelenchus xylophilus*, *Cacopaurus* spp., for example *Cacopaurus pestis*, *Criconemella* spp., for example *Criconemella curvata*, *Criconemella onoensis*, *Criconemella ornata*, *Criconemella rusium*, *Criconemella xenoplax* (=*Mesocriconema xenoplax*), *Criconemoides* spp., for example *Criconemoides ferniae*, *Criconemoides onoense*, *Criconemoides ornatum*, *Ditylenchus* spp., for example *Ditylenchus dipsaci*, *Dolichodorus* spp., *Globodera* spp., for example *Globodera pallida*, *Globodera rostochiensis*, *Helicotylenchus* spp., for example *Helicotylenchus dihystera*, *Hemicriconemoides* spp., *Hemicycliophora* spp., *Heterodera* spp., for example *Heterodera avenae*, *Heterodera glycines*, *Heterodera schachtii*, *Hirschmaniella* spp., *Hoplolaimus* spp., *Longidorus* spp., for example *Longidorus africanus*, *Meloidogyne* spp., for example *Meloidogyne chitwoodi*, *Meloidogyne fallax*, *Meloidogyne hapla*, *Meloidogyne incognita*, *Meloinema* spp., *Nacobbus* spp., *Neotylenchus* spp., *Paralongidorus* spp., *Paraphelenchus* spp., *Paratrichodorus* spp., for example *Paratrichodorus minor*, *Paratylenchus* spp., *Pratylenchus* spp., for example *Pratylenchus penetrans*, *Pseudohalenchus* spp., *Psilenchus* spp., *Punctodera* spp., *Quinisulcius* spp., *Radopholus* spp., for example *Radopholus citrophilus*, *Radopholus similis*, *Rotylenchulus* spp., *Rotylenchus* spp., *Scutellonema* spp., *Subanguina* spp., *Trichodorus* spp., for example *Trichodorus obtusus*, *Trichodorus primitivus*, *Tylenchorhynchus* spp., for example *Tylenchorhynchus annulatus*, *Tylenchulus* spp., for example *Tylenchulus semipenetrans*, *Xiphinema* spp., for example *Xiphinema index*.

In addition, it is possible to control, from the sub-kingdom of the Protozoa, the order of the Coccidia, for example *Eimeria* spp.

The compounds of the formula (I) can optionally, at certain concentrations or application rates, also be used as herbicides, safeners, growth regulators or agents to improve plant properties, as microbicides or gametocides, for example as fungicides, antimycotics, bactericides, virucides (including agents against viroids) or as agents against MLO (mycoplasma-like organisms) and RLO (rickettsia-like organisms). If appropriate, they can also be used as intermediates or precursors for the synthesis of other active compounds.

Formulations

The present invention further relates to formulations and use forms prepared therefrom as pesticides, for example drench, drip and spray liquors, comprising at least one compound of the formula (I). Optionally, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulphate or diammonium hydrogenphosphate and/or retention promoters, for example dioctyl sulphosuccinate or hydroxypropylguar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I), optionally comprise further agrochemically active compounds.

Preference is given to formulations or use forms comprising auxiliaries, for example extenders, solvents, spontaneity promoters, carriers, emulsifiers, dispersants, frost protection agents, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are prepared in a known way, for example by mixing the compounds of the formula (I) with auxiliaries such as, for example, extenders, solvents and/or solid carriers and/or other auxiliaries such as, for example, surfactants. The formulations are produced either in suitable facilities or else before or during application.

The auxiliaries used may be substances suitable for imparting special properties, such as certain physical, technical and/or biological properties, to the formulation of the compounds of the formula (I), or to the use forms prepared from these formulations (for example ready-to-use pesticides such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the simple and substituted amines, amides, lactams (such as N-alkylpyrrolidones) and lactones, the sulphones and sulphoxides (such as dimethyl sulphoxide).

If the extender utilized is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and water.

In principle, it is possible to use all suitable solvents. Examples of suitable solvents are aromatic hydrocarbons, such as xylene, toluene or alkylnaphthalenes, chlorinated aromatic or aliphatic hydrocarbons, such as chlorobenzene, chloroethylene or methylene chloride, aliphatic hydrocarbons, such as cyclohexane, paraffins, mineral oil fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulphoxide, and also water.

In principle, it is possible to use all suitable carriers. Useful carriers especially include: for example ammonium salts and ground natural minerals such as kaolins, clays, talc, chalk, quartz, attapulgite, montmorillonite or diatomaceous earth, and ground synthetic minerals such as finely divided silica, alumina and natural or synthetic silicates, resins, waxes and/or solid fertilizers. It is likewise possible to use mixtures of such carriers. Useful carriers for granules include: for example crushed and fractionated natural rocks such as calcite, marble, pumice, sepiolite, dolomite, and synthetic granules of inorganic and organic flours, and also granules of organic material such as sawdust, paper, coconut shells, maize cobs and tobacco stalks.

It is also possible to use liquefied gaseous extenders or solvents. Especially suitable are those extenders or carriers which are gaseous at standard temperature and under atmospheric pressure, for example aerosol propellants such as halogenated hydrocarbons, and also butane, propane, nitrogen and carbon dioxide.

Examples of emulsifiers and/or foam formers, dispersants or wetting agents having ionic or nonionic properties or mixtures of these surface-active substances are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty acid esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is advantageous if one of the compounds of the formula (I) and/or one of the inert carriers is insoluble in water and when the application takes place in water.

Further auxiliaries which may be present in the formulations and the use forms derived therefrom are dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components which may be present are stabilizers, such as cold stabilizers, preservatives, antioxidants, light stabilizers, or other agents which improve chemical and/or physical stability. Foam generators or antifoams may also be present.

In addition, the formulations and the use forms derived therefrom may also comprise, as additional auxiliaries, stickers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids. Further auxiliaries may be mineral and vegetable oils.

It is possible if appropriate for still further auxiliaries to be present in the formulations and the use forms derived therefrom. Examples of such additives are fragrances, protective colloids, binders, adhesives, thickeners, thixotropic agents, penetrants, retention promoters, stabilizers, sequestrants, complexing agents, humectants, spreaders. In general, the compounds of the formula (I) can be combined with any solid or liquid additive commonly used for formulation purposes.

Useful retention promoters include all those substances which reduce dynamic surface tension, for example dioctyl sulphosuccinate, or increase viscoelasticity, for example hydroxypropylguar polymers.

Suitable penetrants in the present context are all those substances which are usually used for improving the penetration of agrochemically active compounds into plants. Penetrants are defined in this context by their ability to penetrate from the (generally aqueous) application liquor and/or from the spray coating into the cuticle of the plant and hence increase the mobility of the active compounds in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations preferably comprise between 0.00000001% and 98% by weight of the compound of the formula (I), more preferably between 0.01% and 95% by weight of the compound of the formula (I), most preferably between 0.5% and 90% by weight of the compound of the formula (I), based on the weight of the formulation.

The content of the compound of the formula (I) in the use forms prepared from the formulations (in particular pesticides) may vary within wide ranges. The concentration of the compound of the formula (I) in the use forms may typically be between 0.00000001% and 95% by weight of the compound of the formula (I), preferably between 0.00001% and 1% by weight, based on the weight of the use form. Application is accomplished in a customary manner appropriate for the use forms.

Mixtures

The compounds of the formula (I) can also be used in a mixture with one or more suitable fungicides, bactericides, acaricides, molluscicides, nematicides, insecticides, microbiological agents, beneficial organisms, herbicides, fertilizers, bird repellents, phytotonics, sterilants, safeners, semiochemicals and/or plant growth regulators, in order thus, for example, to broaden the spectrum of action, prolong the period of action, enhance the rate of action, prevent repellency or prevent evolution of resistance. In addition, active compound combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products.

In addition, the compounds of the formula (I) may be present in a mixture with other active compounds or semiochemicals such as attractants and/or bird repellents and/or plant activators and/or growth regulators and/or fertilizers. Likewise, the compounds of the formula (I) can be used in mixtures with agents to improve plant properties, for example growth, yield and quality of the harvested material.

In a particular embodiment according to the invention, the compounds of the formula (I) are present in formulations or in the use forms prepared from these formulations in a mixture with further compounds, preferably those as described below.

If one of the compounds mentioned below can occur in different tautomeric forms, these forms are also included even if not explicitly mentioned in each case.

Insecticides/Acaricides/Nematicides

The active compounds specified here with their common names are known and are described for example in "The Pesticide Manual", 16th ed., British Crop Protection Council 2012, or can be searched for on the Internet (e.g. http://www.alanwood.net/pesticides).

(1) Acetylcholinesterase (AChE) inhibitors, such as, for example, carbamates, for example alanycarb, aldicarb, bendiocarb, benfuracarb, butocarboxim, butoxycarboxim, carbaryl, carbofuran, carbosulphan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulphoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulphotep, tebupirimfos, temephos, terbufos, tetrachlorvinphos, thiometon, triazophos, triclorfon and vamidothion.

(2) GABA-gated chloride channel antagonists, for example cyclodiene-organochlorines, e.g. chlordane and endosulphan or phenylpyrazoles (fiproles), e.g. ethiprole and fipronil.

(3) Sodium channel modulators/voltage-gated sodium channel blockers, for example pyrethroids, e.g. acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomers], deltamethrin, empenthrin [(EZ)-(1R) isomers], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans isomer], prallethrin, pyrethrins (pyrethrum), resmethrin, silafluofen, tefluthrin, tetramethrin, tetramethrin [(1R) isomers)], tralomethrin and transfluthrin or DDT or methoxychlor.

(4) Nicotinergic acetylcholine receptor (nAChR) agonists, for example neonicotinoids, e.g. acetamiprid, clothianidin, dinotefuran, imidacloprid, nitenpyram, thiacloprid and thiamethoxam or nicotine or sulphoxaflor or flupyradifurone.

(5) Allosteric activators of the nicotinergic acetylcholine receptor (nAChR), for example spinosyns, e.g. spinetoram and spinosad.

(6) Chloride channel activators, for example avermectins/milbemycins, e.g. abamectin, emamectin benzoate, lepimectin and milbemectin.

(7) Juvenile hormone imitators, for example, juvenile hormone analogues, e.g. hydroprene, kinoprene and methoprene or fenoxycarb or pyriproxyfen.

(8) Active compounds having unknown or nonspecific mechanisms of action, for example
alkyl halides, e.g. methyl bromide and other alkyl halides; or chloropicrine or sulphuryl fluoride or borax or tartar emetic.

(9) Selective antifeedants, e.g. pymetrozine or flonicamid.

(10) Mite growth inhibitors, e.g. clofentezine, hexythiazox and diflovidazin or etoxazole.

(11) Microbial disruptors of the insect gut membrane, e.g. *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT plant proteins: Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors, for example diafenthiuron or organotin compounds, e.g. azocyclotin, cyhexatin and fenbutatin oxide or propargite or tetradifon.

(13) Oxidative phosphorylation decouplers that interrupt the H proton gradient, for example chlorfenapyr, DNOC and sulphluramid.

(14) Nicotinergic acetylcholine receptor antagonists, for example bensultap, cartap hydrochloride, thiocyclam, and thiosultap-sodium.

(15) Chitin biosynthesis inhibitors, type 0, for example bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin.

(17) Moulting inhibitors (especially for Diptera, i.e. dipterans), for example cyromazine.

(18) Ecdysone receptor agonists, for example chromafenozide, halofenozide, methoxyfenozide and tebufenozide.

(19) Octopaminergic agonists, for example amitraz.

(20) Complex-III electron transport inhibitors, for example hydramethylnon or acequinocyl or fluacrypyrim.

(21) Complex-I electron transport inhibitors, for example METI acaricides, e.g. fenazaquin, fenpyroximate, pyrimidifen, pyridaben, tebufenpyrad and tolfenpyrad or rotenone (Derris).

(22) Voltage-gated sodium channel blockers, for example indoxacarb or metaflumizone.

(23) Inhibitors of acetyl-CoA carboxylase, for example tetronic and tetramic acid derivatives, e.g. spirodiclofen, spiromesifen and spirotetramat.

(24) Complex-IV electron transport inhibitors, for example phosphines, e.g. aluminium phosphide, calcium phosphide, phosphine and zinc phosphide or cyanide.

(25) Complex-II electron transport inhibitors, for example cyenopyrafen and cyflumetofen.

(28) Ryanodine receptor effectors, for example diamides, e.g. chlorantraniliprole, cyantraniliprole and flubendiamide.

Further active compounds having an unknown or unclear mechanism of action, for example afidopyropen, afoxolaner, azadirachtin, benclothiaz, benzoximate, bifenazate, broflanilide, bromopropylate, chinomethionat, cryolite, cyclaniliprole, cycloxaprid, cyhalodiamide, dicloromezotiaz, dicofol, diflovidazin, flometoquin, fluazaindolizine, fluensulphone, flufenerim, flufenoxystrobin, flufiprole, fluhexafon, fluopyram, fluralaner, fluxametamide, fufenozide, guadipyr, heptafluthrin, imidaclothiz, iprodione, lotilaner, meperfluthrin, paichongding, pyflubumide, pyridalyl, pyrifluquinazon, pyriminostrobin, sarolaner, tetramethylfluthrin, tetraniliprole, tetrachlorantraniliprole, tioxazafen, thiofluoximate, triflumezopyrim and iodomethane; and additionally preparations based on *Bacillus firmus* (1-1582, BioNeem, Votivo), and the following known active compounds: 1-{2-fluoro-4-methyl-5-[(2,2,2-trifluoroethyl)sulphinyl] phenyl}-3-(trifluoromethyl)-1H-1,2,4-triazole-5-amine (known from WO2006/043635), {1'-[(2E)-3-(4-chlorophenyl)prop-2-en-1-yl]-5-fluorospiro[indol-3,4'-piperidin]-1 (2H)-yl}(2-chloropyridin-4-yl)methanone (known from WO2003/106457), 2-chloro-N-[2-{1-[(2E)-3-(4-chlorophenyl)prop-2-en-1-yl]piperidin-4-yl}-4-(trifluoromethyl)phenyl]isonicotinamide (known from WO2006/003494), 3-(2,5-dimethylphenyl)-4-hydroxy-8-methoxy-1,8-diazaspiro [4.5]dec-3-en-2-one (known from WO2009/049851), 3-(2,5-dimethylphenyl)-8-methoxy-2-oxo-1,8-diazaspiro[4.5] dec-3-en-4-ylethyl carbonate (known from WO2009/049851), 4-(but-2-yn-1-yloxy)-6-(3,5-dimethylpiperidin-1-yl)-5-fluoropyrimidine (known from WO2004/099160), 4-(but-2-yn-1-yloxy)-6-(3-chlorophenyl)pyrimidine (known from WO2003/076415), PF1364 (CAS Reg. No. 1204776-60-2), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl] carbonyl}amino)benzoyl]-2-ethylhydrazinecarboxylate (known from WO2005/085216), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2009/080250), N-[(2E)-1-[(6-chloropyridin-3-yl)methyl]pyridin-2(1H)-ylidene]-2,2,2-trifluoroacetamide (known from WO2012/029672), 1-[(2-chloro-1,3-thiazol-5-yl)methyl]-4-oxo-3-phenyl-4H-pyrido[1,2-a]pyrimidin-1-ium-2-olate (known from WO2009/099929), 1-[(6-chloropyridin-3-yl)methyl]-4-oxo-3-phenyl-4H-pyrido[1,2-a]pyrimidin-1-ium-2-olate (known from WO2009/099929), 4-(3-{2,6-dichloro-4-[(3,3-dichloroprop-2-en-1-yl)oxy]phenoxy}propoxy)-2-methoxy-6-(trifluoromethyl)pyrimidine (known from CN101337940), N-[2-(tert-butylcarbamoyl)-4-chloro-6-methylphenyl]-1-(3-chloropyridin-2-yl)-3-(fluoromethoxy)-1H-pyrazole-5-carboxamide (known from WO2008/134969, butyl [2-(2,4-dichlorophenyl)-3-oxo-4-oxaspiro [4.5]dec-1-en-1-yl]carbonate (known from CN 102060818), 3E)-3-[1-[(6-chloro-3-pyridyl)methyl]-2-pyridylidene]-1,1,1-trifluoropropan-2-one (known from WO2013/144213, N-(methylsulphonyl)-6-[2-(pyridin-3-yl)-1,3-thiazol-5-yl] pyridine-2-carboxamide (known from WO2012/000896), N-[3-(benzylcarbamoyl)-4-chlorophenyl]-1-methyl-3-(pentafluoroethyl)-4-(trifluoromethyl)-1H-pyrazole-5-carboxamide (known from WO2010/051926), 5-bromo-4-chloro-N-[4-chloro-2-methyl-6-(methylcarbamoyl)phenyl]-2-(3-chloro-2-pyridyl)pyrazole-3-carboxamide (known from CN103232431).

Fungicides

The active compounds specified herein by their common name are known and described, for example, in "Pesticide Manual" or on the Internet (for example: http://www.alanwood.net/pesticides).

All the fungicidal mixing components listed in classes (1) to (15) may optionally form salts with corresponding bases or acids if suitable functional groups are present. In addition, the fungicidal mixing components listed in classes (1) to (15) also include tautomeric forms if tautomerism is possible.

1) inhibitors of the ergosterol biosynthesis, for example (1.01) aldimorph, (1.02) azaconazole, (1.03) bitertanol, (1.04) bromuconazole, (1.05) cyproconazole, (1.06) diclobutrazole, (1.07) difenoconazole, (1.08) diniconazole, (1.09) diniconazole-M, (1.10) dodemorph, (1.11) dodemorph acetate, (1.12) epoxiconazole, (1.13) etaconazole, (1.14) fenarimol, (1.15) fenbuconazole, (1.16) fenhexamid, (1.17) fenpropidin, (1.18) fenpropimorph, (1.19) fluquinconazole, (1.20) flurprimidol, (1.21) flusilazole, (1.22) flutriafol, (1.23) furconazole, (1.24) furconazole-cis, (1.25) hexaconazole, (1.26) imazalil, (1.27) imazalil sulphate, (1.28) imibenconazole, (1.29) ipconazole, (1.30) metconazole, (1.31) myclobutanil, (1.32) naftifine, (1.33) nuarimol, (1.34) oxpoconazole, (1.35) paclobutrazole, (1.36) pefurazoate, (1.37) penconazole, (1.38) piperalin, (1.39) prochloraz, (1.40) propiconazole, (1.41) prothioconazole, (1.42) pyributicarb, (1.43) pyrifenox, (1.44) quinconazole, (1.45) simeconazole, (1.46) spiroxamine, (1.47) tebuconazole, (1.48) terbinafin, (1.49) tetraconazole, (1.50) triadimefon, (1.51) triadimenol, (1.52) tridemorph, (1.53) triflumizole, (1.54) triforin, (1.55) triticonazole, (1.56) uniconazole, (1.57) uniconazole-p, (1.58) viniconazole, (1.59) voriconazole, (1.60) 1-(4-chlorophenyl)-2-(1H-1,2,4-triazol-1-yl) cycloheptanol, (1.61) 1-(2,2-dimethyl-2,3-dihydro-1H-inden-1-yl)-1H-imidazole-5-carboxylic acid methyl ester, (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide, (1.64) O-[1-(4-methoxyphenoxy)-3,3-dimethylbutan-2-yl]-1H-imidazole-1-carbothioate, (1.65) pyrisoxazole, (1.66) 2-{[3-(2-chlorophenyl)-2-(2,4-difluorophenyl)oxiran-2-yl] methyl}-2,4-dihydro-3H-1,2,4-triazole-3-thione, (1.67) 1-{[3-(2-chlorophenyl)-2-(2,4-dicuorophenyl)oxiran-2-yl] methyl}-1H-1,2,4-triazol-5-ylthiocyanate, (1.68) 5-(allylsulphanyl)-1-{[3-(2-chlorophenyl)-2-(2,4-difluorophenyl) oxiran-2-yl]methyl}-1H-1,2,4-triazole, (1.69) 2-[1-(2,4-dichlorophenyl)-5-hydroxy-2,6,6-trimethylheptan-4-yl]-2,4-dihydro-3H-1,2,4-triazole-3-thione, (1.70) 2-{[rel(2R,3S)-3-(2-chlorophenyl)-2-(2,4-difluorophenyl)oxiran-2-yl] methyl}-2,4-dihydro-3H-1,2,4-triazole-3-thione, (1.71) 2-{[rel(2R,3R)-3-(2-chlorophenyl)-2-(2,4-difluorophenyl) oxiran-2-yl]methyl}-2,4-dihydro-3H-1,2,4-triazole-3- thione, (1.72) 1-{[rel(2R,3S)-3-(2-chlorophenyl)-2-(2,4-difluorophenyl)oxiran-2-yl]methyl}-1H-1,2,4-triazol-5-ylthiocyanate, (1.73) 1-{[rel(2R,3R)-3-(2-chlorophenyl)-2-(2,4-difluorophenyl)oxiran-2-yl]methyl}-1H-1,2,4-triazol-5-ylthiocyanate, (1.74) 5-(allylsulphanyl)-1-{[rel(2R,3S)-3-(2-chlorophenyl)-2-(2,4-difluorophenyl)oxiran-2-yl]methyl}-1H-1,2,4-triazole, (1.75) 5-(allylsulphanyl)-1-({[rel(2R,3R)-3-(2-chlorophenyl)-2-(2,4-difluorophenyl)oxiran-2-yl]methyl}-1H-1,2,4-triazole, (1.76) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.77) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.78) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.79) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.80) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.81) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.82) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.83) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.84) 2-[4-(4-chlorophenoxy)-2-(trifluoromethyl)phenyl]-1-(1H-1,2,4-triazol-1-yl)propan-2-ol, (1.85) 2-[4-(4-chlorophenoxy)-2-(trifluoromethyl)phenyl]-1-(1H-1,2,4-triazol-1-yl)butan-2-ol, (1.86) 2-[4-(4-chlorophenoxy)-2-(trifluoromethyl)phenyl]-1-(1H-1,2,4-triazol-1-yl)pentan-2-ol, (1.87) 2-[2-chloro-4-(4-chlorophenoxy)phenyl]-1-(1H-1,2,4-triazol-1-yl)butan-2-ol, (1.88) 2-[2-chloro-4-(2,4-dichlorophenoxy)phenyl]-1-(1H-1,2,4-triazol-1-yl)propan-2-ol, (1.89) (2R)-2-(1-chlorocyclopropyl)-4-[(1R)-2,2-dichlorocyclopropyl]-1-(1H-1,2,4-triazol-1-yl)butan-2-ol, (1.90) (2R)-2-(1-chlorocyclopropyl)-4-[(1S)-2,2-dichlorocyclopropyl]-1-(1H-1,2,4-triazol-1-yl)butan-2-ol, (1.91) (2S)-2-(1-chlorocyclopropyl)-4-[(1S)-2,2-dichlorocyclopropyl]-1-(1H-1,2,4-triazol-1-yl)butan-2-ol, (1.92) (2S)-2-(1-chlorocyclopropyl)-4-[(1R)-2,2-dichlorocyclopropyl]-1-(1H-1,2,4-triazol-1-yl)butan-2-ol, (1.93) (1S,2R,5R)-5-(4-chlorobenzyl)-2-(chloromethyl)-2-methyl-1-(1H-1,2,4-triazol-1-ylmethyl)cyclopentanol, (1.94) (1R,2S,5S)-5-(4-chlorobenzyl)-2-(chloromethyl)-2-methyl-1-(1H-1,2,4-triazol-1-ylmethyl)cyclopentanol, (1.95) 5-(4-chlorobenzyl)-2-(chloromethyl)-2-methyl-1-(1H-1,2,4-triazol-1-ylmethyl)cyclopentanol.

2) Inhibitors of the respiratory chain on complex I or II, for example (2.01) bixafen, (2.02) boscalid, (2.03) carboxin, (2.04) diflumetorim, (2.05) fenfuram, (2.06) fluopyram, (2.07) flutolanil, (2.08) fluxapyroxad, (2.09) furametpyr, (2.10) furmecyclox, (2.11) isopyrazam (mixture of syn-epimeric racemate 1RS,4SR,9RS and anti-epimeric racemate 1RS,4SR,9SR), (2.12) isopyrazam (anti-epimeric racemate 1RS,4SR,9SR), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil, (2.19) oxycarboxin, (2.20) penflufen, (2.21) penthiopyrad, (2.22) sedaxane, (2.23) thifluzamide, (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide, (2.28) 5,8-difluoro-N-[2-(2-fluoro-4-{[4-(trifluoromethyl)pyridin-2-yl]oxy}phenyl)ethyl]quinazolin-4-amin, (2.29) benzovindiflupyr, (2.30) N-[(1S,4R)-9-(dichloromethylene)-1,2,3,4-tetrahydro-1,4-methanonaphthalin-5-yl]-3-(difluoromethyl)-1-methyl-1H-pyrazole-4-carboxamide, (2.31) N-[(1R,4S)-9-(dichloromethylene)-1,2,3,4-tetrahydro-1,4-methanonaphthalin-5-yl]-3-(difluoromethyl)-1-methyl-1H-pyrazole-4-carboxamide, (2.32) 3-(difluoromethyl)-1-methyl-N-(1,1,3-trimethyl-2,3-dihydro-1H-inden-4-yl)-1H-pyrazole-4-carboxamide, (2.33) 1,3,5-trimethyl-N-(1,1,3-trimethyl-2,3-dihydro-1H-inden-4-yl)-1H-pyrazole-4-carboxamide, (2.34) 1-methyl-3-(trifluoromethyl)-N-(1,1,3-trimethyl-2,3-dihydro-1H-inden-4-yl)-1H-pyrazole-4-carboxamide, (2.35) 1-methyl-3-(trifluoromethyl)-N-[(3R)-1,1,3-trimethyl-2,3-dihydro-1H-inden-4-yl]-1H-pyrazole-4-carboxamide, (2.36) 1-methyl-3-(trifluoromethyl)-N-[(3S)-1,1,3-trimethyl-2,3-dihydro-1H-inden-4-yl]-1H-pyrazole-4-carboxamide, (2.37) 3-(difluoromethyl)-1-methyl-N-[(3S)-1,1,3-trimethyl-2,3-dihydro-1H-inden-4-yl]-1H-pyrazole-4-carboxamide, (2.38) 3-(difluoromethyl)-1-methyl-N-[(3R)-1,1,3-trimethyl-2,3-dihydro-1H-inden-4-yl]-1H-pyrazole-4-carboxamide, (2.39) 1,3,5-trimethyl-N-[(3R)-1,1,3-trimethyl-2,3-dihydro-1H-inden-4-yl]-1H-pyrazole-4-carboxamide, (2.40) 1,3,5-trimethyl-N-[(3S)-1,1,3-trimethyl-2,3-dihydro-1H-inden-4-yl]-1H-pyrazole-4-carboxamide, (2.41) benodanil, (2.42) 2-chloro-N-(1,1,3-trimethyl-2,3-dihydro-1H-inden-4-yl)pyridine-3-carboxamide, (2.43) isofetamid, (2.44) 1-methyl-3-(trifluoromethyl)-N-[2'-(trifluoromethyl)biphenyl-2-yl]-1H-pyrazole-4-carboxamide, (2.45) N-(4'-chlorobiphenyl-2-yl)-3-(difluoromethyl)-1-methyl-1H-pyrazole-4-carboxamide, (2.46) N-(2',4'-dichlorobiphenyl-2-yl)-3-(difluoromethyl)-1-methyl-1H-pyrazole-4-carboxamide, (2.47) 3-(difluoromethyl)-1-methyl-N-[4'-(trifluoromethyl)biphenyl-2-yl]-1H-pyrazole-4-carboxamide, (2.48) N-(2',5'-difluorobiphenyl-2-yl)-1-methyl-3-(trifluoromethyl)-1H-pyrazole-4-carboxamide, (2.49) 3-(difluoromethyl)-1-methyl-N-[4'-(prop-1-yn-1-yl)biphenyl-2-yl]-1H-pyrazole-4-carboxamide, (2.50) 5-fluoro-1,3-dimethyl-N-[4'-(prop-1-yn-1-yl)biphenyl-2-yl]-1H-pyrazole-4-carboxamide, (2.51) 2-chloro-N-[4'-(prop-1-yn-1-yl)biphenyl-2-yl]nicotinamide, (2.52) 3-(difluoromethyl)-N-[4'-(3,3-dimethylbut-1-yn-1-yl)biphenyl-2-yl]-1-methyl-1H-pyrazole-4-carboxamide, (2.53) N-[4'-(3,3-dimethylbut-1-yn-1-yl)biphenyl-2-yl]-5-fluoro-1,3-dimethyl-1H-pyrazole-4-carboxamide, (2.54) 3-(difluoromethyl)-N-(4'-ethynylbiphenyl-2-yl)-1-methyl-1H-pyrazole-4-carboxamide, (2.55) N-(4'-ethynylbiphenyl-2-yl)-5-fluoro-1,3-dimethyl-1H-pyrazole-4-carboxamide, (2.56) 2-chloro-N-(4'-ethynylbiphenyl-2-yl)nicotinamide, (2.57) 2-chloro-N-[4'-(3,3-dimethylbut-1-yn-1-yl)biphenyl-2-yl]nicotinamide, (2.58) 4-(difluoromethyl)-2-methyl-N-[4'-(trifluoromethyl)biphenyl-2-yl]-1,3-thiazole-5-carboxamide, (2.59) 5-fluoro-N-[4'-(3-hydroxy-3-methylbut-1-yn-1-yl)biphenyl-2-yl]-1,3-dimethyl-1H-pyrazole-4-carboxamide, (2.60) 2-chloro-N-[4'-(3-hydroxy-3-methylbut-1-yn-1-yl)biphenyl-2-yl]nicotinamide, (2.61) 3-(difluoromethyl)-N-[4'-(3-methoxy-3-methylbut-1-yn-1-yl)biphenyl-2-yl]-1-methyl-1H-pyrazole-4-carboxamide, (2.62) 5-fluoro-N-[4'-(3-methoxy-3-methylbut-1-yn-1-yl)biphenyl-2-yl]-1,3-dimethyl-1H-pyrazole-4-carboxamide, (2.63) 2-chloro-N-[4'-(3-methoxy-3-methylbut-1-yn-1-yl)biphenyl-2-yl]nicotinamide, (2.64) 1,3-dimethyl-N-(1,1,3- trimethyl-2,3-dihydro-1H-inden-4-yl)-1H-pyrazole-4-carboxamide, (2.65) 1,3-dimethyl-N-[(3R)-1,1,3-trimethyl-2,3-dihydro-1H-inden-4-yl]-1H-pyrazole-4-carboxamide, (2.66) 1,3-dimethyl-N-[(3S)-1,1,3-trimethyl-2,3-dihydro-1H-inden-4-yl]-1H-pyrazole-4-carboxamide, (2.67) 3-(difluoromethyl)-N-methoxy-1-methyl-N-[1-(2,4,6-trichlorophenyl)propan-2-yl]-1H-pyrazole-4-carboxamide, (2.68) 3-(difluoromethyl)-N-(7-fluoro-1,1,3-trimethyl-2,3-dihydro-1H-inden-4-yl)-1-methyl-1H-pyrazole-4-carboxamide, (2.69) 3-(difluoromethyl)-N-[(3R)-7-fluoro-1,1,3-trimethyl-2,3-dihydro-1H-inden-4-yl]-1-methyl-1H-pyrazole-4-carboxamide, (2.70) 3-(difluoromethyl)-N-[(3S)-7-fluoro-1,1,3-trimethyl-2,3-dihydro-1H-inden-4-yl]-1-methyl-1H-pyrazole-4-carboxamide.

3) Inhibitors of the respiratory chain on complex III, for example (3.01) ametoctradin, (3.02) amisulbrom, (3.03) azoxystrobin, (3.04) cyazofamid, (3.05) coumethoxystrobin, (3.06) coumoxystrobin, (3.07) dimoxystrobin, (3.08) enoxastrobin, (3.09) famoxadon, (3.10) fenamidon, (3.11) flufenoxystrobin, (3.12) fluoxastrobin, (3.13) kresoxim-methyl, (3.14) metominostrobin, (3.15) orysastrobin, (3.16) picoxystrobin, (3.17) pyraclostrobin, (3.18) pyrametostrobin, (3.19) pyraoxystrobin, (3.20) pyribencarb, (3.21) triclopyricarb, (3.22) trifloxystrobin, (3.23) (2E)-2-(2-{[6-(3-chloro-2-methylphenoxy)-5-fluoropyrimidin-4-yl]oxy}phenyl)-2-(methoxyimino)-N-methylacetamide, (3.24) (2E)-2-(methoxyimino)-N-methyl-2-(2-{[({(1E)-1-[3-(trifluoromethyl)phenyl]ethyliden}amino)oxy]methyl}phenyl)acetamide, (3.25) (2E)-2-(methoxyimino)-N-methyl-2-{2-[(E)-({1-[3-(trifluoromethyl)phenyl]ethoxy}imino)methyl]phenyl}acetamide, (3.26) (2E)-2-{2-[({[(1E)-1-(3-{[(E)-1-fluoro-2-phenylvinyl]oxy}phenyl)ethyliden]amino}oxy)methyl]phenyl}-2-(methoxyimino)-N-methylacetamide, (3.27) fenaminostrobin, (3.28) 5-methoxy-2-methyl-4-(2-{[({(1E)-1-[3-(trifluoromethyl)phenyl]ethyliden}amino)oxy]methyl J}phenyl)-2,4-dihydro-3H-1,2,4-triazol-3-one, (3.29) (2E)-2-{2-[({cyclopropyl[(4-methoxyphenyl)imino]methyl}sulphanyl)methyl]phenyl}-3-methoxyacrylic acid methyl ester, (3.30) N-(3-ethyl-3,5,5-trimethylcyclohexyl)-3-formamido-2-hydroxybenzamide, (3.31) 2-{2-[(2,5-dimethylphenoxy)methyl]phenyl}-2-methoxy-N-methylacetamide, (3.32) 2-{2-[(2,5-dimethylphenoxy)methyl]phenyl}-2-methoxy-N-methylacetamide, (3.33) (2E,3Z)-5-{[1-(4-chlorophenyl)-1H-pyrazol-3-yl]oxy}-2-(methoxyimino)-N,3-dimethylpent-3-enamide.

4) Inhibitors of mitosis and cell division, for example (4.01) benomyl, (4.02) carbendazim, (4.03) chlorfenazole, (4.04) diethofencarb, (4.05) ethaboxam, (4.06) fluopicolide, (4.07) fuberidazole, (4.08) pencycuron, (4.09) thiabendazole, (4.10) thiophanate-methyl, (4.11) thiophanate, (4.12) zoxamide, (4.13) 5-chloro-7-(4-methylpiperidin-1-yl)-6-(2,4,6-trifluorophenyl)[1,2,4]triazolo[1,5-a]pyrimidine, (4.14) 3-chloro-5-(6-chloropyridin-3-yl)-6-methyl-4-(2,4,6-trifluorophenyl)pyridazine.

5) Compounds capable of having multisite action, for example (5.01) Bordeaux mixture, (5.02) captafol, (5.03) captan, (5.04) chlorothalonil, (5.05) copper hydroxide, (5.06) copper naphthenate, (5.07) copper oxide, (5.08) copper oxychloride, (5.09) copper(2+) sulphate, (5.10) dichlofluanid, (5.11) dithianon, (5.12) dodine, (5.13) dodine free base, (5.14) ferbam, (5.15) fluorofolpet, (5.16) folpet, (5.17) guazatine, (5.18) guazatine acetate, (5.19) iminoctadine, (5.20) iminoctadine albesilate, (5.21) iminoctadine triacetate, (5.22) mancopper, (5.23) mancozeb, (5.24) maneb, (5.25) metiram, (5.26) metiram zinc, (5.27) oxine-copper, (5.28) propamidine, (5.29) propineb, (5.30) sulphur and sulphur preparations including calcium polysulphide, (5.31) thiram, (5.32) tolylfluanid, (5.33) zineb, (5.34) ziram, (5.35) anilazine.

6) Compounds capable of inducing host defence, for example (6.01) acibenzolar-S-methyl, (6.02) isotianil, (6.03) probenazole, (6.04) tiadinil, (6.05) laminarin.

7) Inhibitors of the amino acid and/or protein biosynthesis, for example (7.01) andoprim, (7.02) blasticidin-S, (7.03) cyprodinil, (7.04) kasugamycin, (7.05) kasugamycin hydrochloride hydrate, (7.06) mepanipyrim, (7.07) pyrimethanil, (7.08) 3-(5-fluoro-3,3,4,4-tetramethyl-3,4-dihydroisoquinolin-1-yl)quinoline, (7.09) oxytetracycline, (7.10) streptomycin.

8) Inhibitors of ATP production, for example (8.01) fentin acetate, (8.02) fentin chloride, (8.03) fentin hydroxide, (8.04) silthiofam.

9) Inhibitors of cell wall synthesis, for example (9.01) benthiavalicarb, (9.02) dimethomorph, (9.03) flumorph, (9.04) iprovalicarb, (9.05) mandipropamid, (9.06) polyoxins, (9.07) polyoxorim, (9.08) validamycin A, (9.09) valifenalate, (9.10) polyoxin B, (9.11) (2E)-3-(4-tert-butylphenyl)-3-(2-chloropyridin-4-yl)-1-(morpholin-4-yl)prop-2-en-1-one, (9.12) (2Z)-3-(4-tert-butylphenyl)-3-(2-chloropyridin-4-yl)-1-(morpholin-4-yl)prop-2-en-1-one.

10) Inhibitors of lipid and membrane synthesis, for example (10.01) biphenyl, (10.02) chloroneb, (10.03) dicloran, (10.04) edifenphos, (10.05) etridiazole, (10.06) iodocarb, (10.07) iprobenfos, (10.08) isoprothiolane, (10.09) propamocarb, (10.10) propamocarb hydrochloride, (10.11) prothiocarb, (10.12) pyrazophos, (10.13) quintozene, (10.14) tecnazene, (10.15) tolclofos-methyl.

11) Inhibitors of melanin biosynthesis, for example (11.01) carpropamid, (11.02) diclocymet, (11.03) fenoxanil, (11.04) phthalide, (11.05) pyroquilon, (11.06) tricyclazole, (11.07) 2,2,2-trifluoroethyl {3-methyl-1-[(4-methylbenzoyl)amino]butan-2-yl}carbamate.

12) Inhibitors of nucleic acid synthesis, for example (12.01) benalaxyl, (12.02) benalaxyl-M (kiralaxyl), (12.03) bupirimate, (12.04) clozylacon, (12.05) dimethirimol, (12.06) ethirimol, (12.07) furalaxyl, (12.08) hymexazole, (12.09) metalaxyl, (12.10) metalaxyl-M (mefenoxam), (12.11) ofurace, (12.12) oxadixyl, (12.13) oxolinic acid, (12.14) octhilinone.

13) Inhibitors of signal transduction, for example (13.01) chlozolinate, (13.02) fenpiclonil, (13.03) fludioxonil, (13.04) iprodione, (13.05) procymidone, (13.06) quinoxyfen, (13.07) vinclozolin, (13.08) proquinazid.

14) Compounds capable of acting as uncouplers, for example (14.01) binapacryl, (14.02) dinocap, (14.03) ferimzone, (14.04) fluazinam, (14.05) meptyldinocap.

15) Further compounds, for example (15.001) benthiazole, (15.002) bethoxazin, (15.003) capsimycin, (15.004) carvone, (15.005) quinomethionate, (15.006) pyriofenone (chlazafenone), (15.007) cufraneb, (15.008) cyflufenamid, (15.009) cymoxanil, (15.010) cyprosulphamide, (15.011) dazomet, (15.012) debacarb, (15.013) dichlorophen, (15.014) diclomezin, (15.015) difenzoquat, (15.016) difenzoquat metilsulphate, (15.017) diphenylamine, (15.018) Ecomate, (15.019) fenpyrazamine, (15.020) flumetover, (15.021) fluoroimide, (15.022) flusulphamide, (15.023) flutianil, (15.024) fosetyl-aluminium, (15.025) fosetyl-calcium, (15.026) fosetyl-sodium, (15.027) hexachlorobenzene, (15.028) irumamycin, (15.029) methasulphocarb, (15.030) methyl isothiocyanate, (15.031) metrafenone, (15.032) mildiomycin, (15.033) natamycin, (15.034) nickel dimethyldithiocarbamate, (15.035) nitrothal-isopropyl, (15.036) oxamocarb, (15.037) oxyfenthiin, (15.038) pentachlorophenol and salts, (15.039) phenothrin, (15.040) phosphorous acid and salts thereof, (15.041) propamocarb-fosetylate, (15.042) propanosin-sodium, (15.043) pyrimorph, (15.044) pyrrolnitrin, (15.045) tebufloquin, (15.046) tecloftalam, (15.047) tolnifanid, (15.048) triazoxide, (15.049) trichlamid, (15.050) zarilamid, (15.051) 2-methylpropanoic acid (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl ester, (15.052) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.053) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.054) oxathiapiproline, (15.055) 1H-imidazole-1-carboxylic acid 1-(4-methoxyphenoxy)-3,3-dimethylbutan-2-yl ester, (15.056) 2,3,5,6-tetrachloro-4-(methylsulphonyl)pyridine, (15.057) 2,3-dibutyl-6-chlorothieno[2,3-d]pyrimidin-4(3H)-one, (15.058) 2,6-dimethyl-1H,5H-[1,4]dithiino[2,3-c:5,6-c']dipyrrole-1,3,5,7(2H,6H)-tetrone, (15.059) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.060) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, (15.061) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (15.062) 2-butoxy-6-iodo-3-propyl-4H-chromen-4-one, (15.063) 2-chloro-5-[2-chloro-1-(2,6-difluoro-4-methoxyphenyl)-4-methyl-1H-imidazol-5-yl]pyridine, (15.064) 2-phenylphenol and salts, (15.065) 3-(4,4,5-trifluoro-3,3-dimethyl-3,4-dihydroisoquinolin-1-yl)quinoline, (15.066) 3,4,5-trichloropyridine-2,6-dicarboxylic acid nitrile, (15.067) 3-chloro-5-(4-chlorophenyl)-4-(2,6-difluorophenyl)-6-methylpyridazine, (15.068) 4-(4-chlorophenyl)-5-(2,6-difluorophenyl)-3,6-dimethylpyridazine, (15.069) 5-amino-1,3,4-thiadiazole-2-thiol, (15.070) 5-chloro-N'-phenyl-N'-(prop-2-in-1-yl)thiophene-2-sulphonohydrazide, (15.071) 5-fluoro-2-[(4-fluorobenzyl)oxy]pyrimidin-4-amine, (15.072) 5-fluoro-2-[(4-methylbenzyl)oxy]pyrimidin-4-amin, (15.073) 5-methyl-6-octyl[1,2,4]triazolo[1,5-a]pyrimidin-7-amin, (15.074) (2Z)-3-amino-2-cyano-3-phenylacrylic acid ethyl ester, (15.075) N'-(4-{[3-(4-chlorobenzyl)-1,2,4-thiadiazol-5-yl]oxy}-2,5-dimethylphenyl)-N-ethyl-N-methylimidoformamide, (15.076) N-(4-chlorobenzyl)-3-[3-methoxy-4-(prop-2-in-1-yloxy)phenyl]propanamide, (15.077) N-[(4-chlorophenyl)(cyano)methyl]-3-[3-methoxy-4-(prop-2-in-1-yloxy)phenyl]propanamide, (15.078) N-[(5-bromo-3-chloropyridin-2-yl)methyl]-2,4-dichloronicotinamide, (15.079) N-[1-(5-bromo-3-chloropyridin-2-yl)ethyl]-2,4-dichloronicotinamide, (15.080) N-[1-(5-bromo-3-chloropyridin-2-yl)ethyl]-2-fluoro-4-iodonicotinamide, (15.081) N-{(E)-[(cyclopropylmethoxy)imino][6-(difluoromethoxy)-2,3-difluorophenyl]methyl}-2-phenylacetamide, (15.082) N-{(Z)-[(cyclopropylmethoxy)imino][6-(difluoromethoxy)-2,3-difluorophenyl]methyl}-2-phenylacetamide, (15.083) N'-{4-[(3-tert-butyl-4-cyano-1,2-thiazol-5-yl)oxy]-2-chloro-5-methylphenyl}-N-ethyl-N-methylimidoformamide, (15.084) N-methyl-2-(1-{[5-methyl-3-(trifluoromethyl)-1H-pyrazol-1-yl]acetyl}piperidin-4-yl)-N-(1,2,3,4-tetrahydronaphthalin-1-yl)-1,3-thiazole-4-carboxamide, (15.085) N-methyl-2-(1-{[5-methyl-3-(trifluoromethyl)-1H-pyrazol-1-yl]acetyl}piperidin-4-yl)-N-[(1R)-1,2,3,4-tetrahydronaphthalin-1-yl]-3-thiazole-4-carboxamide, (15.086) N-methyl-2-(1-{[5-methyl-3-(trifluoromethyl)-1H-pyrazol-1-yl]acetyl}piperidin-4-yl)-N-[(1S)-1,2,3,4-tetrahydronaphthalin-1-yl]-1,3-thiazole-4-carboxamide, (15.087) {6-[({[(1-methyl-H-tetrazol-5-yl)(phenyl)methylen]amino}oxy)methyl]pyridin-2-yl}carbamic acid pentyl ester, (15.088) phenazine-1-carboxylic acid, (15.089) quinolin-8-ol, (15.090) quinolin-8-ol sulphate (2:1), (15.091) {6-[({[(1-methyl-1H-tetrazol-5-yl)(phenyl)methylen]amino}oxy)methyl]pyridin-2-yl}carbamic acid tert-butyl ester, (15.092) (5-bromo-2-methoxy-4-methylpyridin-3-yl)(2,3,4-trimethoxy-6-methylphenyl)methanone, (15.093) N-[2-(4-{[3-(4-chlorophenyl)prop-2-yn-1-yl]oxy}-3-methoxyphenyl)ethyl]-N2-(methylsulphonyl)valinamide, (15.094) 4-oxo-4-[(2-phenylethyl)amino]butanoic acid, (15.095) {6-[({1 [(Z)-(1-methyl-1H-tetrazol-5-yl)(phenyl)methylen]amino}oxy)methyl]pyridin-2-yl}carbamic acid but-3-yn-1-yl ester, (15.096) 4-amino-5-fluoropyrimidin-2-ol (tautomeric form: 4-amino-5-fluoropyrimidin-2(1H)-one), (15.097) 3,4,5-trihydroxybenzoic acid propyl ester, (15.098) [3-(4-chloro-2-fluorophenyl)-5-(2,4-difluorophenyl)-1,2-oxazol-4-yl](pyridin-3-yl)methanol, (15.099) (S)-[3-(4-chloro-2-fluorophenyl)-5-(2,4-difluorophenyl)-1,2-oxazol-4-yl](pyridin-3-yl)methanol, (15.100) (R)-[3-(4-chloro-2-fluorophenyl)-5-(2,4-difluorophenyl)-1,2-oxazol-4-yl](pyridin-3-yl)methanol, (15.101) 2-fluoro-6-(trifluoromethyl)-N-(1,1,3-trimethyl-2,3-dihydro-1H-inden-4-yl)benzamide, (15.102) 2-(6-benzylpyridin-2-yl)quinazoline, (15.103) 2-[6-(3-fluoro-4-methoxyphenyl)-5-methylpyridin-2-yl]quinazoline, (15.104) 3-(4,4-difluoro-3,3-dimethyl-3,4-dihydroisoquinolin-1-yl)quinoline, (15.105) abscisic acid, (15.106) N'-[5-bromo-6-(2,3-dihydro-1H-inden-2-yloxy)-2-methylpyridin-3-yl]-N-ethyl-N-methylimidoformamide, (15.107) N'-{5-bromo-6-[1-(3,5-difluorophenyl)ethoxy]-2-methylpyridin-3-yl}-N-ethyl-N-etthylimidoformamide, (15.108) N'-{5-bromo-6-[(1R)-1-(3,5-difluorophenyl)ethoxy]-2-methylpyridin-3-yl}-N-ethyl-N-methylimidoformamide, (15.109) N'-{5-bromo-6-[(1S)-1-(3,5-difluorophenyl)ethoxy]-2-methylpyridin-3-yl}-N-ethyl-N-methylimidoformamide, (15.110) N'-{5-bromo-6-[(cis-4-isopropylcyclohexyl)oxy]-2-methylpyridin-3-yl}-N-ethyl-N-methylimidoformamide, (15.111) N'-{5-bromo-6-[(trans-4-isopropylcyclohexyl)oxy]-2-methylpyridin-3-yl}-N-ethyl-N-methylimidoformamide, (15.112) N-cyclopropyl-3-(difluoromethyl)-5-fluoro-N-(2-isopropylbenzyl)-1-methyl-1H-pyrazole-4-carboxamide, (15.113) N-cyclopropyl-N-(2-cyclopropylbenzyl)-3-(difluoromethyl)-5-fluoro-1-methyl-1H-pyrazole-4-carboxamide, (15.114) N-(2-tert-butylbenzyl)-N-cyclopropyl-3-(difluoromethyl)-5-fluoro-1-methyl-1H-pyrazole-4-carboxamide, (15.115) N-(5-chloro-2-ethylbenzyl)-N-cyclopropyl-3-(difluoromethyl)-5-fluoro-1-methyl-1H-pyrazole-4-carboxamide, (15.116) N-(5-chloro-2-isopropylbenzyl)-N-cyclopropyl-3-(difluoromethyl)-5-fluoro-1-methyl-1H-pyrazole-4-carboxamide, (15.117) N-cyclopropyl-3-(difluoromethyl)-N-(2-ethyl-5-fluorobenzyl)-5-fluoro-1-methyl-1H-pyrazole-4-carboxamide, (15.118) N-cyclopropyl-3-(difluoromethyl)-5-fluoro-N-(5-fluoro-2-isopropylbenzyl)-1-methyl-1H-pyrazole-4-carboxamide, (15.119) N-cyclopropyl-N-(2-cyclopropyl-5-fluorobenzyl)-3-(difluoromethyl)-5-fluoro-1-methyl-1H-pyrazole-4-carboxamide, (15.120) N-(2-cyclopentyl-5-fluorobenzyl)-N-cyclopropyl-3-(difluoromethyl)-5-fluoro-1-methyl-1H-pyrazole-4-carboxamide, (15.121) N-cyclopropyl-3-(difluoromethyl)-5-fluoro-N-(2-fluoro-6-isopropylbenzyl)-1-methyl-1H-pyrazole-4-carboxamide, (15.122) N-cyclopropyl-3-(difluoromethyl)-N-(2-ethyl-5-methylbenzyl)-5-fluoro-1- methyl-1H-pyrazole-4-carboxamide, (15.123) N-cyclopropyl-3-(difluoromethyl)-5-fluoro-N-(2-isopropyl-5-methylbenzyl)-1-methyl-1H-pyrazole-4-carboxamide, (15.124) N-cyclopropyl-N-(2-cyclopropyl-5-methylbenzyl)-3-(difluoromethyl)-5-fluoro-1-methyl-1H-pyrazole-4-carboxamide, (15.125) N-(2-tert-butyl-5-methylbenzyl)-N-cyclopropyl-3-(difluoromethyl)-5-fluoro-1-methyl-1H-pyrazole-4-carboxamide, (15.126) N-[5-chloro-2-(trifluoromethyl)benzyl]-N-cyclopropyl-3-(difluoromethyl)-5-fluoro-1-methyl-1H-pyrazole-4-carboxamide, (15.127) N-cyclopropyl-3-(difluoromethyl)-5-fluoro-1-methyl-N-[5-methyl-2-(trifluoromethyl)benzyl]-1H-pyrazole-4-carboxamide, (15.128) N-[2-chloro-6-(trifluoromethyl)benzyl]-N-cyclopropyl-3-(difluoromethyl)-5-fluoro-1-methyl-1H-pyrazole-4-carboxamide, (15.129) N-[3-chloro-2-fluoro-6-(trifluoromethyl)benzyl]-N-cyclopropyl-3-(difluoromethyl)-5-fluoro-1-methyl-1H-pyrazole-4-carboxamide, (15.130) N-cyclopropyl-3-(difluoromethyl)-N-(2-ethyl-4,5-dimethylbenzyl)-5-fluoro-1-methyl-1H-pyrazole-4-carboxamide, (15.131) N-cyclopropyl-3-(difluoromethyl)-5-fluoro-N-(2-isopropylbenzyl)-1-methyl-1H-pyrazole-4-carbothioamide, (15.132) N'-(2,5-dimethyl-4-phenoxyphenyl)-N-ethyl-N-methylimidoformamide, (15.133) N'-{4-[(4,5-dichloro-1,3-thiazol-2-yl)oxy]-2,5-dimethylphenyl}-N-ethyl-N-methylimidoformamide, (15.134) N-(4-chloro-2,6-difluorophenyl)-4-(2-chloro-4-fluorophenyl)-1,3-dimethyl-1H-pyrazol-5-amine, (15.135) 9-fluoro-2,2-dimethyl-5-(quinolin-3-yl)-2,3-dihydro-1,4-benzoxazepine, (15.136) 2-{2-fluoro-6-[(8-fluoro-2-methylquinolin-3-yl)oxy]phenyl}propan-2-ol, (15.137) 2-{2-[(7,8-difluoro-2-methylquinolin-3-yl)oxy]-6-fluorophenyl}propan-2-ol, (15.138) 4-(2-chloro-4-fluorophenyl)-N-(2-fluorophenyl)-1,3-dimethyl-1H-pyrazol-5-amine, (15.139) 4-(2-chloro-4-fluorophenyl)-N-(2,6-difluorophenyl)-1,3-dimethyl-1H-pyrazol-5-amine, (15.140) 4-(2-chloro-4-fluorophenyl)-N-(2-chloro-6-fluorophenyl)-1,3-dimethyl-1H-pyrazol-5-amine, (15.141) 4-(2-bromo-4-fluorophenyl)-N-(2-chloro-6-fluorophenyl)-1,3-dimethyl-1H-pyrazol-5-amine, (15.142) N-(2-bromo-6-fluorophenyl)-4-(2-chloro-4-fluorophenyl)-1,3-dimethyl-1H-pyrazol-5-amine, (15.143) 4-(2-bromo-4-fluorophenyl)-N-(2-bromophenyl)-1,3-dimethyl-1H-pyrazol-5-amine, (15.144) 4-(2-bromo-4-fluorophenyl)-N-(2-bromo-6-fluorophenyl)-1,3-dimethyl-1H-pyrazol-5-amine, (15.145) 4-(2-bromo-4-fluorophenyl)-N-(2-chlorophenyl)-1,3-dimethyl-1H-pyrazol-5-amine, (15.146) N-(2-bromophenyl)-4-(2-chloro-4-fluorophenyl)-1,3-dimethyl-1H-pyrazol-5-amine, (15.147) 4-(2-chloro-4-fluorophenyl)-N-(2-chlorophenyl)-1,3-dimethyl-1H-pyrazol-5-amine, (15.148) 4-(2-bromo-4-fluorophenyl)-N-(2,6-difluorophenyl)-1,3-dimethyl-1H-pyrazol-5-amine, (15.149) 4-(2-bromo-4-fluorophenyl)-N-(2-fluorophenyl)-1,3-dimethyl-1H-pyrazol-5-amine, (15.150) N'-(4-{3-[(difluoromethyl)sulfanyl]phenoxy}-2,5-dimethylphenyl)-N-ethyl-N-methylimidoformamide, (15.151) N'-(2,5-dimethyl-4-{3-[(1,1,2,2-tetrafluoroethyl)sulfanyl]phenoxy}phenyl)-N-ethyl-N-methylimidoformamide, (15.152) N'-(2,5-dimethyl-4-{3-[(2,2,2-trifluoroethyl)sulfanyl]phenoxy}phenyl)-N-ethyl-N-methylimidoformamide, (15.153) N'-(2,5-dimethyl-4-{3-[(2,2,3,3-tetrafluoropropyl)sulfanyl]phenoxy}phenyl)-N-ethyl-N-methylimidoformamide, (15.154) N'-(2,5-dimethyl-4-{3-[(pentafluoroethyl)sulfanyl]phenoxy}phenyl)-N-ethyl-N-methylimidoformamide, (15.155) N'-(4-{[3-(difluoromethoxy)phenyl]sulfanyl}-2,5-dimethylphenyl)-N-ethyl-N-methylimidoformamide, (15.156) N'-(2,5-dimethyl-4-{[3-(1,1,2,2-tetrafluoroethoxy)phenyl] sulfanyl}phenyl)-N-ethyl-N-methylimidoformamide, (15.157) N'-(2,5-dimethyl-4-{[3-(2,2,2-trifluoroethoxy)phenyl]sulfanyl}phenyl)-N-ethyl-N-methylimidoformamide, (15.158) N'-(2,5-dimethyl-4-{[3-(2,2,3,3-tetrafluoropropoxy)phenyl]sulfanyl}phenyl)-N-ethyl-N-methylimidoformamide, (15.159) N'-(2,5-dimethyl-4-{[3-(pentafluoroethoxy)phenyl]sulfanyl}phenyl)-N-ethyl-N-methylimidoformamide, (15.160) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.161) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.162) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.163) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenylmethanesulphonate, (15.164) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate, (15.165) 2-[3,5-bis(difluoromethyl)-1H-pyrazol-1-yl]-1-[4-(4-{(5S)-5-[2-(prop-2-yn-1-yloxy)phenyl]-4,5-dihydro-1,2-oxazol-3-yl}-1,3-thiazol-2-yl)piperidin-1-yl]ethanone, (15.166) 2-[3,5-bis(difluoromethyl)-1H-pyrazol-1-yl]-1-[4-(4-{(5R)-5-[2-(prop-2-yn-1-yloxy)phenyl]-4,5-dihydro-1,2-oxazol-3-yl}-1,3-thiazol-2-yl)piperidin-1-yl]ethanone, (15.167) 2-[3,5-bis(difluoromethyl)-1H-pyrazol-1-yl]-1-[4-(4-{(5S)-5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.168) 2-[3,5-bis(difluoromethyl)-1H-pyrazol-1-yl]-1-[4-(4-{(5R)-5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.169) 2-[3,5-bis(difluoromethyl)-1H-pyrazol-1-yl]-1-[4-(4-{(5S)-5-[2-chloro-6-(prop-2-yn-1-yloxy)phenyl]-4,5-dihydro-1,2-oxazol-3-yl}-1,3-thiazol-2-yl)piperidin-1-yl]ethanone, (15.170) 2-[3,5-bis(difluoromethyl)-1H-pyrazol-1-yl]-1-[4-(4-{(5R)-5-[2-chloro-6-(prop-2-yn-1-yloxy)phenyl]-4,5-dihydro-1,2-oxazol-3-yl}-1,3-thiazol-2-yl)piperidin-1-yl]ethanone, (15.171) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenylmethanesulphonate, (15.172) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenylmethanesulphonate, (15.173) 2-{(5S)-3-[2-(1-({[3,5-bis(difluoromethyl)-1H-pyrazol-1-yl] acetyl}piperidin-4-yl)-1,3-thiazol-4-yl]-4,5-dihydro-1,2-oxazol-5-yl}-3-chlorophenylmethanesulphonate, (15.174) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate.

Biological Pesticides as Mixing Components

The compounds of the formula (I) can be combined with biological pesticides.

Biological pesticides include especially bacteria, fungi, yeasts, plant extracts and products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which are used or can be used as biological pesticides are:

*Bacillus amyloliquefaciens*, strain FZB42 (DSM 231179), or *Bacillus cereus*, especially *B. cereus* strain CNCM I-1562 or

*Bacillus firmus*, strain I-1582 (Accession number CNCM I-1582) or *Bacillus pumilus*, especially strain GB34 (Accession No. ATCC 700814) and strain QST2808 (Accession No. NRRL B-30087), or *Bacillus subtilis*, especially strain GB03 (Accession No. ATCC SD-1397), or *Bacillus subtilis* strain QST713 (Accession No. NRRL B-21661) or *Bacillus subtilis* strain OST 30002 (Accession No. NRRL B-50421) *Bacillus thuringiensis*, especially *B. thuringiensis* subspecies *israelensis* (serotype H-14), strain AM65-52 (Accession No. ATCC 1276), or *B. thuringiensis* subsp. *aizawai*, especially strain ABTS-1857 (SD-1372), or *B. thuringiensis* subsp. *kurstaki* strain HD-1, or *B. thuringiensis* subsp. *tenebrionis* strain NB 176 (SD-5428), *Pasteuria penetrans*, *Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are used or can be used as biological pesticides are:
*Beauveria bassiana*, in particular strain ATCC 74040, *Coniothyrium minitans*, in particular strain CON/M/91-8 (Accession No. DSM-9660), *Lecanicillium* spp., in particular strain HRO LEC 12, *Lecanicillium lecanii*, (formerly known as *Verticillium lecanii*), in particular strain KV01, *Metarhizium anisopliae*, in particular strain F52 (DSM3884/ATCC 90448), *Metschnikowia fructicola*, in particular strain NRRL Y-30752, *Paecilomyces fumosoroseus* (new: *Isaria fumosorosea*), in particular strain IFPC 200613, or strain Apopka 97 (Accession No. ATCC 20874), *Paecilomyces lilacinus*, in particular *P. lilacinus* strain 251 (AGAL 89/030550), *Talaromyces flavus*, in particular strain V117b, *Trichoderma atroviride*, in particular strain SC1 (Accession Number CBS 122089), *Trichoderma harzianum*, in particular *T. harzianum rifai* T39 (Accession Number CNCM 1-952).

Examples of viruses which are used or can be used as biological pesticides are:
*Adoxophyes orana* (summer fruit tortrix) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples which may be mentioned are:
*Agrobacterium* spp., *Azorhizobium caulinodans*, *Azospirillum* spp., *Azotobacter* spp., *Bradyrhizobium* spp., *Burkholderia* spp., especially *Burkholderia cepacia* (formerly known as *Pseudomonas cepacia*), *Gigaspora* spp., or *Gigaspora monosporum*, *Glomus* spp., *Laccaria* spp., *Lactobacillus buchneri*, *Paraglomus* spp., *Pisolithus tinctorus*, *Pseudomonas* spp., *Rhizobium* spp., especially *Rhizobium trifolii*, *Rhizopogon* spp., *Scleroderma* spp., *Suillus* spp., *Streptomyces* spp.

Examples of plant extracts and products formed by microorganisms, including proteins and secondary metabolites, which are used or can be used as biological pesticides are:
*Allium sativum*, *Artemisia absinthium*, azadirachtin, Biokeeper WP, *Cassia nigricans*, *Celastrus angulatus*, *Chenopodium anthelminticum*, chitin, Armour-Zen, *Dryopteris filix-mas*, *Equisetum arvense*, Fortune Aza, Fungastop, Heads Up (*Chenopodium quinoa* saponin extract), Pyrethrum/Pyrethrins, *Quassia amara*, *Quercus*, *Quillaja*, Regalia, "Requiem™ Insecticide", rotenone, ryania/ryanodine, *Symphytum officinale*, *Tanacetum vulgare*, thymol, Triact 70, TriCon, *Tropaeulum majus*, *Urtica dioica*, Veratrin, *Viscum album*, Brassicaceae extract, especially oilseed rape powder or mustard powder.

Safeners as Mixing Components

The compounds of the formula (I) can be combined with safeners, for example benoxacor, cloquintocet (-mexyl), cyometrinil, cyprosulphamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino] phenyl}sulphonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Plants are understood here to mean all plants and populations of plants, such as desirable and undesirable wild plants or crop plants (including naturally occurring crop plants), for example cereals (wheat, rice, triticale, barley, rye, oats), maize, soya bean, potato, sugar beet, sugar cane, tomatoes, bell peppers and chili peppers, cucumbers, melons, carrots, water melons, onions, lettuce, spinach, leeks, beans, *Brassica oleracea* (e.g. cabbage) and other vegetable species, cotton, tobacco, oilseed rape, and also fruit plants (with the fruits apples, pears, citrus fruits and grapes). Crop plants may be plants which can be obtained by conventional breeding and optimization methods or by biotechnological and genetic engineering methods or combinations of these methods, including the transgenic plants and including the plant cultivars which are protectable or non-protectable by plant breeders' rights. Plants shall be understood to mean all developmental stages of the plants, for example seeds, cuttings and young (immature) plants up to mature plants. Plant parts shall be understood to mean all parts and organs of the plants above and below ground, such as shoot, leaf, flower and root, examples given being leaves, needles, stalks, stems, flowers, fruit bodies, fruits and seeds, and also roots, tubers and rhizomes. Plant parts also include harvested material (harvested plants or plant parts) and vegetative and generative propagation material, for example cuttings, tubers, rhizomes, slips and seeds.

Treatment according to the invention of the plants and plant parts with the compounds of the formula (I) is carried out directly or by allowing the compounds to act on their surroundings, habitat or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and parts thereof in accordance with the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having new properties ("traits")

and which have been grown by conventional breeding, by mutagenesis or by recombinant DNA techniques. They may be cultivars, varieties, biotypes or genotypes.

Transgenic Plants, Seed Treatment and Integration Events

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, better storage life and/or processability of the harvested products. Further and particularly emphasized examples of such properties are increased resistance of the plants against animal and microbial pests, such as insects, arachnids, nematodes, mites, slugs and snails owing, for example, to toxins formed in the plants, in particular those produced in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof), and also increased resistance of the plants against phytopathogenic fungi, bacteria and/or viruses caused, for example, by systemic acquired resistance (SAR), systemin, phytoalexins, elicitors and resistance genes and correspondingly expressed proteins and toxins, and also increased tolerance of the plants to certain herbicidally active compounds, for example imidazolinones, sulphonylureas, glyphosates or phosphinothricin (for example the "PAT" gene). The genes which impart the desired properties ("traits") in question may also be present in combinations with one another in the transgenic plants. Examples of transgenic plants include the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), particular emphasis being given to maize, soya beans, wheat, rice, potatoes, cotton, sugar cane, tobacco and oilseed rape. Properties ("traits") which are particularly emphasized are the increased resistance of the plants to insects, arachnids, nematodes and slugs and snails.

Crop Protection—Types of Treatment

The plants and plant parts are treated with the compounds of the formula (I) directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, additionally by dry seed treatment, liquid seed treatment, slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, i.e. compounds of the formula (I) are applied to the foliage, where treatment frequency and the application rate should be adjusted according to the level of infestation with the pest in question.

In the case of systemically active compounds, the compounds of the formula (I) also access the plants via the root system. The plants are then treated by the action of the compounds of the formula (I) on the habitat of the plant. This can be accomplished, for example, by drenching, or by mixing into the soil or the nutrient solution, meaning that the locus of the plant (e.g. soil or hydroponic systems) is impregnated with a liquid form of the compounds of the formula (I), or by soil application, meaning that the compounds of the formula (I) are introduced in solid form (e.g. in the form of granules) into the locus of the plants. In the case of paddy rice crops, this can also be accomplished by metering the compound of the formula (I) in a solid application form (for example as granules) into a flooded paddy field.

Seed Treatment

The control of animal pests by the treatment of the seed of plants has long been known and is the subject of constant improvements. Nevertheless, the treatment of seed entails a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is additionally desirable to optimize the amount of active compound used so as to provide optimum protection for the seed and the germinating plant from attack by animal pests, but without damage to the plant itself by the active compound used. In particular, methods for the treatment of seed should also take account of the intrinsic insecticidal or nematicidal properties of pest-resistant or -tolerant transgenic plants in order to achieve optimal protection of the seed and the germinating plant with a minimum expenditure on pesticides.

The present invention therefore in particular also relates to a method for the protection of seed and germinating plants from attack by pests, by treating the seed with one of the compounds of the formula (I). The method according to the invention for protecting seed and germinating plants against attack by pests further comprises a method in which the seed is treated simultaneously in one operation or sequentially with a compound of the formula (I) and a mixing component. It further also comprises a method where the seed is treated at different times with a compound of the formula (I) and a mixing component.

The invention likewise relates to the use of the compounds of the formula (I) for the treatment of seed for protecting the seed and the resulting plant from animal pests.

The invention further relates to seed which has been treated with a compound of the formula (I) for protection from animal pests. The invention also relates to seed which has been treated simultaneously with a compound of the formula (I) and a mixing component. The invention further relates to seed which has been treated at different times with a compound of the formula (I) and a mixing component. In the case of seed which has been treated at different times with a compound of the formula (I) and a mixing component, the individual substances may be present on the seed in different layers. In this case, the layers comprising a compound of the formula (I) and a mixing component may optionally be separated by an intermediate layer. The invention also relates to seed in which a compound of the formula (I) and a mixing component have been applied as part of a coating or as a further layer or further layers in addition to a coating.

The invention further relates to seed which, after the treatment with a compound of the formula (I), is subjected to a film-coating process to prevent dust abrasion on the seed.

One of the advantages encountered with a systemically acting compound of the formula (I) is the fact that, by treating the seed, not only the seed itself but also the plants resulting therefrom are, after emergence, protected against animal pests. In this way, the immediate treatment of the crop at the time of sowing or shortly thereafter can be dispensed with.

A further advantage is that the treatment of the seed with a compound of the formula (I) can enhance germination and emergence of the treated seed.

It is likewise considered to be advantageous that compounds of the formula (I) can especially also be used for transgenic seed.

Furthermore, compounds of the formula (I) can be employed in combination with compositions of signalling technology, leading to better colonization by symbionts such as, for example, rhizobia, mycorrhizae and/or endophytic bacteria or fungi, and/or to optimized nitrogen fixation.

The compounds of the formula (I) are suitable for protection of seed of any plant variety which is used in agriculture, in the greenhouse, in forests or in horticulture. More particularly, this includes seed of cereals (for example wheat, barley, rye, millet and oats), maize, cotton, soya beans, rice, potatoes, sunflowers, coffee, tobacco, canola, oilseed rape, beet (for example sugar beet and fodder beet), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya beans, cotton, canola, oilseed rape, vegetables and rice.

As already mentioned above, the treatment of transgenic seed with a compound of the formula (I) is also of particular importance. This involves the seed of plants which generally contain at least one heterologous gene which controls the expression of a polypeptide having insecticidal and/or nematicidal properties in particular. The heterologous genes in transgenic seed may originate in this case from microorganisms such as *Bacillus, Rhizobium, Pseudomonas, Serratia, Trichoderma, Clavibacter, Glomus* or *Gliocladium*. The present invention is particularly suitable for the treatment of transgenic seed containing at least one heterologous gene originating from *Bacillus* sp. The heterologous gene is more preferably derived from *Bacillus thuringiensis*.

In the context of the present invention, the compound of the formula (I) is applied to the seed. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which has been pre-swollen in water up to a certain stage (pigeon breast stage) for example, which leads to improved germination and more uniform emergence.

When treating the seed, care must generally be taken that the amount of the compound of the formula (I) applied to the seed and/or the amount of further additives is chosen in such a way that the germination of the seed is not adversely affected, or that the resulting plant is not damaged. This has to be ensured particularly in the case of active compounds which can exhibit phytotoxic effects at certain application rates.

In general, the compounds of the formula (I) are applied to the seed in the form of a suitable formulation. Suitable formulations and processes for seed treatment are known to the person skilled in the art.

The compounds of the formula (I) can be converted to the customary seed-dressing formulations, such as solutions, emulsions, suspensions, powders, foams, slurries or other coating compositions for seed, and also ULV formulations.

These formulations are prepared in a known manner, by mixing compounds of the formula (I) with customary additives such as, for example, customary extenders and also solvents or diluents, dyes, wetting agents, dispersants, emulsifiers, antifoams, preservatives, secondary thickeners, adhesives, gibberellins and also water.

Dyes which may be present in the seed-dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed-dressing formulations usable in accordance with the invention are all substances which promote wetting and which are customary for the formulation of agrochemically active compounds. Alkyl naphthalenesulphonates, such as diisopropyl or diisobutyl naphthalenesulphonates, can be used with preference.

Suitable dispersants and/or emulsifiers which may be present in the seed-dressing formulations usable in accordance with the invention are all nonionic, anionic and cationic dispersants customary for the formulation of agrochemically active compounds. Nonionic or anionic dispersants or mixtures of nonionic or anionic dispersants can be used with preference. Suitable nonionic dispersants include in particular ethylene oxide/propylene oxide block polymers, alkylphenol polyglycol ethers and tristyrylphenol polyglycol ethers, and the phosphated or sulphated derivatives thereof. Suitable anionic dispersants are especially lignosulphonates, polyacrylic acid salts and arylsulphonate-formaldehyde condensates.

Antifoams which may be present in the seed-dressing formulations usable in accordance with the invention are all foam-inhibiting substances customary for the formulation of agrochemically active compounds. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Secondary thickeners which may be present in the seed-dressing formulations usable in accordance with the invention are all substances which can be used for such purposes in agrochemical compositions. Preferred examples include cellulose derivatives, acrylic acid derivatives, xanthan, modified clays and finely divided silica.

Useful stickers which may be present in the seed-dressing formulations usable in accordance with the invention are all customary binders usable in seed-dressing products. Preferred examples include polyvinylpyrrolidone, polyvinyl acetate, polyvinyl alcohol and tylose.

Gibberellins which may be present in the seed-dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz-und Schädlingsbekämpfungsmittel", vol. 2, Springer Verlag, 1970, pp. 401-412).

The seed-dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats, and triticale, and also the seed of maize, rice, oilseed rape, peas, beans, cotton, sunflowers, soya beans and beets, or else a wide variety of different vegetable seed. The seed-dressing formulations usable in accordance with the invention, or the dilute use forms thereof, can also be used to dress seed of transgenic plants.

For the treatment of seed with the seed-dressing formulations usable in accordance with the invention, or use forms prepared therefrom, all mixing units usable customarily for the seed dressing are useful.

Specifically, the procedure in seed dressing is to place the seed into a mixer in batchwise or continuous operation, to add the particular desired amount of seed-dressing formulations, either as such or after prior dilution with water, and to mix until the formulation is distributed homogeneously on the seed. If appropriate, this is followed by a drying operation.

The application rate of the seed dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. the field of veterinary medicine, the compounds of the formula (I) are active against animal parasites, in particular ectoparasites or endoparasites. The term "endoparasites" includes especially helminths and protozoa, such as coccidia. Ectoparasites are typically and preferably arthropods, especially insects and acarids.

In the field of veterinary medicine, the compounds of the formula (I) having favourable homeotherm toxicity are suitable for controlling parasites which occur in animal breeding and animal husbandry in livestock, breeding animals, zoo animals, laboratory animals, experimental animals and domestic animals. They are active against all or specific stages of development of the parasites.

Agricultural livestock include, for example, mammals such as sheep, goats, horses, donkeys, camels, buffalo, rabbits, reindeer, fallow deer, and particularly cattle and pigs; poultry such as turkeys, ducks, geese, and particularly chickens; fish and crustaceans, for example in aquaculture, and also insects such as bees.

Domestic animals include, for example, mammals, such as hamsters, guinea pigs, rats, mice, chinchillas, ferrets, and particularly dogs, cats, caged birds, reptiles, amphibians and aquarium fish.

In a preferred embodiment, the compounds of the formula (I) are administered to mammals.

In another preferred embodiment, the compounds of the formula (I) are administered to birds, namely caged birds and particularly poultry.

Use of the compounds of the formula (I) for the control of animal parasites is intended to reduce or prevent illness, cases of death and reductions in performance (in the case of meat, milk, wool, hides, eggs, honey and the like), such that more economical and simpler animal husbandry is enabled and better animal well-being is achievable.

In relation to the field of animal health, the term "control" or "controlling" means that the compounds of the formula (I) are effective in reducing the incidence of the particular parasite in an animal infected with such parasites to an innocuous degree. More specifically, "controlling" in the present context means that the compound of the formula (I) can kill the respective parasite, inhibit its growth, or inhibit its proliferation.

Arthropods include:

from the order Anoplurida, for example *Haematopinus* spp., *Linognathus* spp., *Pediculus* spp., *Phtirus* spp., *Solenopotes* spp.; from the order Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; from the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; from the order Siphonapterida, for example *Pulex* spp., *Ctenocephalides* spp., *Tunga* spp., *Xenopsylla* spp., *Ceratophyllus* spp.;

from the order Heteropterida, for example *Cimex* spp., *Triatoma* spp., *Rhodnius* spp., *Panstrongylus* spp.; and also nuisance and hygiene pests from the order Blattarida.

Arthropods further include:

from the subclass Acari (Acarina) and the order Metastigmata, for example from the family Argasidae like *Argas* spp., *Ornithodorus* spp., *Otobius* spp., from the family Ixodidae like *Ixodes* spp., *Amblyomma* spp., *Rhipicephalus* (*Boophilus*) spp., *Dermacentor* spp., *Haemophysalis* spp., *Hyalomma* spp., *Rhipicephalus* spp. (the original genus of multi-host ticks); from the order Mesostigmata like *Dermanyssus* spp., *Ornithonyssus* spp., *Pneumonyssus* spp., *Raillietia* spp., *Pneumonyssus* spp., *Sternostoma* spp., *Varroa* spp., *Acarapis* spp.; from the order Actinedida (Prostigmata), for example *Acarapis* spp., *Cheyletiella* spp., *Ornithocheyletia* spp., *Myobia* spp., *Psorergates* spp., *Demodex* spp., *Trombicula* spp., *Neotrombiculla* spp., *Listrophorus* spp.; and from the order Acaridida (Astigmata), for example *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

Parasitic protozoa include:

Mastigophora (*Flagellata*), for example Trypanosomatidae, for example *Trypanosoma b. brucei, T. b. gambiense, T. b. rhodesiense, T. congolense, T. cruzi, T. evansi, T. equinum, T. lewisi, T. percae, T. simiae, T. vivax, Leishmania brasiliensis, L. donovani, L. tropica*, for example Trichomonadidae, for example *Giardia lamblia, G. canis*;

Sarcomastigophora (Rhizopoda) such as Entamoebidae, for example *Entamoeba histolytica*, Hartmanellidae, for example *Acanthamoeba* sp., *Harmanella* sp.;

Apicomplexa (Sporozoa) such as Eimeridae, for example *Eimeria acervulina, E. adenoides, E. alabamensis, E. anatis, E. anserina, E. arloingi, E. ashata, E. auburnensis, E. bovis, E. brunetti, E. canis, E. chinchillae, E. clupearum, E. columbae, E. contorta, E. crandalis, E. debliecki, E. dispersa, E. ellipsoidales, E. falciformis, E. faurei, E. flavescens, E. gallopavonis, E. hagani, E. intestinalis, E. iroquoina, E. irresidua, E. labbeana, E. leucarti, E. magna, E. maxima, E. media, E. meleagridis, E. meleagrimitis, E. mitis, E. necatrix, E. ninakohlyakimovae, E. ovis, E. parva, E. pavonis, E. perforans, E. phasani, E. piriformis, E. praecox, E. residua, E. scabra, E.* spec., *E. stiedai, E. suis, E. tenella, E. truncata, E. truttae, E. zuernii, Globidium* spec., *Isospora belli, I. canis, I. felis, I. ohioensis, I. rivolta, I.* spec., *I. suis, Cystisospora* spec., *Cryptosporidium* spec., in particular *C. parvum*; such as Toxoplasmadidae, for example *Toxoplasma gondii, Hammondia heydornii, Neospora caninum, Besnoitia besnoitii*; such as Sarcocystidae, for example *Sarcocystis bovicanis, S. bovihominis, S. ovicanis, S. ovifelis, S. neurona, S.* spec., *S. suihominis*, such as Leucozoidae, for example *Leucozytozoon simondi*, such as Plasmodiidae, for example *Plasmodium berghei, P. falciparum, P. malariae, P. ovale, P. vivax, P.* spec., such as Piroplasmea, for example *Babesia argentina, B. bovis, B. canis, B.* spec., *Theileria parva, Theileria* spec., such as Adeleina, for example *Hepatozoon canis, H.* spec.

Pathogenic endoparasites which are helminths include Platyhelmintha (e.g. Monogenea, cestodes and trematodes), nematodes, Acanthocephala, and Pentastoma. These include:

Monogenea: for example: *Gyrodactylus* spp., *Dactylogyrus* spp., *Polystoma* spp.;

Cestodes: from the order Pseudophyllidea for example: *Diphyllobothrium* spp., *Spirometra* spp., *Schistocephalus* spp., *Ligula* spp., *Bothridium* spp., *Diphlogonoporus* spp.; from the order Cyclophyllida, for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.;

trematodes: from the class Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fascioloides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp.;

Nematodes: Trichinellida, for example: *Trichuris* spp., *Capillaria* spp., *Paracapillaria* spp., *Eucoleus* spp., *Trichomosoides* spp., *Trichinella* spp.;

from the order Tylenchida, for example: *Micronema* spp., *Strongyloides* spp.;

from the order Rhabditida, for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Necator* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp., *Parelaphostrongylus* spp., *Crenosoma* spp., *Paracrenosoma* spp., *Oslerus* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Teladorsagia* spp., *Marshallagia* spp., *Cooperia* spp., *Nippostrongylus* spp., *Heligmosomoides* spp., *Nematodirus* spp., *Hyostrongylus* spp., *Obeliscoides* spp., *Amidostomum* spp., *Ollulanus* spp;

from the order Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp., *Spirocerca* spp.;

Acanthocephala: from the order Oligacanthorhynchida, for example: *Macracanthorhynchus* spp., *Prosthenorchis* spp.; from the order Polymorphida for example: *Filicollis* spp.; from the order Moniliformida for example: *Moniliformis* spp.;

from the order Echinorhynchida, for example *Acanthocephalus* spp., *Echinorhynchus* spp., *Leptorhynchoides* spp.;

Pentastoma: from the order Porocephalida, for example *Linguatula* spp.

In the veterinary field and in animal husbandry, the compounds of the formula (I) are administered by methods generally known in the art, such as via the enteral, parenteral, dermal or nasal route in the form of suitable preparations. Administration may be prophylactic or therapeutic.

Thus, one embodiment of the present invention refers to the use of a compound of the formula (I) as a medicament.

A further aspect refers to the use of a compound of the formula (I) as an antiendoparasitic agent, in particular a helminthicidal agent or antiprotozoic agent. Compounds of the formula (I) are suitable for use as an antiendoparasitic agent, especially as a helminthicidal agent or antiprotozoic agent, for example in animal breeding, in animal husbandry, in animal houses and in the hygiene sector.

A further aspect in turn relates to the use of a compound of the formula (I) as an antiectoparasitic agent, in particular an arthropodicide such as an insecticide or an acaricide. A further aspect relates to the use of a compound of the formula (I) as an antiectoparasitic agent, in particular an arthropodicide such as an insecticide or an acaricide, for example in animal husbandry, in animal breeding, in animal houses or in the hygiene sector.

Anthelmintic Mixing Components

The following anthelmintic mixing components may be mentioned by way of example:

anthelmintically active compounds including trematicidally and cestocidally active compounds:

from the class of the macrocyclic lactones, for example: abamectin, doramectin, emamectin, eprinomectin, ivermectin, milbemycin, moxidectin, nemadectin, selamectin;

from the class of the benzimidazoles and probenzimidazoles, for example: albendazole, albendazole-sulphoxide, cambendazole, cyclobendazole, febantel, fenbendazole, flubendazole, mebendazole, netobimin, oxfendazole, oxibendazole, parbendazole, thiabendazole, thiophanate, triclabendazole;

from the class of the cyclooctadepsipeptides, for example: emodepside, PF1022;

from the class of the aminoacetonitrile derivatives, for example: monepantel;

from the class of the tetrahydropyrimidines, for example: morantel, pyrantel, oxantel;

from the class of the imidazothiazoles, for example: butamisole, levamisole, tetramisole;

from the class of the salicylanilides, for example: bromoxanide, brotianide, clioxanide, closantel, niclosamide, oxyclozanide, rafoxanide, tribromsalan;

from the class of the paraherquamides, for example: derquantel, paraherquamide;

from the class of the aminophenylamidines, for example: amidantel, deacylated amidantel (dAMD), tribendimidine;

from the class of the organophosphates, for example: coumaphos, crufomate, dichlorvos, haloxone, naphthalofos, trichlorfon;

from the class of the substituted phenols, for example: bithionol, disophenol, hexachlorophene, niclofolan, meniclophalan, nitroxynil;

from the class of the piperazinones, for example: praziquantel, epsiprantel;

from various other classes, for example: amoscanate, bephenium, bunamidine, clonazepam, clorsulon, diamfenetid, dichlorophen, diethylcarbamazine, emetine, hetolin, hycanthone, lucanthone, Miracil, mirasan, niclosamide, niridazole, nitroxynil, nitroscanate, oltipraz, omphalotin, oxamniquin, paromomycin, piperazine, resorantel.

Vector Control

The compounds of the formula (I) can also be used in vector control. In the context of the present invention, a vector is an arthropod, especially an insect or arachnid, capable of transmitting pathogens, for example viruses, worms, single-cell organisms and bacteria, from a reservoir (plant, animal, human, etc.) to a host. The pathogens can be transmitted either mechanically (for example trachoma by non-stinging flies) to a host or after injection (for example malaria parasites by mosquitoes) into a host.

Examples of vectors and the diseases or pathogens they transmit are:

1) Mosquitoes
   *Anopheles*: malaria, filariasis;
   *Culex*: Japanese encephalitis, filariasis, other viral diseases, transmission of worms;
   *Aedes*: yellow fever, dengue fever, filariasis, other viral diseases;
   Simuliidae: transmission of worms, in particular *Onchocerca volvulus*;
2) Lice: skin infections, epidemic typhus;
3) Fleas: plague, endemic typhus;
4) Flies: sleeping sickness (trypanosomiasis); cholera, other bacterial diseases;
5) Mites: acariosis, epidemic typhus, rickettsialpox, tularaemia, Saint Louis encephalitis, tick-borne encephalitis (TBE), Crimean-Congo haemorrhagic fever, borreliosis;
6) Ticks: borellioses such as *Borrelia duttoni*, tick-borne encephalitis, Q fever (*Coxiella burnetii*), babesioses (*Babesia canis canis*).

Examples of vectors in the context of the present invention are insects, such as aphids, flies, leafhoppers or thrips, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles*, for example *A. gambiae, A. arabiensis, A. funestus, A. dirus* (malaria) and *Culex*, lice, fleas, flies, mites and ticks, which can transmit pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in forests, in gardens and in leisure facilities, and also in the protection of materials and stored products.

Protection of Industrial Materials

The compounds of the formula (I) are suitable for protecting industrial materials against attack or destruction by insects, for example from the orders Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In a further embodiment, the compounds of the formula (I) are used together with at least one further insecticide and/or at least one fungicide.

In a further embodiment, the compounds of the formula (I) are present as a ready-to-use pesticide, i.e. it can be applied to the material in question without further modifications. Suitable further insecticides or fungicides are in particular those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. It is equally possible to use the compounds of the formula (I), alone or in combinations with other active compounds, as antifouling agents.

Control of Animal Pests in the Hygiene Sector

The compounds of the formula (I) are suitable for controlling animal pests in the hygiene sector. More particularly, the invention can be used in the domestic protection sector, in the hygiene protection sector and in the protection of stored products, particularly for control of insects, arachnids and mites encountered in enclosed spaces, for example dwellings, factory halls, offices, vehicle cabins. For controlling animal pests, the compounds of the formula (I) are used alone or in combination with other active compounds and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is effected, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or bait stations.

PREPARATION EXAMPLES

Example I-30

2-{3-(Ethylsulfonyl)-6-[1-(pyridin-3-yl)-1H-pyrazol-3-yl]pyridin-2-yl}-3-methyl-6-(trifluoromethyl)-3H-imidazo[4,5-c]pyridine

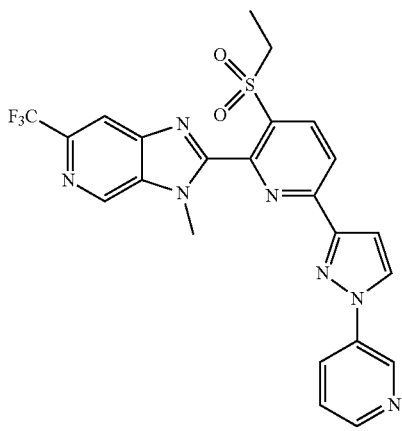 [SMILES: CCS(=O)(=O)c1ccc(-c2ccn(-c3cccnc3)n2)nc1-c1nc2cc(C(F)(F)F)ncc2n1C]

100 mg (0.24 mmol) of 2-(6-chloro-3-ethylsulfonyl-2-pyridyl)-3-methyl-6-(trifluoromethyl)imidazo[4,5-c]pyridine, 47 mg (0.24 mmol) of [1-(pyridin-3-yl)-1H-pyrazol-3-yl]boric acid (for the synthesis of the corresponding boronic acid ester, see Tetrahedron Letters 2011, 52, 1506-1508) and 9 mg (0.01 mmol) of tetrakis(triphenylphosphine)palladium(0) were initially introduced in a mixture of degassed dioxane (2 mL) and degassed sodium carbonate solution (1M, 1 mL) under an argon atmosphere and stirred for 14 h at 96° C. The reaction mixture was then cooled to room temperature and concentrated under reduced pressure, and the residue was taken up in water and dichloromethane. The phases were separated, the aqueous phase was extracted three times with dichloromethane and the combined organic phases were dried over sodium sulphate and filtered. The solvent was distilled off under reduced pressure and the residue was purified by column chromatography using a water/acetonitrile gradient as mobile phase.

log P (neutral): 2.73; MH+: 514; $^1$H-NMR (400 MHz, D$_6$-DMSO) δ ppm: 1.23 (t, 3H), 3.82 (q, 2H), 3.97 (s, 3H), 7.31 (d, 1H), 7.62-7.65 (m, 1H), 8.33 (s, 1H), 8.39-8.41 (m, 1H), 8.58-8.65 (m, 3H), 8.81 (d, 1H), 9.26 (d, 1H), 9.33 (s, 1H).

Example I-2

2-(2,4-Dichlorophenyl)-4-[5-ethylsulfonyl-6-[3-methyl-6-(trifluoromethyl)imidazo[4,5-c]pyridin-2-yl]-2-pyridyl]-1,2,4-triazol-3-one

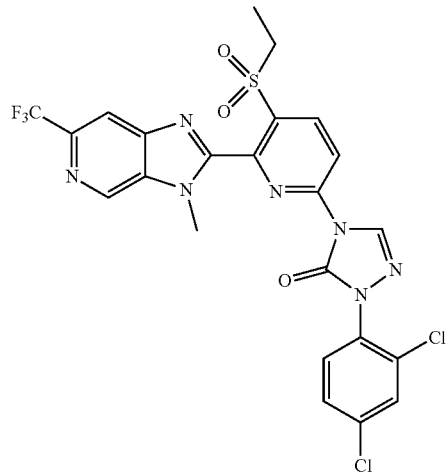 [SMILES: CCS(=O)(=O)c1ccc(-n2cnn(-c3ccc(Cl)cc3Cl)c2=O)nc1-c1nc2cc(C(F)(F)F)ncc2n1C]

50 mg (0.12 mmol) of 2-(6-chloro-3-ethylsulfonyl-2-pyridyl)-3-methyl-6-(trifluoromethyl)imidazo[4,5-c]pyridine were dissolved in 5 ml of acetonitrile; 85.25 mg (0.37 mmol) of 2-(2,4-dichlorophenyl)-4H-1,2,4-triazol-3-one, 20.49 mg (0.14 mmol) of potassium carbonate and 32.19 mg (0.09 mmol) of caesium carbonate were added and the mixture was stirred for 16 h at 65-70° C. The reaction mixture was then filtered off, the mother liquor was freed of the solvent under reduced pressure and the residue was purified by column chromatography via preparative HPLC using a water/acetonitrile gradient as mobile phase.

log P (neutral): 3.71; MH+: 598; $^1$H-NMR (400 MHz, D6-DMSO) δ ppm: 1.23 (t, 3H), 3.84 (q, 2H), 4.00 (s, 3H), 7.65-7.73 (m, 2H), 7.94 (d, 1H), 8.34 (s, 1H), 8.70, (d, 1H), 8.78 (d, 1H), 9.09 (s, 1H), 9.35 (s, 1H).

2-(6-Chloro-3-ethylsulphonyl-2-pyridyl)-3-methyl-6-(trifluoromethyl)imidazo[4,5-c]pyridine

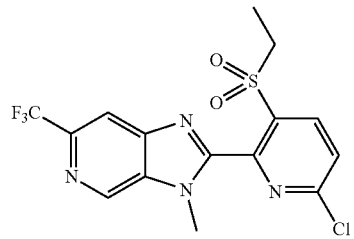 [SMILES: CCS(=O)(=O)c1ccc(Cl)nc1-c1nc2cc(C(F)(F)F)ncc2n1C]

900 mg (2.41 mmol) of 2-(6-chloro-3-ethylsulphanyl-2-pyridyl)-3-methyl-6-(trifluoromethyl)imidazo[4,5-c]pyridine were dissolved in 50 ml of dichloromethane, 555.6 mg (12.0 mmol) of formic acid and 1.64 mg (16.8 mmol) of 35% strength hydrogen peroxide were added at room temperature and the mixture was then stirred at room temperature for 5 h. The mixture was diluted with water and sodium bisulfite solution was added, the mixture was stirred for 1 h and saturated sodium hydrogencarbonate solution was then added. The organic phase was separated off, the aqueous phase was extracted twice with dichloromethane and the combined organic phases were then freed of the solvent under reduced pressure. The residue was purified by column chromatography purification by means of preparative HPLC using a water/acetonitrile gradient as mobile phase.

log P (neutral): 2.54; MH+: 405; 1H-NMR (400 MHz, D6-DMSO) δ ppm: 1.20 (t, 3H), 3.77 (q, 2H), 3.91 (s, 3H), 8.13 (d, 1H), 8.32 (s, 1H), 8.56 (d, 1H), 9.30 (s, 1H).

2-(6-Chloro-3-ethylsulphanyl-2-pyridyl)-3-methyl-6-(trifluoromethyl)imidazo[4,5-c]pyridine

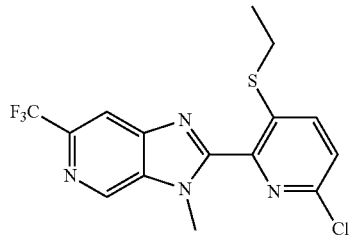 [SMILES: CCSc1ccc(Cl)nc1-c1nc2cc(C(F)(F)F)ncc2n1C]

4.00 g (10.7 mmol) of 2-(3,6-dichloro-2-pyridyl)-3-methyl-6-(trifluoromethyl)imidazo[4,5-c]pyridine were dissolved in 60 ml of tetrahydrofuran, 446 mg (11.1 mmol) of sodium hydride were added at −5° C. and the mixture was stirred at 0° C. for 30 minutes. Then, 733 mg (11.8 mmol) of ethanethiol were added dropwise over 30 minutes at −5° C., the cooling bath was removed and the mixture was after-stirred for 2 h at room temperature. The reaction mixture was hydrolyzed with water, the organic phase was separated off and the aqueous phase was extracted twice with ethyl acetate. The organic phases were combined, washed with sodium chloride solution and dried over sodium sulphate, and the solvent was then distilled off under reduced pressure. The residue was purified by trituration with methyl tert-butyl ketone/dichloromethane 25:1.

log P (neutral): 3.06; MH+: 373

2-(3,6-Dichloro-2-pyridyl)-3-methyl-6-(trifluoromethyl)imidazo[4,5-c]pyridine

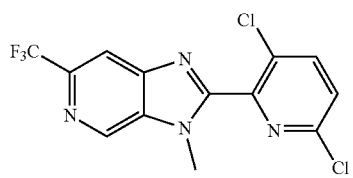 [SMILES: Cn1c(-c2nc(Cl)ccc2Cl)nc2cc(C(F)(F)F)ncc21]

20 g (104.6 mmol) of N3-methyl-6-(trifluoromethyl)pyridine-3,4-diamine, 25.11 g (130.8 mmol) of 3,6-dichloropyridine-2-carboxylic acid and 20.06 g (104.6 mmol) of 1-(3-dimethylaminopropyl)-3-ethylcarbodiimide hydrochloride (EDCI) were stirred in 200 ml of pyridine at 120° C. for 8 h. The reaction mixture was freed of solvent under reduced pressure, water was added and the mixture was extracted three times with ethyl acetate. The organic phases were combined and dried over sodium sulphate, and the solvent was then distilled off under reduced pressure. The residue was purified by column chromatography using a cyclohexane/ethyl acetate gradient as mobile phase.

log P (neutral): 2.81; MH+: 347; 1H-NMR (400 MHz, D6-DMSO) δ ppm: 3.99 (s, 3H), 7.89 (d, 1H), 8.32 (s, 1H), 8.35 (d, 1H), 9.28 (s, 1H).

Example I-33

4-(4-Chlorophenyl)-2-{5-(ethylsulfonyl)-6-[3-methyl-6-(trifluoromethyl)-3H-imidazo[4,5-b]pyridin-2-yl]pyridin-2-yl}-2,4-dihydro-3H-1,2,4-triazol-3-one

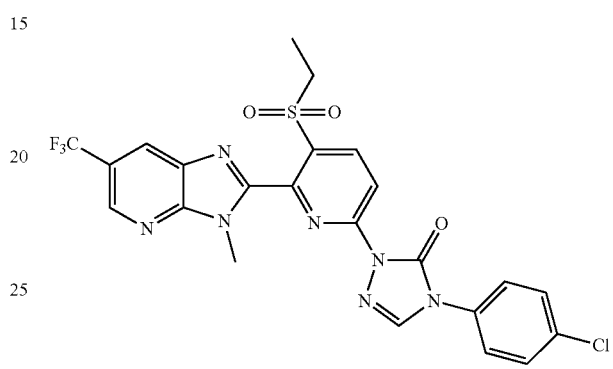

Under an argon atmosphere, 2-[3-(ethylsulfonyl)-6-fluoropyridin-2-yl]-3-methyl-6-(trifluoromethyl)-3H-imidazo[4,5-b]pyridine (50 mg, 0.12 mmol, 1 eq.) were dissolved in 8 ml of acetonitrile. Caesium carbonate (62 mg, 0.19 mmol, 1.5 eq.), potassium iodide (11 mg, 0.06 mmol, 0.5 eq.) and 4-(4-chlorophenyl)-2,4-dihydro-3H-1,2,4-triazol-3-one (50 mg, 0.25 mmol, 2 eq.) were added and the mixture was heated at 65-70° C. for 4 h. After cooling to room temperature, all solids were removed by filtration and silica gel was added to the reaction solution. The organic solvent was removed on a rotary evaporator and the residue was purified by chromatography (mobile phase: cyclohexane, ethyl acetate).

log P (neutral): 3.52; MH+: 564; 1H-NMR (400 MHz, D6-DMSO) δ ppm: 8.92 (s, 1H), 8.87 (s, 1H), 8.72-8.70 (m, 1H), 8.50-8.48 (m, 1H), 7.80-7.77 (m, 2H), 7.67-7.65 (m, 2H), 3.90-3.85 (m, 5H), 1.27-1.23 (m, 3H).

2-[3-(Ethylsulfonyl)-6-fluoropyridin-2-yl]-3-methyl-6-(trifluoromethyl)-3H-imidazo[4,5-b]pyridine

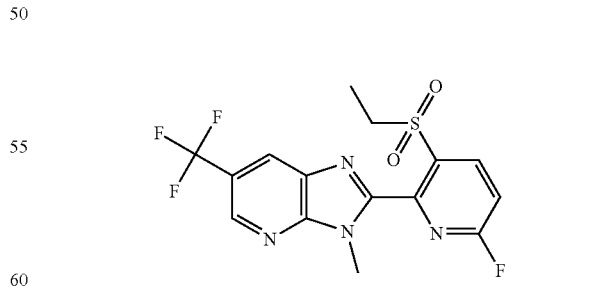

2-[3-(Ethylsulfanyl)-6-fluoropyridin-2-yl]-3-methyl-6-(trifluoromethyl)-3H-imidazo[4,5-b]pyridine (5.0 g, 14 mmol) was dissolved at room temperature in 144 ml of dichloromethane. Formic acid (3.2 g, 70 mmol) and aqueous hydrogen peroxide solution (35%, 9.5 g, 98 mmol) were added. After stirring for 12 h at room temperature, 20 ml of water and then slowly 20 ml of 40% sodium bisulfite solution were added in order to end the reaction. The mixture was stirred for 1 h, then the phases were separated. The aqueous phase was extracted three times with dichloromethane, then the combined organic extracts were washed with saturated NaHCO₃ solution. The organic phase was dried over MgSO₄, filtered and freed of the solvent under reduced pressure.

log P (neutral): 2.80; MH⁺: 389; ¹H-NMR (400 MHz, D₆-DMSO) δ ppm: 8.91 (m, 1H), 8.70 (m, 2H), 7.81 (dd, 1H), 3.82 (m, 5H), 1.22 (t, 3H)

2-[3-(Ethylsulfanyl)-6-fluoropyridin-2-yl]-3-methyl-6-(trifluoromethyl)-3H-imidazo[4,5-b]pyridine

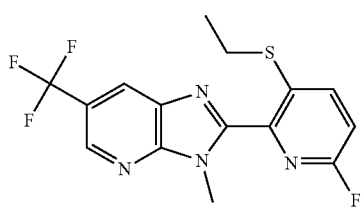 [SMILES: CCSc1ccc(F)nc1-c1nc2cc(C(F)(F)F)cnc2n1C]

2-(3,6-Difluoropyridin-2-yl)-3-methyl-6-(trifluoromethyl)-3H-imidazo[4,5-b]pyridine (2.5 g, 8.17 mmol) was dissolved in 19 ml of dry THF and cooled to −10° C. NaH (60%, 340 mg, 8.5 mmol) was added and the mixture was warmed to room temperature with stirring. Very slowly, ethyl mercaptan (559 mg, 9.0 mmol) dissolved in 10 ml of dry THF was added dropwise and the mixture was stirred for 3 h at room temperature. The reaction mixture was diluted with ethyl acetate and washed twice with saturated NaCl solution. After drying the organic phase, it was concentrated under reduced pressure and the residue was purified by column chromatography (mobile phase: gradient cyclohexane/ethyl acetate).

log P (neutral): 3.45; MH⁺: 357; ¹H-NMR (400 MHz, D₆-DMSO) δ ppm: 8.87 (s, 1H), 8.68 (m, 1H), 8.29 (m, 1H), 7.49 (dd, 1H), 3.94 (s, 3H), 3.01 (q, 2H), 1.19 (t, 3H).

2-(3,6-Difluoropyridin-2-yl)-3-methyl-6-(trifluoromethyl)-3H-imidazo[4,5-b]pyridine

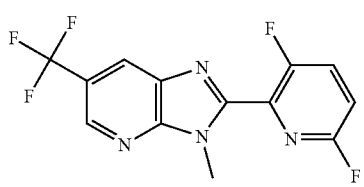 [SMILES: Cn1c(-c2nc(F)ccc2F)nc2cc(C(F)(F)F)cnc21]

Under argon, N2-methyl-5-(trifluoromethyl)pyridine-2,3-diamine (5.0 g, 18.3 mmol) was dissolved in 100 ml of dry pyridine and 3,6-difluoropyridine-2-carboxylic acid (2.9 g, 18.3 mmol) and N-(3-dimethylaminopropyl)-N'-ethylcarbodiimide hydrochloride (3.5 g, 18.3 mmol) were added. The mixture was stirred at 120° C. for 9 h. After cooling to room temperature, the mixture was concentrated under reduced pressure and then diluted with ethyl acetate. The organic phase was washed with water, dried over MgSO₄ and concentrated under reduced pressure. The product can be partially purified by recrystallization from methyl tert-butyl ether.

(log P (neutral): 2.72; MH⁺: 315; ¹H-NMR (400 MHz, D₆-DMSO) δ ppm: 8.88 (m, 1H), 8.70 (m, 1H), 8.29 (m, 1H), 7.60 (m, 1H), 4.07 (s, 3H).

Example I-35

4-{5-(Ethylsulfonyl)-6-[7-(trifluoromethyl)imidazo[1,2-c]pyrimidine-2-yl]pyridin-2-yl}-2-(2-fluorophenyl)-2,4-dihydro-3H-1,2,4-triazol-3-one

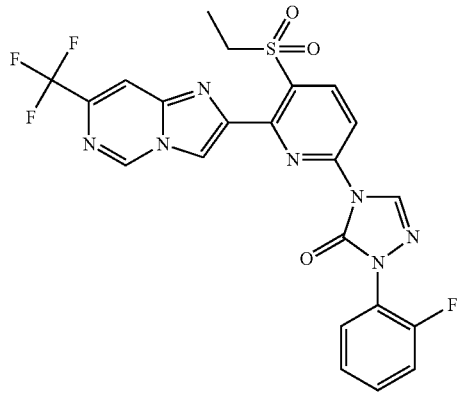 [SMILES: CCS(=O)(=O)c1ccc(-n2cnn(-c3ccccc3F)c2=O)nc1-c1cn2cnc(C(F)(F)F)cc2n1]

2-[3,6-Bis(ethylsulfonyl)pyridin-2-yl]-7-(trifluoromethyl)imidazo[1,2-c]pyrimidine (46 mg, 0.1 mmol, 1 eq.) was dissolved under an argon atmosphere in 3 ml of acetonitrile, and caesium carbonate (50 mg, 0.15 mmol, 1.5 eq.), potassium iodide (8 mg, 0.05 mmol, 0.5 eq.) and 2-(2-fluorophenyl)-2,4-dihydro-3H-1,2,4-triazol-3-one (37 mg, 0.2 mmol, 2 eq.) were added. The mixture was stirred for 12 h at room temperature and then heated at reflux for 1 h. After cooling to room temperature, all of the solid constituents were removed by filtration and the solution was concentrated on a rotary evaporator. The residue was purified by chromatography (mobile phase: cyclohexane, ethyl acetate).

log P (neutral): 3.16; MH⁺:534; ¹H-NMR (400 MHz, D6-DMSO) δ ppm: 9.65 (s, 1H), 9.17 (s, 1H), 9.02 (s, 1H), 8.72-8.67 (m, 1H), 8.48-8.46 (m, 1H), 8.41 (s, 1H), 7.70-7.65 (m, 1H), 7.60-7.54 (m, 1H), 7.52-7.45 (m, 1H), 7.42-7.39 (m, 1H), 4.22-4.17 (m, 2H), 1.30-1.27 (m, 3H).

2-[3,6-Bis(ethylsulfonyl)pyridin-2-yl]-7-(trifluoromethyl)imidazo[1,2-c]pyrimidine

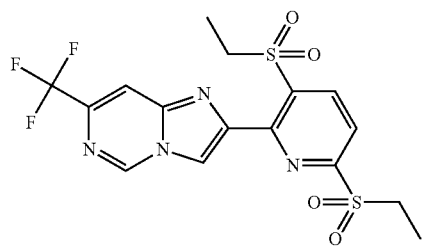 [SMILES: CCS(=O)(=O)c1ccc(S(=O)(=O)CC)c(-c2cn3cnc(C(F)(F)F)cc3n2)n1]

2-[3,6-Bis(ethylsulfanyl)pyridin-2-yl]-7-(trifluoromethyl)imidazo[1,2-c]pyrimidine (100 mg, 0.33 mmol, 1 eq.) was dissolved under an argon atmosphere in 2 ml of dry DMF. Sodium ethanethiolate (168 mg, 1.99 mmol, 6 eq.) was added and the mixture was stirred for 12 h at room temperature. The mixture was diluted with ethyl acetate and washed with saturated sodium chloride solution. The organic phase was dried over sodium sulphate and the solvent was removed on a rotary evaporator. The crude product was used in the subsequent reaction without further purification.

2-[3,6-Bis(ethylsulphanyl)pyridin-2-yl]-7-(trifluoromethyl)imidazo[1,2-c]pyrimidine (75 mg, 0.19 mmol, 1 eq.) was dissolved in 9 ml of dichloromethane. At room temperature, formic acid (90 mg, 1.95 mmol, 10 eq.) and hydrogen peroxide solution (35%, 265 mg, 12.7 mmol, 14 eq.) were added and the mixture was stirred for 12 h. After adding 1 ml of wasser, 3 ml of 40% sodium bisulphite solution were slowly added dropwise and the mixture was stirred for 1 h. Then, the organic phase was separated off, washed with saturated sodium hydrogencarbonate solution, dried over sodium sulphate and concentrated. The residue was purified by chromatography (mobile phase: cyclohexane, ethyl acetate).

log P (neutral): 2.28; MH$^+$:449; $^1$H-NMR (400 MHz, D$_6$-DMSO) δ ppm: 9.67 (s, 1H), 8.86 (s, 1H), 8.82-8.80 (m, 1H), 8.41 (s, 1H), 8.36-8.34 (m, 1H), 4.23-4.18 (m, 2H), 3.64-3.59 (m, 2H), 1.30-1.23 (m, 6H).

2-(3,6-Difluoropyridin-2-yl)-7-(trifluoromethyl)imidazo[1,2-c]pyrimidine

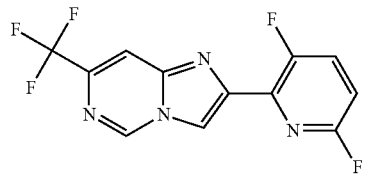 [SMILES: Fc1ccc(F)c(-c2cn3cnc(C(F)(F)F)cc3n2)n1]

In a second reaction vessel, 6-(trifluoromethyl)pyrimidin-4-amine (201 mg, 1.23 mmol, 1 eq.) and sodium hydrogencarbonate (155 mg, 1.85 mmol, 1.5 eq.) were dissolved or suspended in 3 ml of chloroform. 2-Bromo-1-(3,6-difluoropyridin-2-yl)ethanone (502 mg, 1.23 mmol, 1 eq.) was added dropwise dissolved in 1 ml of chloroform, then the reaction mixture was heated at 60° C. for 4 h. Sodium hydrogencarbonate was filtered off and the organic phase was concentrated. The residue was purified by chromatography (silica gel, mobile phase: cyclohexane/ethyl acetate).

log P (neutral): 2.02; MH$^+$: 301; $^1$H-NMR (400 MHz, D$_6$-DMSO) δ ppm: 9.64 (s, 1H), 8.77 (d, 1H), 8.35 (s, 1H), 8.17-8.10 (m, 1H), 7.36-7.32 (m, 1H).

2-Bromo-1-(3,6-difluoropyridin-2-yl)ethanone

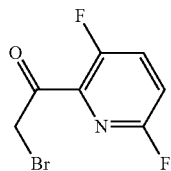 [SMILES: O=C(CBr)c1nc(F)ccc1F]

1-(3,6-Difluoropyridin-2-yl)ethanone (6.4 g, 40.7 mmol) was dissolved in 96 ml of ethanol and copper(II) bromide (13.7 g, 61.1 mmol) was added. The reaction mixture was heated at 60° C. for 4 h. After cooling to room temperature, the solvent was removed on the rotary evaporator and the residue was taken up with saturated ammonium chloride solution and with ethyl acetate. The aqueous phase was extracted twice with ethyl acetate. The combined organic extracts were washed with saturated sodium chloride solution, dried over sodium sulphate and concentrated. The product was isolated as a mixture and used in the subsequent reaction without further purification.

log P (neutral): 1.95; MH$^+$:2.38; $^1$H-NMR (400 MHz, CDCl3) δ ppm: 8.17-8.10 (m, 1H), 7.62-7.57 (m, 1H), 2.56 (s, 2H)

1-(3,6-Difluoropyridin-2-yl)ethanone

Under an argon atmosphere, 3,6-difluoro-N-methoxy-N-methylpyridine-2-carboxamide (10.1 g, 50.2 mmol) was dissolved in 270 ml of dry THF and cooled to 0° C. Methylmagnesium bromide (3M in diethyl ether, 50 ml, 150 mmol) was slowly added dropwise, then the mixture was stirred for 2 h at 0° C. In order to end the reaction, 50 ml of ammonium chloride solution were slowly added with cooling. The organic phase was separated off, washed with saturated sodium chloride solution and concentrated. The product was used in the subsequent reaction without further purification.

log P (neutral): 1.24; MH$^+$: 158; $^1$H-NMR (400 MHz, CDCl3) δ ppm: 8.16-8.10 (m, 1H), 7.61-7.57 (m, 1H), 2.56-2.55 (m, 3H).

3,6-Difluoro-N-methoxy-N-methylpyridine-2-carboxamide

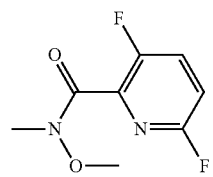

3,6-Difluoropyridine-2-carboxylic acid (15 g, 94 mmol) and N,O-dimethylhydroxylamine hydrochloride (9.1 g, 94.2 mmol) were dissolved in 600 ml of dichloromethane and cooled to 0° C. 4-Dimethylaminopyridine (DMAP, 13.8 g, 113 mmol) and N-(dimethylaminopropyl)-N'-ethylcarbodiimide hydrochloride (EDCI, 19.9 g, 103 mmol) were added and the reaction mixture was stirred for 2 h at 0° C., then for 12 h at room temperature. The solution was washed once with saturated sodium hydrogencarbonate solution and once with sodium chloride solution, dried over sodium sulphate and concentrated. The crude product was used in the subsequent reaction without further purification.

log P (neutral): 1.05; MH$^+$: 203; $^1$H-NMR (400 MHz, CDCl3) δ ppm: 8.15-8.09 (m, 1H), 7.44-7.42 (m, 1H), 3.57 (s, 3H), 3.31 (s, 3H).

In analogy to the examples and according to the above-described preparation processes,
the following compounds of the formula (I) can be obtained:

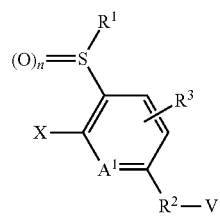

where the substituents $R^1$, $R^2$, $R^3$, $A^1$, X, V and n have the meanings given in the table below and where the bond from $R^2$—V to the remainder of the molecule is characterized by a wavy line and the bond from X to the remainder of the molecule is characterized by a dotted line:

| Ex. | $R^1$ | n | $A^1$ | $R^3$ | X | $R^2$—V |
|---|---|---|---|---|---|---|
| I-1 | —CH$_2$CH$_3$ | 2 | N | —H | [6-(trifluoromethyl)-1-methyl-imidazo[4,5-b]pyridin-2-yl] | [4-(2-fluorophenyl)-5-oxo-4,5-dihydro-1,2,4-triazol-1-yl] |
| I-2 | —CH$_2$CH$_3$ | 2 | N | H | [6-(trifluoromethyl)-1-methyl-imidazo[4,5-b]pyridin-2-yl] | [4-(2,4-dichlorophenyl)-5-oxo-4,5-dihydro-1,2,4-triazol-1-yl] |
| I-3 | —CH$_2$CH$_3$ | 2 | N | —H | [6-(trifluoromethyl)-1-methyl-imidazo[4,5-b]pyridin-2-yl] | [3-(4-bromophenyl)-2-oxo-2,3-dihydro-1H-imidazol-1-yl] |

-continued

| Ex. | R¹ | n | A¹ | R³ | X | R²—V |
|---|---|---|---|---|---|---|
| I-4 | —CH$_2$CH$_3$ | 2 | N | —H | 6-(trifluoromethyl)-1-methyl-imidazo[4,5-c]pyridin-2-yl | 1-(2-chlorophenyl)-5-oxo-tetrazol-4-yl |
| I-5 | —CH$_2$CH$_3$ | 2 | N | —H | 6-(trifluoromethyl)-1-methyl-imidazo[4,5-c]pyridin-2-yl | 3-(4-chlorophenyl)-2-oxo-imidazolidin-1-yl |
| I-6 | —CH$_2$CH$_3$ | 2 | N | —H | 6-(trifluoromethyl)-1-methyl-imidazo[4,5-c]pyridin-2-yl | 3-(4-chlorophenyl)-pyrazol-1-yl |
| I-7 | —CH$_2$CH$_3$ | 2 | N | —H | 6-(trifluoromethyl)-1-methyl-imidazo[4,5-c]pyridin-2-yl | 4-(3-chloropyridin-2-yl)-pyrazol-1-yl |
| I-8 | —CH$_2$CH$_3$ | 2 | N | —H | 6-(trifluoromethyl)-1-methyl-imidazo[4,5-c]pyridin-2-yl | 4-(4-fluorophenyl)-5-oxo-1,2,4-triazol-1-yl |

-continued
| Ex. | R¹ | n | A¹ | R³ | X | R²—V |
|---|---|---|---|---|---|---|
| I-9 | —CH₂CH₃ | 2 | N | —H | 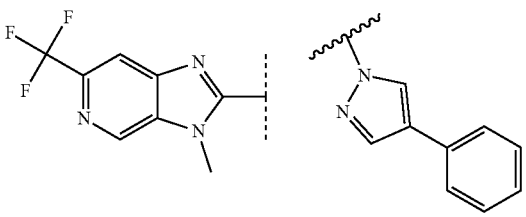 | 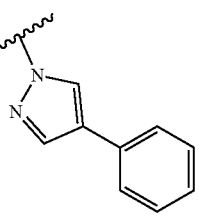 |
| I-10 | —CH₂CH₃ | 2 | N | —H | 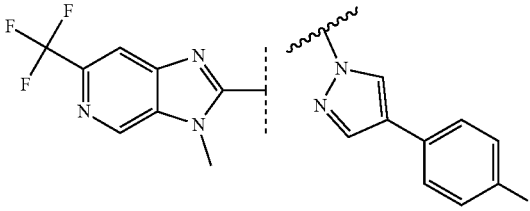 | 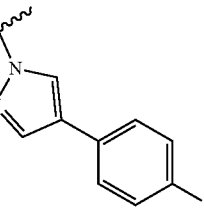 |
| I-11 | —CH₂CH₃ | 2 | N | —H | 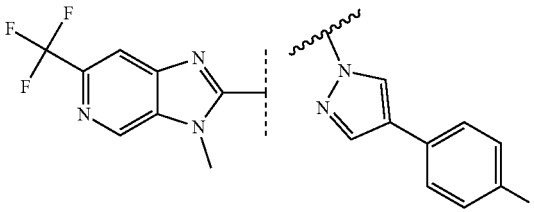 | 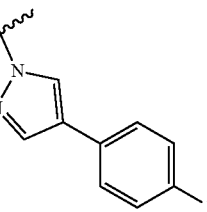 |
| I-12 | —CH₂CH₃ | 2 | N | —H | 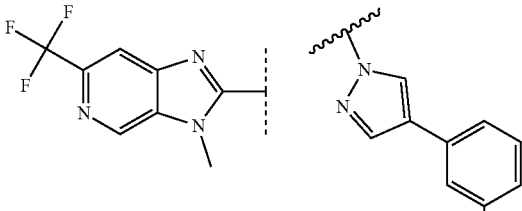 | 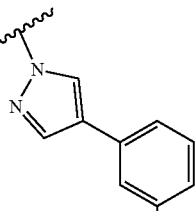 |
| I-13 | —CH₂CH₃ | 2 | N | —H | 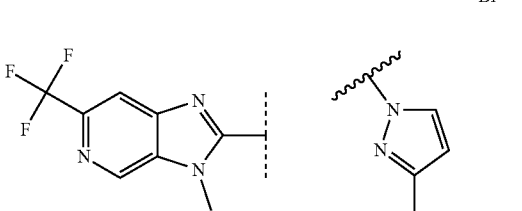 | 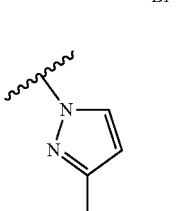 |
| I-14 | —CH2CH3 | 2 | N | H | 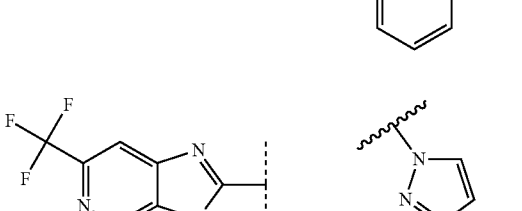 | 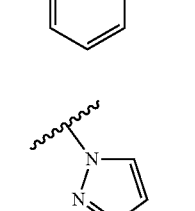 |

-continued

| Ex. | R¹ | n | A¹ | R³ | X | R²—V |
|---|---|---|---|---|---|---|
| I-15 | —CH2CH3 | 2 | N | H | 6-(trifluoromethyl)-1-methyl-imidazo[4,5-c]pyridin-2-yl | 2-phenyl-1,2,4-triazol-3(4H)-one, N1-linked, N4-phenyl |
| I-16 | —CH2CH3 | 2 | N | H | 6-(trifluoromethyl)-1-methyl-imidazo[4,5-c]pyridin-2-yl | 2,4-disubstituted-1,2,4-triazol-3(4H)-one, N4-(4-bromophenyl) |
| I-17 | —CH₂CH₃ | 2 | N | H | 6-(trifluoromethyl)-1-methyl-imidazo[4,5-c]pyridin-2-yl | 2,4-disubstituted-1,2,4-triazol-3(4H)-one, N4-(pyridin-3-yl) |
| I-18 | —CH₂CH₃ | 2 | N | H | 6-(trifluoromethyl)-1-methyl-imidazo[4,5-c]pyridin-2-yl | 2,4-disubstituted-1,2,4-triazol-3(4H)-one, N4-(2-fluorophenyl) |
| I-19 | —CH₂CH₃ | 2 | N | H | 6-(trifluoromethyl)-1-methyl-imidazo[4,5-c]pyridin-2-yl | 2,4-disubstituted-1,2,4-triazol-3(4H)-one, N4-(4-chlorophenyl) |

-continued
| Ex. | R¹ | n | A¹ | R³ | X | R²—V |
|---|---|---|---|---|---|---|
| I-20 | —CH₂CH₃ | 2 | N | H | 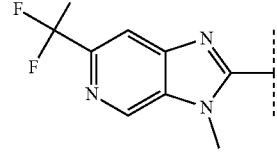 | 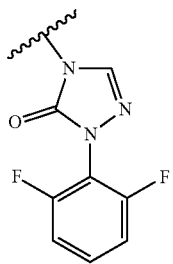 [SMILES: *n1cnn(-c2c(F)cccc2F)c1=O] |
| I-21 | —CH₂CH₃ | 2 | N | H | 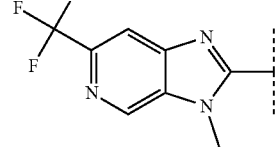 | 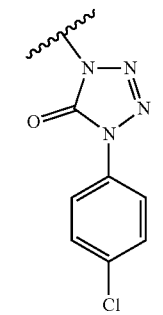 [SMILES: *n1nnn(-c2ccc(Cl)cc2)c1=O] |
| I-22 | —CH₂CH₃ | 2 | N | H | 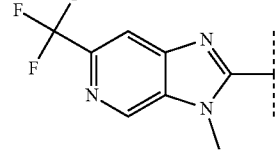 | 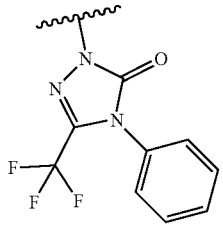 [SMILES: *n1nc(C(F)(F)F)n(-c2ccccc2)c1=O] |
| I-23 | —CH₂CH₃ | 2 | N | H | 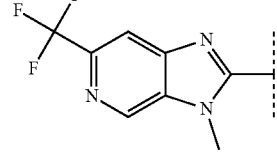 | 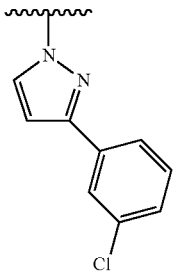 [SMILES: *n1ccc(-c2cccc(Cl)c2)n1] |
| I-24 | —CH₂CH₃ | 2 | N | H | 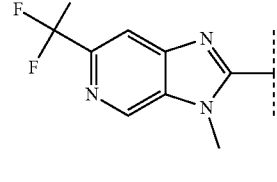 | 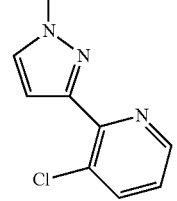 |
| I-25 | —CH₂CH₃ | 2 | N | H | 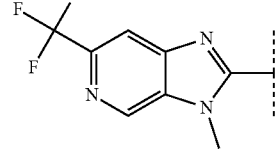 | 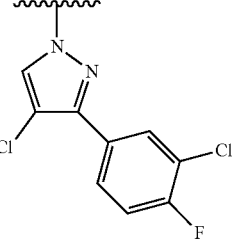 |

-continued
| Ex. | R¹ | n | A¹ | R³ | X | R²—V |
|---|---|---|---|---|---|---|
| I-26 | —CH₂CH₃ | 2 | N | H |  | 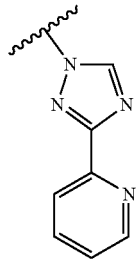 [SMILES: *n1cnc(-c2ccccn2)n1] |
| I-27 | —CH₂CH₃ | 2 | N | H | 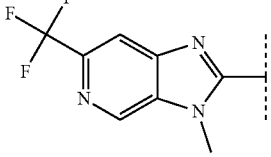 | 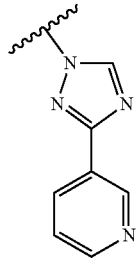 [SMILES: *n1cnc(-c2cccnc2)n1] |
| I-28 | —CH₂CH₃ | 2 | N | H | 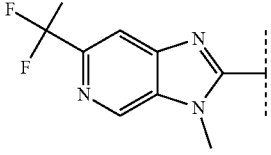 | 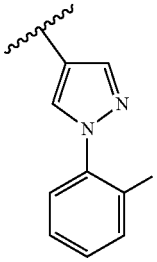 |
| I-29 | —CH₂CH₃ | 2 | N | H | 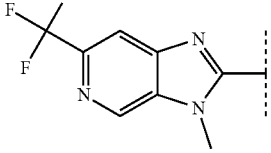 | 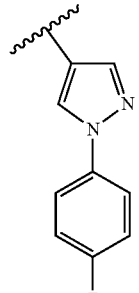 |
| I-30 | —CH₂CH₃ | 2 | N | H | 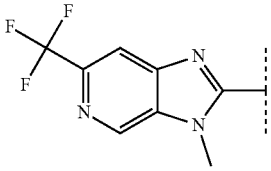 | 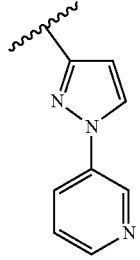 [SMILES: *c1ccn(-c2cccnc2)n1] |

-continued

| Ex. | R¹ | n | A¹ | R³ | X | R²—V |
|---|---|---|---|---|---|---|
| I-31 | —CH₂CH₃ | 2 | N | H | 6-trifluoromethyl-imidazo[4,5-c]pyridin-2-yl (N-methyl) | 3-phenyl-isoxazol-5-yl |
| I-32 | —CH₂CH₃ | 2 | N | H | 6-trifluoromethyl-imidazo[4,5-b]pyridin-2-yl (N-methyl) | 1-(2-fluorophenyl)-5-oxo-1,2,4-triazol-4-yl |
| I-33 | —CH₂CH₃ | 2 | N | H | 6-trifluoromethyl-imidazo[4,5-b]pyridin-2-yl (N-methyl) | 4-(4-chlorophenyl)-5-oxo-1,2,4-triazol-1-yl |
| I-34 | —CH₂CH₃ | 2 | N | H | 5-trifluoromethyl-benzimidazol-2-yl (N-methyl) | 1-(2-fluorophenyl)-5-oxo-1,2,4-triazol-4-yl |
| I-35 | —CH₂CH₃ | 2 | N | H | 7-trifluoromethyl-imidazo[1,2-c]pyrimidin-2-yl | 1-(2-fluorophenyl)-5-oxo-1,2,4-triazol-4-yl |

Example I-1: logP (neutral): 3.03 ¹H-NMR(400.0 MHz, d₆-DMSO): δ =
9.352(4.6); 9.070(6.9); 8.791(2.3); 8.768(4.5); 8.724(4.5); 8.702(2.4); 8.339(4.9); 7.677(0.9); 7.662(1.6); 7.658(1.8); 7.642(0.9); 7.638(1.0); 7.598(0.3); 7.581(0.9); 7.564(1.1); 7.550(0.7); 7.546(0.6); 7.519(1.3); 7.496(1.5); 7.474(0.7); 7.426(1.2); 7.405(1.9); 7.388(0.8); 4.005(16.0); 3.873(1.0); 3.855(3.5); 3.836(3.5); 3.818(1.1); 3.315(67.6); 2.670(1.0); 2.505(123.3); 2.501(159.0); 2.497(120.2); 2.328(1.0); 2.324(0.7); 2.073(0.6); 1.253(3.8); 1.235(8.4); 1.216(3.7); 0.000(11.1)

Example I-3: logP (neutral): 3.87 ¹H-NMR(400.0 MHz, d₆-DMSO): δ =
9.326(4.7); 9.288(0.5); 8.854(3.0); 8.832(4.1); 8.686(3.8); 8.663(3.0); 8.324(5.0); 8.314(1.1); 8.304(0.4); 8.291(0.6); 8.243(0.4); 7.767(2.1); 7.744(7.6); 7.727(7.5); 7.705(2.2); 7.664(0.4); 7.639(3.7); 7.630(4.0); 7.616(0.4); 7.587(0.4); 7.565(0.5); 7.548(0.5); 7.510(0.6); 7.491(0.4);

7.446(3.7); 7.437(3.6); 7.417(0.5); 7.368(0.4); 7.361(0.3); 7.126(0.3); 3.980(0.8); 3.968(16.0); 3.954(0.8); 3.902(1.3); 3.875(0.5); 3.868(0.5); 3.823(1.6); 3.802(3.6); 3.784(3.8); 3.766(1.4); 3.702(0.3); 3.685(0.4); 3.385(0.4); 3.361(0.7); 3.319(476.1); 2.671(2.9); 2.666(2.1); 2.506(375.7); 2.501(483.5); 2.497(351.0); 2.332(2.2); 2.328(2.9); 1.268(0.4); 1.242(4.1); 1.223(8.7); 1.205(4.3); 1.184(1.5); 1.166(1.0); 1.150(0.6); 1.132(0.6); 1.115(0.4); 1.105(0.4); 0.000(25.3); −0.008(1.0)

Example I-4: logP (neutral): 3.34 $^1$H-NMR(400.0 MHz, d$_6$-DMSO): δ =
9.323(4.0); 8.866(3.3); 8.844(3.9); 8.580(3.9); 8.558(3.6); 8.348(4.3); 7.843(3.0); 7.839(1.8); 7.824(3.9); 7.820(2.4); 7.737(0.8); 7.732(0.9); 7.718(1.7); 7.713(1.6); 7.698(1.2); 7.693(1.1); 7.678(1.4); 7.674(1.4); 7.659(1.7); 7.655(1.6); 7.639(0.6); 7.636(0.6); 3.998(16.0); 3.888(0.9); 3.870(3.3); 3.851(3.3); 3.833(1.0); 3.319(75.1); 2.676(0.4); 2.671(0.6); 2.667(0.4); 2.524(1.3); 2.511(33.7); 2.507(71.0); 2.502(95.3); 2.498(69.4); 2.493(34.6); 2.333(0.4); 2.329(0.6); 2.324(0.4); 1.263(3.6); 1.244(8.1); 1.226(3.5); 0.008(0.5); 0.000(15.8); −0.008(0.7)

Example I-5: logP (neutral): 3.86 $^1$H-NMR(400.0 MHz, d$_6$-DMSO): δ =
9.305(4.0); 8.681(3.3); 8.658(4.4); 8.470(3.9); 8.447(3.4); 8.313(0.5); 8.299(4.2); 7.735(0.4); 7.727(4.0); 7.722(1.4); 7.710(1.4); 7.705(5.0); 7.697(0.5); 7.502(0.5); 7.494(5.2); 7.489(1.5); 7.477(1.3); 7.471(4.4); 7.463(0.4); 4.162(0.9); 4.144(1.9); 4.137(1.3); 4.122(1.8); 4.026(1.7); 4.005(1.8); 3.985(0.9); 3.942(16.0); 3.764(1.0); 3.745(3.2); 3.727(3.3); 3.708(0.9); 3.317(129.2); 2.675(0.7); 2.670(1.0); 2.666(0.8); 2.661(0.4); 2.524(2.4); 2.519(3.7); 2.510(60.0); 2.506(128.2); 2.501(174.0); 2.497(125.1); 2.492(59.4); 2.337(0.3); 2.333(0.7); 2.328(1.0); 2.323(0.7); 2.319(0.3); 2.073(3.5); 1.234(0.8); 1.223(3.6); 1.205(8.1); 1.186(3.5); 0.146(0.4); 0.008(2.7); 0.000(88.7); −0.008(3.0); −0.150(0.4)

Example I-6: logP (neutral): 4.62 $^1$H-NMR(400.0 MHz, d$_6$-DMSO): δ =
9.344(4.0); 8.809(3.9); 8.802(4.0); 8.705(3.2); 8.683(4.0); 8.470(3.9); 8.448(3.4); 8.336(4.2); 8.334(4.3); 8.313(0.4); 8.074(0.6); 8.068(4.4); 8.063(1.6); 8.051(1.6); 8.046(5.1); 8.040(0.7); 7.604(0.7); 7.598(5.0); 7.593(1.7); 7.581(1.5); 7.576(4.8); 7.259(3.7); 7.252(3.7); 4.092(0.4); 4.003(16.0); 3.852(0.9); 3.833(3.3); 3.815(3.3); 3.796(1.0); 3.320(150.6); 2.675(0.6); 2.671(0.9); 2.666(0.7); 2.524(2.4); 2.511(55.3); 2.506(116.2); 2.502(156.5); 2.497(113.1); 2.493(54.5); 2.333(0.7); 2.329(0.9); 2.324(0.7); 2.074(0.9); 1.258(3.5); 1.240(8.1); 1.221(3.4); 0.008(0.9); 0.000(25.1); −0.008(1.0)

Example I-7: logP (neutral): 3.66 $^1$H-NMR(400.0 MHz, d$_6$-DMSO): δ =
9.389(0.4); 9.326(3.9); 9.247(5.1); 9.246(5.4); 9.205(0.4); 8.727(3.4); 8.705(4.1); 8.640(5.3); 8.638(5.5); 8.611(2.1); 8.607(2.3); 8.599(2.3); 8.596(2.3); 8.565(0.4); 8.465(3.9); 8.457(0.4); 8.453(0.4); 8.443(3.6); 8.346(0.4); 8.338(4.1); 8.337(4.2); 8.048(2.1); 8.045(2.2); 8.028(2.3); 8.024(2.2); 7.404(2.2); 7.393(2.1); 7.384(1.9); 7.373(2.0); 4.450(1.2); 4.093(1.2); 4.005(16.0); 3.854(0.9); 3.835(3.1); 3.817(3.2); 3.798(0.9); 3.321(74.6); 2.676(0.5); 2.672(0.6); 2.667(0.5); 2.525(1.5); 2.512(38.4); 2.507(80.9); 2.503(108.5); 2.498(78.1); 2.494(37.4); 2.334(0.4); 2.329(0.6); 2.325(0.5); 1.323(0.6); 1.260(3.5); 1.242(8.1); 1.223(3.5); 0.008(0.5); 0.000(16.4); −0.009(0.6)

Example I-8: logP (neutral): 2.75 $^1$H-NMR(400.0 MHz, d$_6$-DMSO): δ =
9.311(4.0); 8.815(9.1); 8.710(3.2); 8.688(4.2); 8.522(4.2); 8.500(3.6); 8.327(4.2); 8.326(4.2); 8.313(0.6); 8.147(1.2); 7.789(2.2); 7.783(0.9); 7.776(2.4); 7.771(1.4); 7.766(2.7); 7.759(0.9); 7.754(2.6); 7.462(2.7); 7.456(0.8); 7.440(4.3); 7.423(0.7); 7.418(2.4); 4.316(0.4); 3.977(16.0); 3.849(0.9); 3.831(3.3); 3.812(3.3); 3.794(1.0); 3.780(0.5); 3.317(81.6); 2.679(0.5); 2.675(1.0); 2.670(1.5); 2.666(1.1); 2.524(3.3); 2.519(5.1); 2.510(85.2); 2.506(183.7); 2.501(249.8); 2.497(180.2); 2.492(85.3); 2.332(1.0); 2.328(1.5); 2.323(1.1); 2.073(0.8); 1.988(0.4); 1.447(0.4); 1.430(0.4); 1.250(3.6); 1.231(8.1); 1.213(3.5); 1.175(0.4); 0.146(1.4); 0.008(10.3); 0.000(329.0); −0.009(11.3); −0.150(1.4)

Example I-9: logP (neutral): 3.92 $^1$H-NMR(400.0 MHz, d$_6$-DMSO): δ =
9.364(4.1); 9.170(5.0); 8.683(3.4); 8.661(4.1); 8.535(5.1); 8.409(3.9); 8.387(3.6); 8.344(4.3); 8.312(0.7); 7.823(3.2); 7.805(3.4); 7.420(1.9); 7.401(3.8); 7.382(2.4); 7.302(1.3); 7.284(1.9); 7.266(0.8); 4.454(0.4); 4.029(16.0); 3.853(0.9); 3.834(3.2); 3.815(3.3); 3.797(1.0); 3.324(225.0); 2.675(1.2); 2.671(1.7); 2.666(1.3); 2.524(4.2); 2.511(103.9); 2.506(219.7); 2.502(297.2); 2.497(215.9); 2.493(105.4); 2.333(1.2); 2.329(1.7); 2.324(1.1); 1.261(3.6); 1.242(8.4); 1.223(3.6); 0.146(1.3); 0.008(10.2); 0.000(295.2); −0.008(11.8); −0.150(1.3)

Example I-10: logP (neutral): 4.33 $^1$H-NMR(400.0 MHz, d$_6$-DMSO): δ =
9.407(0.7); 9.368(4.3); 9.341(0.4); 9.228(5.1); 9.218(1.0); 9.140(0.5); 8.697(0.6); 8.686(3.2); 8.675(0.8); 8.664(3.9); 8.554(5.2); 8.508(0.9); 8.458(0.5); 8.419(0.9); 8.407(3.8); 8.397(0.6); 8.385(3.4); 8.365(0.8); 8.344(4.6); 8.314(3.6); 8.218(0.3); 7.911(0.7); 7.889(0.8); 7.874(4.4); 7.857(1.9); 7.853(5.0); 7.837(0.6); 7.642(0.4); 7.621(0.4); 7.513(0.8); 7.492(0.7); 7.469(5.1); 7.464(2.0); 7.448(4.7); 7.441(1.0); 7.403(0.4); 7.383(0.3); 4.447(2.6); 4.113(1.6); 4.056(0.4); 4.038(1.4); 4.027(16.0); 3.854(1.0); 3.835(3.2); 3.817(3.3); 3.798(1.0); 3.317(190.9); 3.293(1.8); 2.675(1.6); 2.670(2.2); 2.666(1.6); 2.524(5.5); 2.510(134.9); 2.506(276.1); 2.501(366.7); 2.497(267.2); 2.333(1.5); 2.328(2.1); 2.324(1.6); 2.073(1.5); 1.988(4.5); 1.337(0.7); 1.319(1.3); 1.301(0.6); 1.259(3.7); 1.241(8.3); 1.222(3.6); 1.193(1.2); 1.175(2.4); 1.157(1.2); 0.146(1.9); 0.008(16.5); 0.000(418.8); −0.009(19.1); −0.150(1.9)

Example I-11: logP (neutral): 4.17 $^1$H-NMR(400.0 MHz, d$_6$-DMSO): δ =
9.394(0.4); 9.343(3.8); 8.872(0.3); 8.865(0.4); 8.795(3.9); 8.788(4.1); 8.713(0.4); 8.700(3.3); 8.691(0.5); 8.678(4.1); 8.472(0.4); 8.463(4.0); 8.450(0.4); 8.441(3.5); 8.359(0.4); 8.336(3.9); 8.334(4.1); 8.313(0.7); 8.097(2.1); 8.092(0.9); 8.083(2.4); 8.075(2.4); 8.067(1.1); 8.061(2.0); 7.379(2.2); 7.357(4.4); 7.340(0.7); 7.335(2.3); 7.238(0.4); 7.228(3.6); 7.221(3.7); 4.430(1.4); 4.092(0.6); 4.003(16.0); 3.848(0.9); 3.829(3.2); 3.811(3.2); 3.792(0.9); 3.319(149.9); 2.680(0.6); 2.675(1.2); 2.671(1.7); 2.666(1.2); 2.662(0.6); 2.524(4.3); 2.519(6.6); 2.511(95.8); 2.506(205.5); 2.501(279.9); 2.497(200.6); 2.492(94.3); 2.333(1.1); 2.328(1.6); 2.324(1.1); 2.319(0.5); 2.073(1.0); 1.340(0.4); 1.321(0.8); 1.303(0.4); 1.257(3.5); 1.239(8.0); 1.220(3.4); 0.146(0.7); 0.008(6.0); 0.000(183.7); −0.009(6.3); −0.150(0.7)

Example I-12: logP (neutral): 4.48 $^1$H-NMR(400.0 MHz, d$_6$-DMSO): δ =
9.372(3.8); 9.294(4.6); 8.690(3.6); 8.668(4.3); 8.599(4.7); 8.412(4.1); 8.390(3.8); 8.346(4.0); 8.314(0.5); 8.103(1.7); 8.098(3.0); 8.094(1.8); 7.855(1.4); 7.835(1.5); 7.480(0.9); 7.478(1.1); 7.476(1.0); 7.473(1.0); 7.458(1.5); 7.455(1.6); 7.453(1.4); 7.376(1.9); 7.356(2.9); 7.336(1.3); 4.451(0.3); 4.031(16.0); 3.857(0.9); 3.839(3.0); 3.820(3.1); 3.802(0.9); 3.316(100.2); 2.675(1.0); 2.670(1.4); 2.666(1.0); 2.661(0.5); 2.524(3.8); 2.519(6.0); 2.510(86.0); 2.506(182.3); 2.501(245.4); 2.497(174.9); 2.492(82.5); 2.337(0.5); 2.333(1.1); 2.328(1.4); 2.323(1.1); 2.073(0.4); 1.260(3.5); 1.242(8.0); 1.223(3.5); 0.146(1.2); 0.008(10.9); 0.000(304.0); −0.009(10.9); −0.150(1.2)

Example I-13: logP (neutral): 4.58 $^1$H-NMR(400.0 MHz, d$_6$-DMSO): δ =
9.345(4.2); 9.323(0.3); 8.831(3.8); 8.824(4.0); 8.708(3.2); 8.686(3.9); 8.454(4.0); 8.432(3.6); 8.364(0.3); 8.338(4.4); 8.312(1.4); 7.929(1.5); 7.918(1.7); 7.911(1.1); 7.905(1.7); 7.643(1.4); 7.637(1.0); 7.631(1.6); 7.627(1.2); 7.620(1.9); 7.611(0.5); 7.529(0.6); 7.514(2.9); 7.503(3.1); 7.497(1.9); 7.491(2.3); 7.479(0.6); 7.125(3.8); 7.118(4.0); 4.438(0.6); 4.099(1.0); 4.009(16.0); 3.853(1.0); 3.834(3.4); 3.816(3.5); 3.797(1.2); 3.473(0.2); 3.436(0.7); 3.410(1.1); 3.369(4.2); 3.330(517.0); 3.239(0.6); 3.204(0.4); 3.167(0.4); 3.146(0.3); 2.675(0.2); 2.671(3.0); 2.666(2.2); 2.579(0.5); 2.555(0.8); 2.524(8.3); 2.510(185.4); 2.506(374.0); 2.501(494.0); 2.497(366.3); 2.493(184.0); 2.438(2.4); 2.432(0.4); 2.333(2.2); 2.328(3.2); 2.324(2.3); 1.320(0.4); 1.258(3.6); 1.239(8.3); 1.220(3.6); 0.146(0.4); 0.008(3.6); 0.000(109.6); −0.008(4.4); −0.150(0.4)

Example I-14: logP (neutral): 3.47 1H-NMR(601.6 MHz, d6-DMSO): □ =
9.340(4.7); 8.781(3.5); 8.776(3.5); 8.686(3.0); 8.672(3.3); 8.387(3.4); 8.372(3.1); 8.329(4.9); 8.311(0.4); 7.854(3.7); 7.067(2.9); 7.062(3.0); 7.007(3.4); 7.003(3.4); 6.684(2.2); 6.681(2.7); 6.678(2.6); 6.676(2.7); 3.999(16.0); 3.835(1.3); 3.823(3.6); 3.810(3.8); 3.798(1.3); 3.310(91.2); 2.613(1.3); 2.501(218.0); 2.498(182.8); 2.385(1.4); 2.072(2.2); 1.248(3.8); 1.236(8.3); 1.224(4.3); 0.000(4.6)

Example I-15: logP (neutral): 2.70 1H-NMR(400.0 MHz, d6-DMSO): □ =
9.313(4.0); 8.851(7.9); 8.710(3.2); 8.688(4.1); 8.534(4.0); 8.512(3.4); 8.330(4.2); 7.746(2.2); 7.743(3.0); 7.724(3.5); 7.601(2.0); 7.582(3.5); 7.562(2.3); 7.478(1.4); 7.459(2.0); 7.441(0.7); 3.979(16.0); 3.849(0.9); 3.830(3.3); 3.812(3.3); 3.793(1.0); 3.385(0.5); 3.370(0.7); 3.320(1057.6); 2.675(2.2); 2.670(3.0); 2.665(2.3); 2.523(7.4); 2.510(181.1); 2.505(376.4); 2.501(504.7); 2.496(370.6); 2.492(182.8); 2.332(2.2); 2.328(3.0); 2.323(2.2); 1.250(3.6); 1.232(8.2); 1.213(3.5); 0.008(0.9); 0.000(28.9); −0.008(1.2)

-continued

Example I-16: logP (neutral): 3.17 1H-NMR(400.0 MHz, d6-DMSO): □ =
9.310(4.6); 8.864(6.6); 8.710(3.9); 8.688(5.0); 8.515(5.1); 8.493(4.5); 8.323(3.8); 8.308(1.5); 7.803(3.5); 7.798(1.4); 7.787(1.8); 7.781(6.9); 7.775(1.1); 7.740(0.9); 7.733(6.6); 7.728(1.9); 7.716(1.3); 7.711(3.7); 3.977(16.0); 3.848(1.1); 3.830(3.5); 3.811(3.6); 3.793(1.2); 3.345(291.1); 3.340(207.5); 3.329(264.8); 3.328(285.2); 2.676(1.0); 2.672(1.4); 2.667(1.0); 2.663(0.5); 2.542(0.6); 2.525(3.8); 2.520(6.1); 2.512(79.3); 2.507(163.8); 2.503(217.6); 2.498(158.0); 2.494(76.6); 2.339(0.4); 2.334(1.0); 2.331(4.4); 2.325(1.0); 1.251(3.9); 1.232(8.9); 1.214(3.9); 0.000(6.7)
Example I-17: logP (neutral): 2.06 1H-NMR(400.0 MHz, d6-DMSO): □ =
9.314(3.7); 8.965(2.4); 8.958(2.4); 8.920(7.7); 8.721(3.3); 8.699(4.2); 8.660(1.8); 8.656(1.9); 8.648(1.9); 8.644(1.9); 8.523(4.0); 8.501(3.5); 8.331(3.9); 8.199(1.0); 8.196(1.2); 8.193(1.1); 8.189(1.0); 8.179(1.1); 8.175(1.2); 8.172(1.3); 8.168(1.1); 7.654(1.3); 7.653(1.3); 7.642(1.2); 7.641(1.3); 7.634(1.2); 7.632(1.2); 7.622(1.2); 7.620(1.2); 3.979(16.0); 3.852(0.9); 3.833(3.1); 3.815(3.2); 3.796(0.9); 3.321(215.0); 2.675(0.5); 2.670(0.7); 2.666(0.5); 2.524(1.6); 2.519(2.4); 2.510(40.5); 2.506(86.2); 2.501(116.3); 2.497(84.3); 2.492(40.6); 2.333(0.5); 2.328(0.7); 2.323(0.5); 1.251(3.7); 1.233(8.5); 1.214(3.4); 0.000(4.4)
Example I-18: logP (neutral): 2.73: 1H-NMR(400.0 MHz, d6-DMSO): □ =
9.309(4.6); 8.713(5.2); 8.710(4.5); 8.688(3.8); 8.499(3.8); 8.477(3.2); 8.329(4.8); 7.753(0.9); 7.733(1.9); 7.717(1.0); 7.713(1.0); 7.627(0.4); 7.610(0.9); 7.592(1.3); 7.579(0.8); 7.575(0.7); 7.559(1.4); 7.536(1.6); 7.515(0.7); 7.447(1.2); 7.429(1.9); 7.412(0.9); 3.977(16.0); 3.850(1.1); 3.832(3.5); 3.813(3.6); 3.795(1.2); 3.387(0.3); 3.324(445.6); 2.671(1.2); 2.506(151.2); 2.502(197.0); 2.497(156.1); 2.328(1.2); 2.073(1.4); 1.249(3.9); 1.230(8.4); 1.212(3.7); 0.000(4.5); −0.090(1.4)
Example I-19: logP (neutral): 2.82 1H-NMR(400.0 MHz, d6-DMSO): □ =
9.311(1.8); 8.866(2.8); 8.712(1.1); 8.690(1.4); 8.516(1.4); 8.494(1.2); 8.324(1.9); 7.798(1.6); 7.776(2.2); 7.671(2.2); 7.649(1.6); 3.978(5.9); 3.850(0.5); 3.832(1.4); 3.813(1.4); 3.795(0.6); 3.743(0.4); 3.725(0.6); 3.651(16.0); 2.671(0.3); 2.506(41.8); 2.502(54.1); 2.498(43.2); 1.251(1.4); 1.232(3.0); 1.214(1.4); 0.000(19.7)
Example I-20: logP (neutral): 3.13 1H-NMR(400.0 MHz, d6-DMSO): □ =
9.350(4.2); 9.137(7.5); 8.788(2.7); 8.766(4.4); 8.698(4.4); 8.676(2.9); 8.339(4.5); 8.312(0.4); 7.736(0.7); 7.730(0.6); 7.714(1.3); 7.698(0.7); 7.693(0.8); 7.677(0.4); 7.454(2.2); 7.433(3.7); 7.413(1.8); 4.038(0.4); 4.020(0.7); 4.009(16.0); 3.875(1.0); 3.856(3.4); 3.837(3.4); 3.819(1.0); 3.322(135.3); 3.319(117.3); 2.675(0.6); 2.671(0.8); 2.666(0.6); 2.524(2.0); 2.510(49.1); 2.506(98.0); 2.502(128.9); 2.497(96.7); 2.329(0.8); 2.324(0.6); 2.073(0.7); 1.988(1.6); 1.252(3.7); 1.234(8.2); 1.215(3.6); 1.193(0.4); 1.175(0.8); 1.157(0.4); 0.008(1.0); 0.000(29.7)
Example I-21: logP (neutral): 3.71: 1H-NMR(400.0 MHz, d6-DMSO): □ =
9.326(4.8); 8.875(3.2); 8.853(3.7); 8.572(3.8); 8.550(3.5); 8.349(5.0); 7.946(4.5); 7.924(5.6); 7.735(5.5); 7.713(4.6); 3.991(16.0); 3.894(1.1); 3.876(3.5); 3.857(3.6); 3.839(1.1); 3.332(358.8); 2.671(0.6); 2.506(81.6); 2.502(105.3); 2.498(80.8); 2.329(0.6); 1.265(3.7); 1.247(8.1); 1.228(3.7); 0.000(2.2)
Example I-22: logP (neutral): 3.44 1H-NMR(400.0 MHz, d6-DMSO): □ =
9.310(1.5); 8.782(1.2); 8.760(1.5); 8.559(1.4); 8.537(1.2); 8.332(1.4); 7.627(6.2); 3.965(5.6); 3.842(0.4); 3.823(1.2); 3.805(1.2); 3.786(0.4); 3.349(49.6); 3.339(37.4); 3.332(31.4); 2.525(0.5); 2.512(12.3); 2.508(24.2); 2.503(31.3); 2.499(23.0); 2.494(11.6); 2.072(16.0); 1.246(1.3); 1.227(3.0); 1.209(1.3); 0.000(2.4)
Example I-23: logP (neutral): 4.64 1H-NMR(400.0 MHz, d6-DMSO): □ =
9.346(3.7); 8.820(3.9); 8.813(4.1); 8.699(3.3); 8.677(4.3); 8.512(4.2); 8.490(3.6); 8.345(0.3); 8.338(3.9); 8.336(3.8); 8.313(0.4); 8.104(1.7); 8.099(2.9); 8.095(1.7); 8.017(1.0); 8.014(1.6); 8.010(1.0); 7.999(1.1); 7.995(1.8); 7.992(1.1); 7.576(0.9); 7.556(2.4); 7.537(2.1); 7.525(1.5); 7.522(2.0); 7.517(1.6); 7.505(0.7); 7.500(0.8); 7.497(0.6); 7.315(3.5); 7.308(3.6); 4.432(0.4); 4.095(1.0); 4.007(16.0); 3.857(0.9); 3.839(3.1); 3.820(3.2); 3.802(0.9); 3.321(107.8); 2.680(0.3); 2.675(0.7); 2.671(1.0); 2.666(0.7); 2.524(2.6); 2.519(4.2); 2.511(60.2); 2.506(127.2); 2.502(170.9); 2.497(121.7); 2.493(57.0); 2.337(0.3); 2.333(0.7); 2.328(1.0); 2.324(0.7); 1.260(3.4); 1.241(8.0); 1.223(3.3); 0.146(0.4); 0.008(3.7); 0.000(114.6); −0.009(4.2); −0.150(0.4)
Example I-24: logP (neutral): 2.80 1H-NMR(400.0 MHz, d6-DMSO): □ =
9.348(4.2); 8.840(4.0); 8.833(4.1); 8.728(3.5); 8.706(4.2); 8.701(2.3); 8.689(2.3); 8.686(2.2); 8.697(2.3); 8.446(4.1); 8.424(3.7); 8.341(4.5); 8.314(0.5); 8.139(2.2); 8.135(2.1); 8.118(2.4); 8.115(2.2); 7.545(2.2); 7.534(1.7); 7.525(2.0); 7.513(2.0); 7.184(4.0); 7.177(4.1); 4.018(16.0); 3.859(0.9); 3.841(3.3); 3.822(3.3); 3.804(1.0); 3.316(90.6); 2.675(1.0); 2.671(1.4); 2.666(1.0); 2.524(4.0); 2.510(81.8); 2.506(166.2); 2.501(227.2); 2.497(168.8); 2.493(81.2); 2.333(1.0); 2.328(1.3); 2.324(0.9); 2.073(0.5); 1.260(3.5); 1.241(8.1); 1.223(3.4); 0.146(0.6); 0.008(5.3); 0.000(147.0); −0.008(5.0); −0.150(0.6)
Example I-25: logP (neutral): 5.23 1H-NMR(400.0 MHz, d6-DMSO): □ =
9.360(4.9); 9.136(7.4); 8.724(4.3); 8.702(3.8); 8.512(3.8); 8.490(3.2); 8.340(5.2); 8.313(0.4); 8.172(1.7); 8.167(1.8); 8.154(1.7); 8.149(1.8); 8.040(0.9); 8.035(0.9); 8.029(1.0); 8.023(1.0); 8.019(1.1); 8.013(1.1); 8.007(1.0); 8.002(0.9); 7.671(1.7); 7.649(2.9); 7.626(1.5); 4.020(16.0); 3.885(1.1); 3.867(3.5); 3.848(3.6); 3.830(1.1); 3.320(222.3); 2.671(1.0); 2.506(121.5); 2.502(161.9); 2.498(125.0); 2.329(1.0); 2.073(3.6); 1.264(3.7); 1.245(8.1); 1.227(3.7); 0.146(0.7); 0.000(130.8); −0.150(0.6)
Example I-26: logP (neutral): 2.43 1H-NMR(400.0 MHz, d6-DMSO): □ =
9.668(7.7); 9.367(4.6); 9.283(0.4); 8.818(3.3); 8.796(3.9); 8.772(1.7); 8.762(1.7); 8.461(3.8); 8.440(3.6); 8.351(4.9); 8.318(0.4); 8.312(0.8); 8.237(2.0); 8.218(2.5); 8.035(1.0); 8.031(1.0); 8.016(1.8); 8.012(1.8); 7.997(1.0); 7.992(1.0); 7.570(1.2); 7.558(1.3); 7.551(1.3); 7.539(1.1); 4.140(1.3); 4.087(0.4); 4.042(16.0); 3.908(1.0); 3.890(3.5); 3.871(3.5); 3.852(1.2); 3.315(285.7); 2.670(2.0); 2.505(255.8); 2.501(349.9); 2.497(265.6); 2.328(2.1); 2.073(1.1); 1.276(3.7); 1.257(8.2); 1.239(3.8); −0.001(4.4)
Example I-27: logP (neutral): 2.54 1H-NMR(400.0 MHz, d6-DMSO): □ =
9.696(6.7); 9.368(4.9); 9.347(3.1); 9.342(3.1); 8.821(3.3); 8.799(3.7); 8.749(2.1); 8.746(2.0); 8.737(2.1); 8.734(2.0); 8.510(1.2); 8.506(1.8); 8.491(1.3); 8.486(1.8); 8.460(3.7); 8.438(3.4); 8.350(5.2); 7.635(1.5); 7.622(1.5); 7.615(1.5); 7.603(1.4); 4.035(16.0); 3.904(1.1); 3.885(3.5); 3.867(3.6); 3.849(1.1); 3.319(112.4); 2.671(0.9); 2.506(119.0); 2.502(149.9); 2.498(112.5); 2.328(0.9); 2.073(1.4); 1.273(3.9); 1.254(8.4); 1.236(3.7); 0.146(0.6); 0.007(7.0); 0.000(116.0); −0.150(0.6)
Example I-28: logP (neutral): 3.38 1H-NMR(400.0 MHz, d6-DMSO): □ =
10.198(0.4); 9.323(3.8); 9.058(2.7); 9.052(2.7); 8.565(5.5); 8.538(3.3); 8.517(4.4); 8.363(3.9); 8.341(3.3); 8.314(4.3); 8.312(4.1); 7.953(0.4); 7.882(0.7); 7.878(0.8); 7.862(1.0); 7.860(1.4); 7.842(0.8); 7.839(0.6); 7.552(0.4); 7.536(1.3); 7.531(1.9); 7.527(1.0); 7.513(2.5); 7.511(2.4); 7.505(1.5); 7.500(1.2); 7.496(1.0); 7.428(1.0); 7.421(0.9); 7.414(0.5); 7.407(1.2); 7.402(1.1); 7.393(0.5); 7.390(0.5); 7.386(0.6); 5.755(3.2); 3.956(16.0); 3.818(0.9); 3.800(3.2); 3.781(3.3); 3.763(1.0); 3.319(43.5); 2.891(3.2); 2.732(2.5); 2.676(0.3); 2.672(0.4); 2.525(1.1); 2.520(1.8); 2.512(22.2); 2.507(45.3); 2.502(61.5); 2.498(44.1); 2.493(20.1); 2.329(0.4); 1.246(3.4); 1.227(8.0); 1.209(3.3); 0.008(1.4); 0.000(38.1); −0.009(1.1)
Example I-29: logP (neutral): 3.50: 1H-NMR(400.0 MHz, d6-DMSO): □ =
9.340(9.3); 8.886(0.8); 8.789(11.6); 8.558(2.9); 8.536(3.6); 8.519(5.8); 8.477(0.4); 8.471(0.4); 8.316(5.2); 8.290(2.9); 8.050(12.8); 8.002(2.2); 7.990(2.4); 7.985(1.6); 7.980(2.5); 7.968(2.4); 7.914(0.9); 7.897(0.6); 7.888(5.3); 7.876(5.6); 7.870(3.5); 7.865(6.0); 7.853(5.7); 7.767(0.5); 7.755(0.5); 7.749(0.4); 7.744(0.5); 7.734(0.6); 7.645(1.1); 7.627(2.1); 7.615(1.5); 7.598(1.6); 7.574(1.1); 7.566(1.3); 7.557(1.0); 7.550(1.2); 7.537(0.4); 7.530(0.4); 7.422(2.3); 7.416(1.3); 7.406(6.3); 7.401(5.8); 7.384(10.1); 7.362(4.9); 7.339(1.1); 7.322(0.4); 7.301(0.4); 7.279(0.7); 7.257(0.4); 6.540(0.4); 5.754(3.1); 3.985(0.5); 3.965(16.0); 3.813(1.0); 3.794(3.4); 3.775(3.4); 3.757(1.0); 3.568(1.3); 3.318(38.0); 2.696(0.4); 2.671(1.0); 2.524(2.8); 2.506(126.9); 2.502(171.7); 2.498(130.6); 2.333(0.8); 2.329(1.0); 1.247(3.8); 1.229(8.5); 1.210(3.7); 0.008(1.6); −0.001(41.9)
Example I-30: logP (neutral): 2.73 1H-NMR(400.0 MHz, d6-DMSO): □ =
9.334(4.5); 9.266(2.8); 9.260(2.9); 8.809(3.3); 8.802(3.4); 8.645(2.0); 8.624(7.0); 8.616(2.4); 8.613(2.3); 8.599(4.9); 8.578(2.0); 8.410(1.1); 8.407(1.4); 8.404(1.3); 8.389(1.2); 8.386(1.4); 8.383(1.4); 8.328(4.8); 8.314(0.4); 7.650(1.5); 7.639(1.5); 7.630(1.5); 7.618(1.4); 7.312(3.5); 7.305(3.7); 5.754(6.7); 3.967(16.0); 3.846(1.0); 3.827(3.5); 3.809(3.5); 3.790(1.1); 3.318(66.1); 2.671(0.9); 2.667(0.7); 2.506(109.6); 2.502(146.9); 2.498(115.5); 2.329(0.9); 1.253(3.7); 1.234(8.3); 1.216(3.6); 0.000(33.2)

-continued

Example I-31: logP (neutral): 3.81 1H-NMR(400.0 MHz, d6-DMSO): □ =
10.196(0.7); 9.356(4.0); 9.301(0.5); 9.273(0.4); 9.267(0.4); 8.813(0.4); 8.807(0.4); 8.770(3.6); 8.749(4.2); 8.533(3.9); 8.512(3.4); 8.408(0.4);
8.389(0.4); 8.344(4.2); 8.314(0.9); 8.280(0.5); 8.198(0.3); 8.048(6.6); 8.020(2.0); 8.011(2.5); 8.002(2.5); 7.996(2.3); 7.988(0.3); 7.643(0.4);
7.627(0.5); 7.609(0.3); 7.598(0.3); 7.572(1.1); 7.564(3.4); 7.561(3.3); 7.553(4.9); 7.547(5.3); 7.538(0.6); 7.339(0.4); 7.333(0.4); 5.754(2.6);
4.542(1.7); 3.990(16.0); 3.937(0.4); 3.877(1.1); 3.872(1.2); 3.858(3.3); 3.839(3.4); 3.821(1.0); 3.317(208.5); 2.675(1.5); 2.671(2.1); 2.666(1.5);
2.524(5.3); 2.519(8.2); 2.510(112.3); 2.506(235.3); 2.501(328.1); 2.497(243.9); 2.492(116.8); 2.337(0.7); 2.333(1.4); 2.328(2.0); 2.324(1.5);
1.261(3.7); 1.242(8.5); 1.224(3.7); 0.146(0.7); 0.008(5.8); 0.000(178.0); −0.009(6.4); −0.150(0.7)
Example I-32: logP (neutral): 3.52 1H-NMR(400.0 MHz, d6-DMSO): □ =
9.102(9.2); 8.936(2.3); 8.932(2.4); 8.795(2.5); 8.773(4.7); 8.726(7.0); 8.722(2.8); 8.703(2.7); 7.683(0.7); 7.679(0.7); 7.664(1.4); 7.660(1.5);
7.645(0.8); 7.640(0.8); 7.589(0.4); 7.583(0.6); 7.580(0.7); 7.566(0.7); 7.563(0.9); 7.558(0.6); 7.549(0.6); 7.545(0.5); 7.521(1.0); 7.518(1.1);
7.500(0.7); 7.495(1.2); 7.492(1.1); 7.474(0.6); 7.471(0.6); 7.426(1.0); 7.423(0.9); 7.407(1.5); 7.404(1.4); 7.388(0.7); 7.384(0.7); 5.754(0.6);
4.039(0.6); 4.021(0.6); 3.910(16.0); 3.896(3.3); 3.878(3.2); 3.859(0.9); 3.318(29.5); 2.524(0.6); 2.511(17.0); 2.507(36.1); 2.502(48.5); 2.497(34.5);
2.493(16.1); 1.989(2.5); 1.268(3.3); 1.250(7.7); 1.231(3.4); 1.193(0.7); 1.175(1.4); 1.158(0.7); 0.146(0.3); 0.008(2.7);
0.000(79.3); −0.009(2.7); −0.150(0.3)
Example I-33: logP (neutral): 3.52 1H-NMR(400.0 MHz, d6-DMSO): □ =
8.923(2.5); 8.920(2.7); 8.868(7.6); 8.718(5.7); 8.713(2.9); 8.695(3.9); 8.506(3.8); 8.483(3.3); 7.805(0.4); 7.798(4.0); 7.793(1.4); 7.781(1.6);
7.776(5.8); 7.768(0.7); 7.679(0.7); 7.671(5.7); 7.666(1.7); 7.654(1.4); 7.649(4.1); 7.642(0.4); 5.755(9.6); 3.896(16.0); 3.882(3.3); 3.863(3.3);
3.845(1.0); 3.320(35.8); 2.676(0.4); 2.671(0.5); 2.667(0.4); 2.525(1.3); 2.511(27.8); 2.507(57.7); 2.502(80.1); 2.498(59.9); 2.494(29.1); 2.333(0.3);
2.329(0.5); 2.324(0.3); 1.398(0.5); 1.266(3.5); 1.248(7.8); 1.230(3.6); 0.008(2.5); 0.000(67.3); −0.008(2.4)
Example I-34: logP (neutral): 3.62 1H-NMR(400.0 MHz, d6-DMSO): □ =
9.072(8.5); 8.768(2.6); 8.746(4.7); 8.694(4.6); 8.672(2.8); 8.158(2.6); 8.002(1.7); 7.981(2.1); 7.762(1.4); 7.758(1.5); 7.740(1.2); 7.737(1.2);
7.683(0.7); 7.679(0.8); 7.663(1.4); 7.659(1.6); 7.644(0.8); 7.640(0.9); 7.587(0.4); 7.582(0.6); 7.578(0.7); 7.575(0.6); 7.561(0.9); 7.556(0.6);
7.548(0.6); 7.543(0.5); 7.520(1.0); 7.516(1.1); 7.499(0.7); 7.494(1.2); 7.490(1.2); 7.473(0.6); 7.469(0.6); 7.425(1.0); 7.422(0.9); 7.405(1.5);
7.387(0.7); 7.383(0.7); 5.753(9.3); 3.940(0.9); 3.921(3.2); 3.902(4.4); 3.897(16.0); 3.885(1.2); 3.322(38.9); 2.524(0.6); 2.511(15.6); 2.507(33.1);
2.502(44.5); 2.497(32.0); 2.493(15.3); 1.988(0.6); 1.398(0.4); 1.259(3.5); 1.241(7.8); 1.222(3.3); 1.175(0.3); 0.008(2.3); 0.000(68.7); −0.009(2.6)
Example I-35: logP (neutral): 3.16 1H-NMR(400.0 MHz, d6-DMSO): □ =
9.653(6.9); 9.175(13.7); 9.022(10.3); 8.720(5.8); 8.699(7.3); 8.481(7.0); 8.459(6.1); 8.411(6.8); 7.697(1.4); 7.694(1.6); 7.678(3.0); 7.674(3.3);
7.659(1.7); 7.655(1.8); 7.602(0.6); 7.598(0.6); 7.589(0.7); 7.581(1.5); 7.563(2.0); 7.559(1.4); 7.550(1.2); 7.546(1.2); 7.519(2.3); 7.496(2.6);
7.474(1.3); 7.426(2.1); 7.408(3.4); 7.386(1.5); 4.221(2.0); 4.203(6.6); 4.184(6.7); 4.166(2.0); 3.319(59.0); 2.675(1.4); 2.671(1.9); 2.667(1.5);
2.541(1.3); 2.524(4.7); 2.506(246.0); 2.502(324.7); 2.498(236.9); 2.333(1.4); 2.329(1.9); 1.301(7.3); 1.282(16.0); 1.263(7.2); 1.234(0.4); 0.146(1.0);
0.008(7.9); 0.000(220.7); −0.007(9.4); −0.149(1.1)

The log P values are measured according to EEC Directive 79/831 Annex V.A8 by HPLC (high-performance liquid chromatography) on a reversed-phase column (C 18). Temperature: 55° C.

LC-MS determination in the acidic range is effected at pH 2.7 using 0.1% aqueous formic acid and acetonitrile (contains 0.1% formic acid) as mobile phases; linear gradient from 10% acetonitrile to 95% acetonitrile. Called log P (HCOOH) in the table.

LC-MS determination in the neutral range is effected at pH 7.8 with 0.001 molar aqueous ammonium hydrogencarbonate solution and acetonitrile as mobile phases; linear gradient from 10% acetonitrile to 95% acetonitrile. Called log P (neutral) in the table.

Calibration is carried out using unbranched alkan-2-ones (having 3 to 16 carbon atoms) with known log P values (log P values determined on the basis of the retention times by linear interpolation between two successive alkanones).

The NMR data of selected examples are listed either in conventional form (δ values, multiplet splitting, number of hydrogen atoms) or as NMR peak lists.

In each case, the solvent in which the NMR spectrum was recorded is stated.

NMR Peak List Method

The $^1$H NMR data of selected examples are stated in the form of $^1$H NMR peak lists. For each signal peak, first the δ value in ppm and then the signal intensity in round brackets are listed. The pairs of δ value-signal intensity numbers for different signal peaks are listed with separation from one another by semicolons.

The peak list for one example therefore has the form:
$\delta_1$ (intensity$_1$); $\delta_2$ (intensity$_2$); . . . ; $\delta_i$ (intensity$_i$); . . . ; $\delta_n$ (intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

Calibration of the chemical shift of $^1$H NMR spectra is accomplished using tetramethylsilane and/or the chemical shift of the solvent, particularly in the case of spectra which are measured in DMSO. Therefore, the tetramethylsilane peak may but need not occur in NMR peak lists.

The lists of the $^1$H NMR peaks are similar to the conventional $^1$H-NMR printouts and thus usually contain all peaks listed in a conventional NMR interpretation.

In addition, like conventional $^1$H NMR printouts, they may show solvent signals, signals of stereoisomers of the target compounds which are likewise provided by the invention, and/or peaks of impurities.

In the reporting of compound signals within the delta range of solvents and/or water, our lists of $^1$H NMR peaks show the standard solvent peaks, for example peaks of DMSO in DMSO-D$_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in this case to identify the reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the peak picking in question in conventional $^1$H NMR interpretation.

Further details of $^1$H NMR peak lists can be found in the Research Disclosure Database Number 564025.

APPLICATION EXAMPLES

*Ctenocephalides felis*—In Vitro Contact Tests with Adult Cat Fleas

For the coating of the test tubes, 9 mg of active compound are first dissolved in 1 ml of acetone p.a. and then diluted to the desired concentration with acetone p.a. 250 µl of the solution are distributed homogeneously on the inner walls and the base of a 25 ml test tube by turning and rocking on an orbital shaker (rocking rotation at 30 rpm for 2 h). With 900 ppm active compound solution and internal surface 44.7 $cm^2$, given homogeneous distribution, an area-based dose of 5 $\mu g/cm^2$ is achieved.

After the solvent has evaporated off, the tubes are populated with 5-10 adult cat fleas (*Ctenocephalides felis*), sealed with a perforated plastic lid and incubated in a horizontal position at room temperature and ambient humidity. After 48 h, efficacy is determined. To this end, the test tubes are stood upright and the fleas are knocked to the base of the tube. Fleas which remain motionless at the base or move in an uncoordinated manner are considered to be dead or moribund.

A substance shows good efficacy against *Ctenocephalides felis* if at least 80% efficacy was achieved in this test at an application rate of 5 $\mu g/cm^2$. 100% efficacy means that all the fleas were dead or moribund. 0% efficacy means that no fleas were harmed.

In this test, for example, the following compounds from the preparation examples show an efficacy of 100% at an application rate of 5 $\mu g/cm^2$ (500 g/ha): I-1, I-15, I-18, I-24

*Boophilus microplus*—Injection Test

Solvent: dimethyl sulphoxide

To produce a suitable active compound preparation, 10 mg of active compound are mixed with 0.5 ml of solvent and the concentrate is diluted with solvent to the desired concentration.

1 µl of the active compound solution is injected into the abdomen of 5 engorged adult female cattle ticks (*Boophilus microplus*). The animals are transferred into dishes and kept in a climate-controlled room.

Efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds from the preparation examples show an efficacy of 95% at an application rate of 20 µg/animal: I-3, I-18

In this test, for example, the following compounds from the preparation examples show an efficacy of 90% at an application rate of 20 µg/animal: I-12

In this test, for example, the following compounds from the preparation examples show an efficacy of 80% at an application rate of 20 µg/animal: I-1, I-15, I-19, I-32

*Ctenocephalides felis*—Oral Test

Solvent: dimethyl sulphoxide

To produce a suitable active compound preparation, 10 mg of active compound are mixed with 0.5 ml of dimethyl sulphoxide. Dilution with citrated cattle blood gives the desired concentration.

About 20 unfed adult cat fleas (*Ctenocephalides felis*) are placed into a chamber which is closed at the top and bottom with gauze. A metal cylinder whose bottom end is closed with parafilm is placed onto the chamber. The cylinder contains the blood/active compound preparation, which can be imbibed by the fleas through the parafilm membrane.

After 2 days, the kill in % is determined. 100% means that all of the fleas have been killed; 0% means that none of the fleas have been killed.

In this test, for example, the following compounds from the preparation examples show an efficacy of 100% at an application rate of 100 ppm: I-1, I-3, I-7, I-12, I-15, I-16, I-18, I-19, I-23, I-28, I-29, I-32

In this test, for example, the following compounds from the preparation examples show an efficacy of 95% at an application rate of 100 ppm: I-17

In this test, for example, the following compounds from the preparation examples show an efficacy of 90% at an application rate of 100 ppm: I-6

In this test, for example, the following compounds from the preparation examples show an efficacy of 80% at an application rate of 100 ppm: I-21

*Lucilia cuprina* Test

Solvent: dimethyl sulphoxide

To produce a suitable active compound preparation, 10 mg of active compound are mixed with 0.5 ml of dimethyl sulphoxide, and the concentrate is diluted with water to the desired concentration.

About 20 L1 larvae of the Australian sheep blowfly (*Lucilia cuprina*) are transferred into a test vessel containing minced horsemeat and the active compound preparation of the desired concentration.

After 2 days, the kill in % is determined. 100% means that all the larvae have been killed; 0% means that no larvae have been killed.

In this test, for example, the following compounds from the preparation examples show an efficacy of 100% at an application rate of 100 ppm: I-1, I-2, I-3, I-6, I-7, I-12, I-15, I-16, I-17, I-18, I-19, I-21, I-23, I-24, I-28, I-29, I-30, I-32

*Musca domestica* Test

Solvent: dimethyl sulphoxide

To produce a suitable active compound preparation, 10 mg of active compound are mixed with 0.5 ml of dimethyl sulphoxide, and the concentrate is diluted with water to the desired concentration.

Vessels containing a sponge treated with sugar solution and the active compound preparation of the desired concentration are populated with 10 adult houseflies (*Musca domestica*).

After 2 days, the kill in % is determined. 100% means that all of the flies have been killed; 0% means that none of the flies have been killed.

In this test, for example, the following compounds from the preparation examples show an efficacy of 100% at an application rate of 100 ppm: I-32

In this test, for example, the following compounds from the preparation examples show an efficacy of 90% at an application rate of 100 ppm: I-2, I-3

In this test, for example, the following compounds from the preparation examples show an efficacy of 85% at an application rate of 100 ppm: I-18

In this test, for example, the following compounds from the preparation examples show an efficacy of 80% at an application rate of 100 ppm: I-1, I-16, I-19

*Meloidogyne incognita* Test

Solvent: 125.0 parts by weight of acetone

To produce a suitable preparation of active compound, 1 part by weight of active compound is mixed with the stated amount of solvent and the concentrate is diluted with water to the desired concentration.

Vessels are filled with sand, active compound solution, an egg/larvae suspension of the southern root-knot nematode (*Meloidogyne incognita*) and lettuce seeds. The lettuce seeds germinate and the plants develop. The galls develop on the roots.

After 14 days, the nematicidal efficacy in % is determined by the formation of galls. 100% means that no galls were found; 0% means that the number of galls on the treated plants corresponds to the untreated control.

In this test, for example, the following compounds from the preparation examples show an efficacy of 100% at an application rate of 20 ppm: I-15, I-17, I-33

In this test, for example, the following compounds from the preparation examples show an efficacy of 90% at an application rate of 20 ppm: I-8, I-30

*Myzus persicae*—Spray Test

Solvent: 78 parts by weight of acetone
1.5 parts by weight of dimethylformamide
Emulsifier: alkylaryl polyglycol ether To produce a suitable active compound preparation, 1 part by weight of active compound is dissolved with the stated parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) infested by all stages of the green peach aphid (*Myzus persicae*) are sprayed with an active compound preparation of the desired concentration.

After 5-6 days, the efficacy in % is determined. 100% means that all the aphids have been killed; 0% means that no aphids have been killed.

In this test, for example, the following compounds from the preparation examples show an efficacy of 100% at an application rate of 500 g/ha: I-8, I-30

In this test, for example, the following compounds from the preparation examples show an efficacy of 90% at an application rate of 500 g/ha: I-1, I-3, I-17, I-18, I-26, I-29, I-32, I-33

*Phaedon cochleariae*—Spray Test

Solvent: 78.0 parts by weight of acetone
1.5 parts by weight of dimethylformamide
Emulsifier: alkylaryl polyglycol ether To produce a suitable active compound preparation, 1 part by weight of active compound is dissolved with the stated parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) are sprayed with an active compound preparation of the desired concentration and, after drying, populated with larvae of the mustard beetle (*Phaedon cochleariae*).

After 7 days, the efficacy in % is determined. 100% means that all the beetle larvae have been killed; 0% means that no beetle larvae have been killed.

In this test, for example, the following compounds from the preparation examples show an efficacy of 100% at an application rate of 500 g/ha: I-1, I-2, I-3, I-5, I-6, I-7, I-8, I-9, I-10, I-11, I-12, I-13, I-15, I-16, I-17, I-18, I-19, I-21, I-22, I-23, I-24, I-25, I-26, I-27, I-28, I-29, I-30, I-32, I-33, I-34, I-35

*Spodoptera frugiperda*—Spray Test

Solvent: 78.0 parts by weight of acetone
1.5 parts by weight of dimethylformamide
Emulsifier: alkylaryl polyglycol ether To produce a suitable active compound preparation, 1 part by weight of active compound is dissolved with the stated parts by weight of solvent and made up with water containing an emulsifier concentration of 1000 ppm until the desired concentration is attained. To produce further test concentrations, the preparation is diluted with emulsifier-containing water.

Leaf discs of maize (*Zea mays*) are sprayed with an active compound preparation of the desired concentration and, after drying, populated with caterpillars of the armyworm (*Spodoptera frugiperda*).

After 7 days, the efficacy in % is determined. 100% means that all the caterpillars have been killed; 0% means that no caterpillar has been killed.

In this test, for example, the following compounds from the preparation examples show an efficacy of 100% at an application rate of 500 g/ha: I-1, I-2, I-3, I-4, I-5, I-7, I-8, I-9, I-12, I-15, I-16, I-18, I-19, I-21, I-22, I-23, I-24, I-26, I-27, I-28, I-29, I-30, I-31, I-32, I-33, I-34, I-35

In this test, for example, the following compounds from the preparation examples show an efficacy of 83% at an application rate of 500 g/ha: I-6

*Tetranychus urticae*—Spray Test, OP-Resistant

Solvent: 78.0 parts by weight of acetone
1.5 parts by weight of dimethylformamide
Emulsifier: alkylaryl polyglycol ether To produce a suitable active compound preparation, 1 part by weight of active compound is dissolved with the stated parts by weight of solvent and made up with water containing an emulsifier concentration of 1000 ppm until the desired concentration is attained. To produce further test concentrations, the preparation is diluted with emulsifier-containing water.

Discs of bean leaves (*Phaseolus vulgaris*) infested with all stages of the greenhouse red spider mite (*Tetranychus urticae*) are sprayed with an active compound preparation of the desired concentration.

After 6 days, the efficacy in % is determined. 100% means that all the spider mites have been killed; 0% means that no spider mites have been killed.

In this test, for example, the following compounds from the preparation examples show an efficacy of 100% at an application rate of 500 g/ha: I-1

In this test, for example, the following compounds from the preparation examples show an efficacy of 90% at an application rate of 500 g/ha: I-17, I-33

In this test, for example, the following compounds from the preparation examples show an efficacy of 70% at an application rate of 500 g/ha: I-15

The invention claimed is:
1. A compound of formula (I),

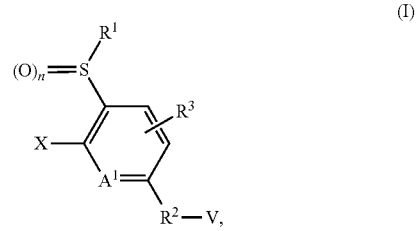

wherein

A¹ represents nitrogen or =C(R⁴)-,

R¹ represents (C₁-C₄)-alkyl, (C₁-C₄)hydroxyalkyl, (C₁-C₄)haloalkyl, (C₂-C₄)alkenyl, (C₂-C₄)haloalkenyl, (C₂-C₄)alkynyl, (C₂-C₄)haloalkynyl, (C₃-C₆)cycloalkyl, (C₁-C₄)alkylthio-(C₁-C₄)alkyl, (C₁-C₄)alkylsulphinyl-(C₁-C₄)alkyl or (C₁-C₄)alkylsulphonyl-(C₁-C₄)alkyl, R²—V represents a 5- or 6-membered ring optionally mono- or disubstituted by identical or different substituents selected from the group consisting of Q-1 to Q-80, where optional substituents are in each case: cyano, halogen, (C₁-C₄)alkyl, (C₁-C₄)haloalkyl, (C₁-C₄)alkoxy or (C₁-C₄)haloalkoxy,

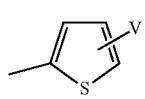

Q-1

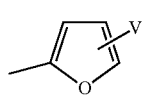

Q-2

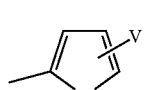

Q-3

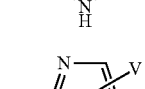

Q-4

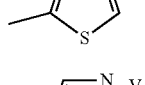

Q-5

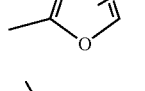

Q-6

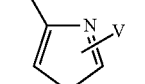

Q-7

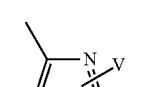

Q-8

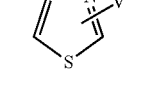

Q-9

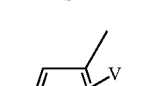

Q-10

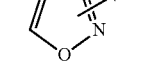

Q-11

-continued

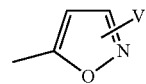

Q-12

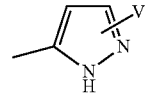

Q-13

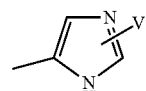

Q-14

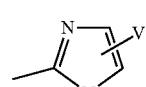

Q-15

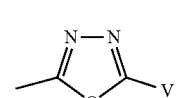

Q-16

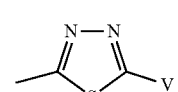

Q-17

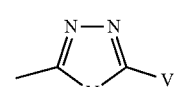

Q-18

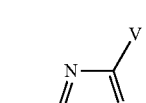

Q-19

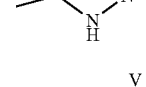

Q-20

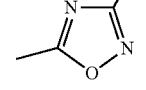

Q-21

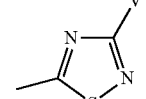

Q-22

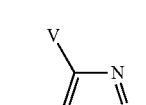

Q-23

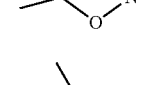

Q-24

| | | | |
|---|---|---|---|
| Q-25 | 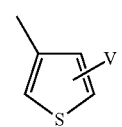 | Q-37 | 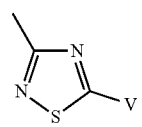 |
| Q-26 | 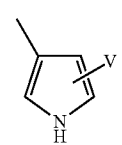 | Q-38 | 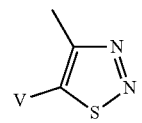 |
| Q-27 | 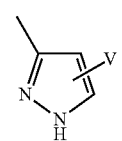 | Q-39 | 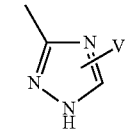 |
| Q-28 | 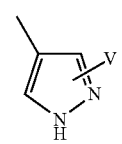 | Q-40 | 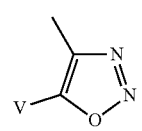 |
| Q-29 | 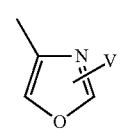 | Q-41 | 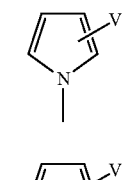 |
| Q-30 | 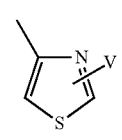 | Q-42 | 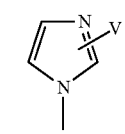 |
| Q-31 | 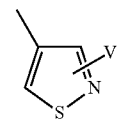 | Q-43 | 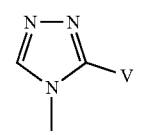 |
| Q-32 | 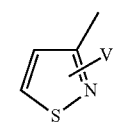 | Q-44 | 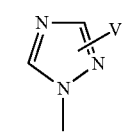 |
| Q-33 | 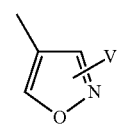 | Q-45 | 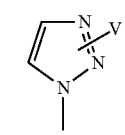 |
| Q-34 | 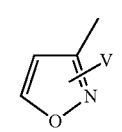 | Q-46 | 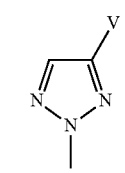 |
| Q-35 | 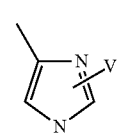 | Q-47 | |
| Q-36 | 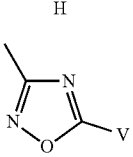 | | |

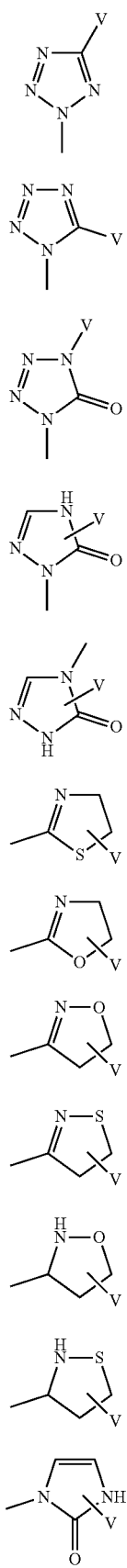
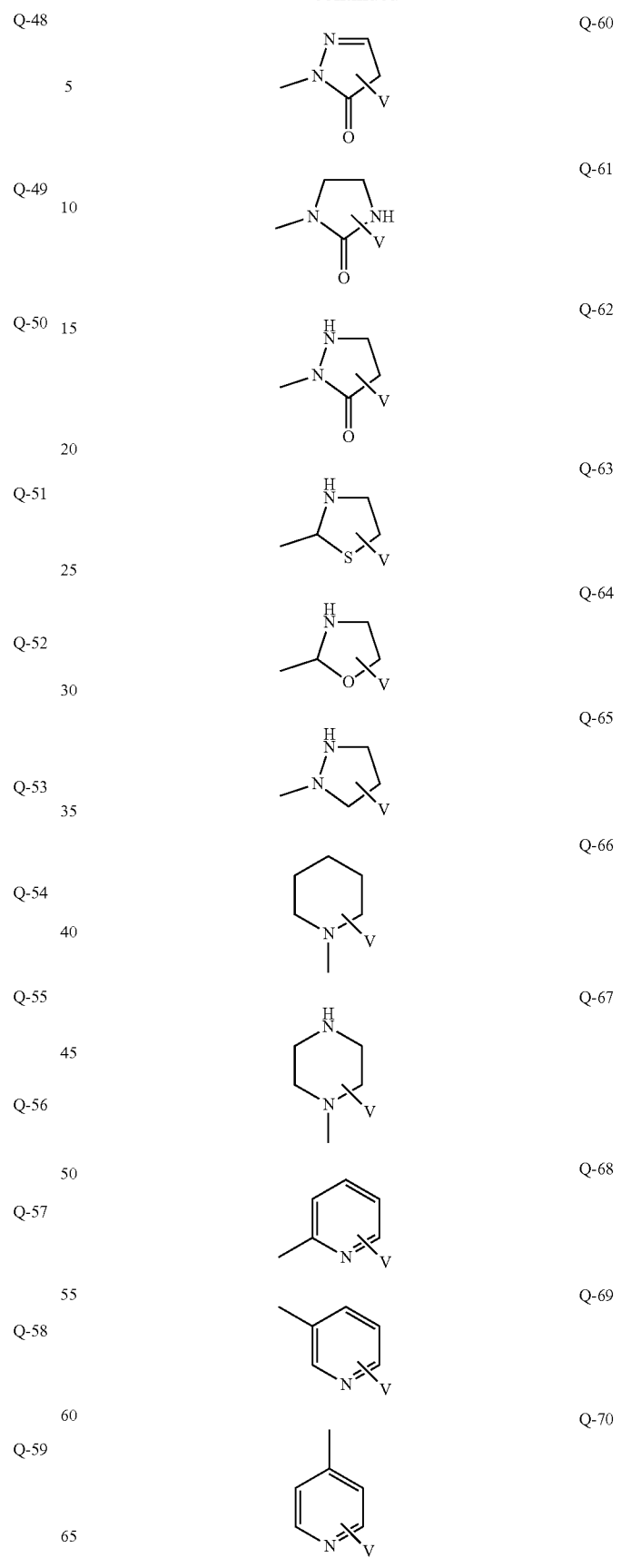

-continued
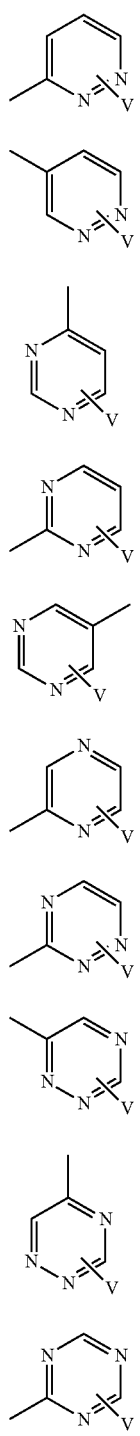
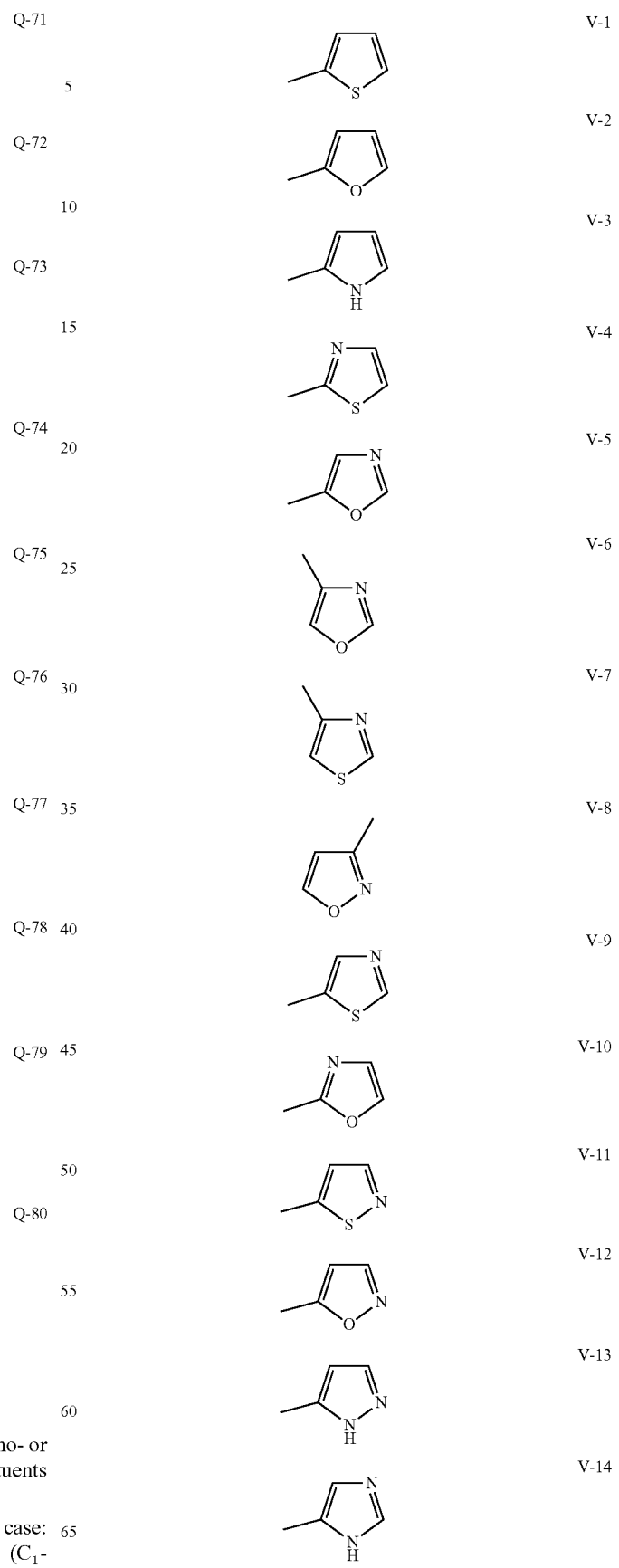
where
V represents a 5- or 6-membered ring optionally mono- or disubstituted by identical or different substituents selected from the group consisting of
V-1 to V-101, where optional substituents are in each case: cyano, halogen, $(C_1-C_4)$alkyl, $(C_1-C_4)$haloalkyl, $(C_1-C_4)$alkoxy or $(C_1-C_4)$haloalkoxy,

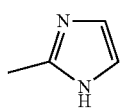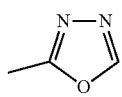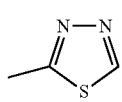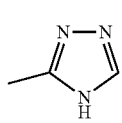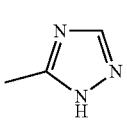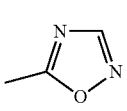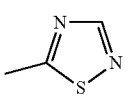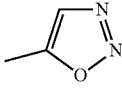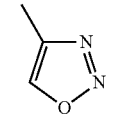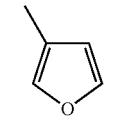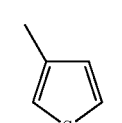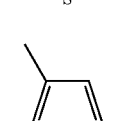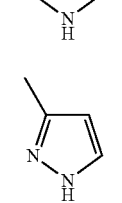
V-15
V-16
V-17
V-18
V-19
V-20
V-21
V-22
V-23
V-24
V-25
V-26
V-27
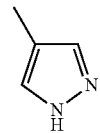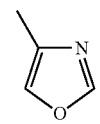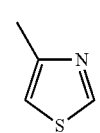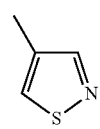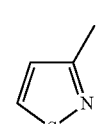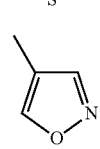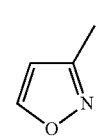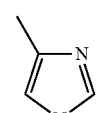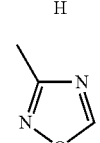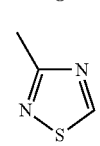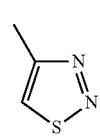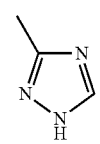
V-28
V-29
V-30
V-31
V-32
V-33
V-34
V-35
V-36
V-37
V-38
V-39

V-40 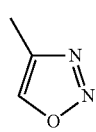
V-41 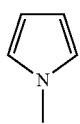
V-42 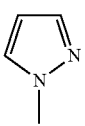
V-43 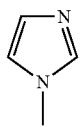
V-44 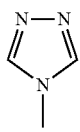
V-45 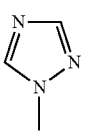
V-46 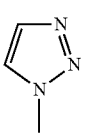
V-47 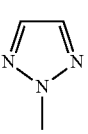
V-48 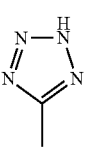
V-49 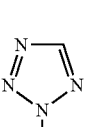
V-50 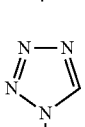
V-51 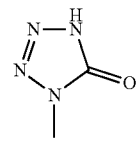
V-52 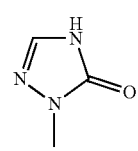
V-53 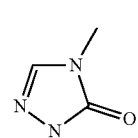
V-54 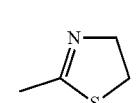
V-55 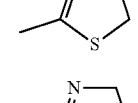
V-56 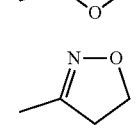
V-57 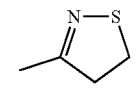
V-58 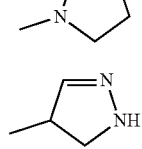
V-59 
V-60 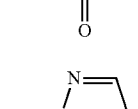
V-61 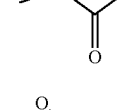
V-62 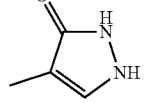
V-63 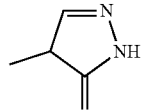

-continued
| | | | |
|---|---|---|---|
| V-64 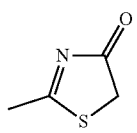 | | V-76 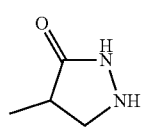 | |
| V-65 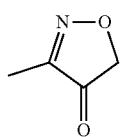 | | V-77 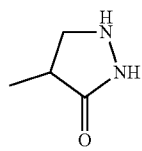 | |
| V-66 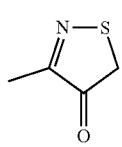 | | V-78 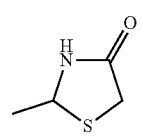 | |
| V-67 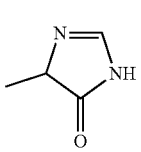 | | V-79 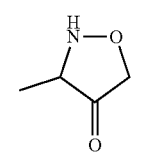 | |
| V-68 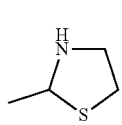 | | V-80 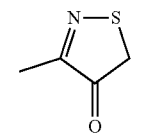 | |
| V-69 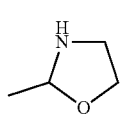 | | V-81 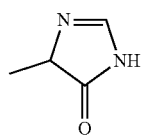 | |
| V-70 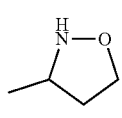 | | V-82 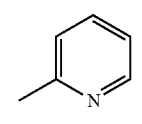 | |
| V-71 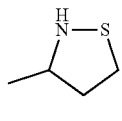 | | V-83 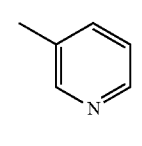 | |
| V-72 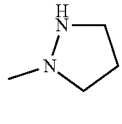 | | V-84 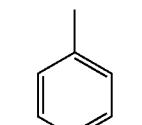 | |
| V-73 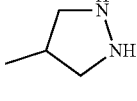 | | V-85 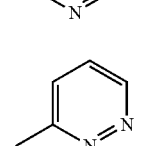 | |
| V-74 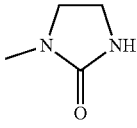 | | V-86 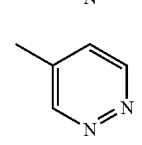 | |
| V-75 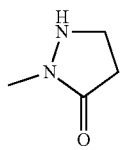 | | | |

| V-87 | 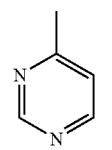 | V-99 | 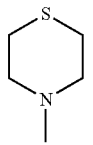 |
| V-88 | 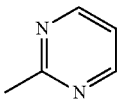 | V-100 | 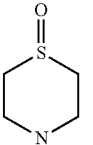 |
| V-89 | 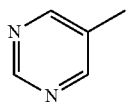 | V-101 | 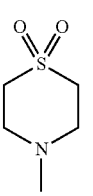 |
| V-90 | 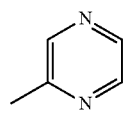 | | |
| V-91 | 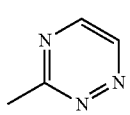 | | |
| V-92 | 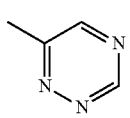 | | |
| V-93 | 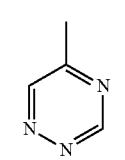 | | |
| V-94 | 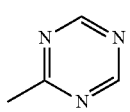 | | |
| V-95 | 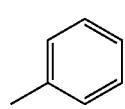 | | |
| V-96 | 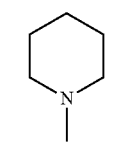 | | |
| V-97 | 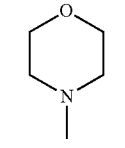 | | |
| V-98 | 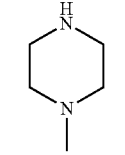 | | |

$R^3$ represents hydrogen, cyano, halogen, nitro, hydroxy, amino, SCN, tri-$(C_1-C_4)$alkylsilyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo$(C_3-C_6)$cycloalkyl, $(C_1-C_4)$alkyl, $(C_1-C_4)$haloalkyl, $(C_1-C_4)$cyanoalkyl, $(C_1-C_4)$alkoxy-$(C_1-C_4)$alkyl, $(C_2-C_4)$alkenyl, $(C_2-C_4)$haloalkenyl, $(C_2-C_4)$cyanoalkenyl, $(C_2-C_4)$alkynyl, $(C_2-C_4)$haloalkynyl, $(C_2-C_4)$cyanoalkynyl, $(C_1-C_4)$alkoxy, $(C_1-C_4)$haloalkoxy, $(C_1-C_4)$cyanoalkoxy, $(C_1-C_4)$alkylhydroxyimino, $(C_1-C_4)$alkoxyimino, $(C_1-C_4)$alkyl-$(C_1-C_4)$alkoxyimino, $(C_1-C_4)$alkylthio, $(C_1-C_4)$haloalkylthio, $(C_1-C_4)$alkylsulphinyl, $(C_1-C_4)$haloalkylsulphinyl, $(C_1-C_4)$alkylsulphonyl, $(C_1-C_4)$haloalkylsulphonyl, $(C_1-C_4)$alkylsulphonyloxy, $(C_1-C_4)$alkylcarbonyl, $(C_1-C_4)$haloalkylcarbonyl, aminocarbonyl, $(C_1-C_4)$alkylaminocarbonyl, di-$(C_1-C_4)$alkylaminocarbonyl, $(C_1-C_4)$alkylsulphonylamino, $(C_1-C_4)$alkylamino, di-$(C_1-C_4)$alkylamino, aminosulphonyl, $(C_1-C_4)$alkylaminosulphonyl, di-$(C_1-C_4)$alkylaminosulphonyl or NHCO—$(C_1-C_4)$alkyl ($(C_1-C_4)$alkylcarbonylamino), $R^4$ represents hydrogen, halogen, cyano or $(C_1-C_4)$alkyl, X represents a heteroaromatic 9-membered or 12-membered fused bicyclic or tricyclic ring system selected from the group consisting of H1 to H20,

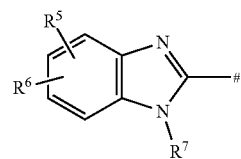 H1

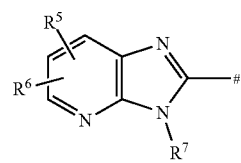 H2

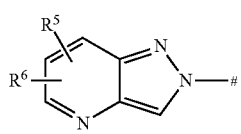 H3

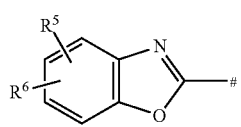 H4

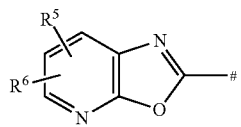 H5

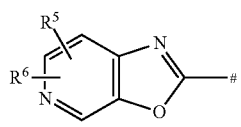 H6

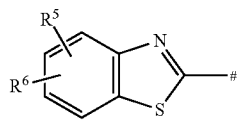 H7

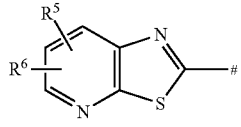 H8

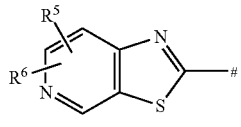 H9

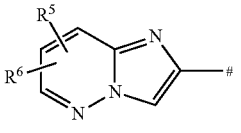 H10

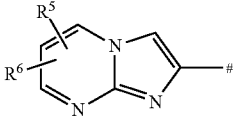 H11

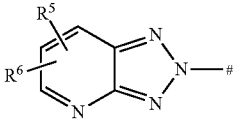 H12

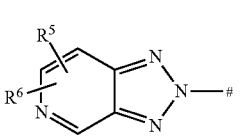 H13

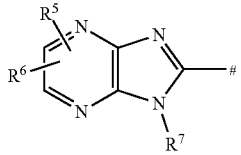 H14

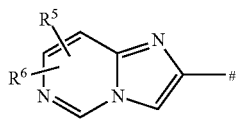 H15

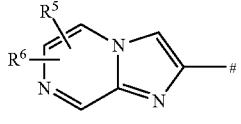 H16

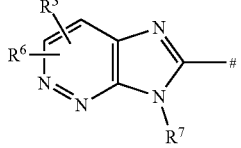 H17

H18

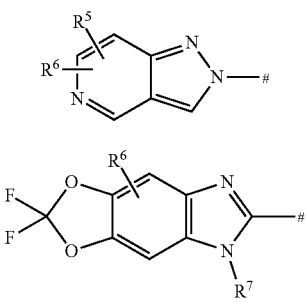 H19

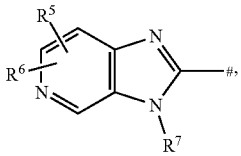 H20

$R^5$, $R^6$ independently of one another represent hydrogen, cyano, halogen, $(C_1-C_4)$alkyl, $(C_1-C_4)$haloalkyl, $(C_2-C_4)$alkenyl, $(C_2-C_4)$haloalkenyl, $(C_2-C_4)$alkynyl, $(C_2-C_4)$haloalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, $(C_1-C_4)$alkoxy, $(C_1-C_4)$haloalkoxy, $(C_1-C_4)$alkoxyimino, $(C_1-C_4)$alkylthio, $(C_1-C_4)$haloalkylthio, $(C_1-C_4)$alkylsulphinyl, $(C_1-C_4)$haloalkylsulphinyl, $(C_1-C_4)$alkylsulphonyl, $(C_1-C_4)$haloalkylsulphonyl, $(C_1-C_4)$alkylsulphonyloxy, $(C_1-C_4)$alkylcarbonyl, $(C_1-C_4)$haloalkylcarbonyl, aminocarbonyl, $(C_1-C_4)$alkylaminocarbonyl, di-$(C_1-C_4)$alkylaminocarbonyl, $(C_1-C_4)$alkylsulphonylamino, $(C_1-C_4)$alkylamino, di-$(C_1-C_4)$alkylamino, aminosulphonyl, $(C_1-C_4)$alkylaminosulphonyl or di-$(C_1-C_4)$alkylaminosulphonyl, $R^7$ represents $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_1-C_4)$haloalkoxy-$(C_1-C_4)$alkyl, $(C_2-C_4)$alkenyl, $(C_2-C_4)$alkenyloxy-$(C_1-C_4)$alkyl, $(C_2-C_4)$haloalkenyloxy-$(C_1-C_4)$alkyl, $(C_2-C_4)$haloalkenyl, $(C_2-C_4)$cyanoalkenyl, $(C_2-C_4)$alkynyl, $(C_2-C_4)$alkynyloxy-$(C_1-C_4)$alkyl, $(C_2-C_4)$haloalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo$(C_3-C_6)$cycloalkyl, $(C_1-C_4)$alkylthio-$(C_1-C_4)$alkyl, $(C_1-C_4)$alkylsulphinyl-$(C_1-C_4)$alkyl, $(C_1-C_4)$alkylsulphonyl-$(C_1-C_4)$alkyl or $(C_1-C_4)$alkylcarbonyl-$(C_1-C_4)$alkyl, n represents 0, 1 or 2.

2. The compound of formula (I) according to claim 1 wherein $A^1$ represents nitrogen or =C($R^4$)-, $R^1$ represents methyl, ethyl, n-propyl, isopropyl, cyclopropyl, n-butyl, isobutyl, tert-butyl, cyclobutyl, fluoromethyl, difluoromethyl, trifluoromethyl, fluoroethyl, difluoroethyl, trifluoroethyl, tetrafluoroethyl or pentafluoroethyl, $R^2$—V represents an optionally monosubstituted 5- or 6-membered ring selected from the group consisting of Q-1, Q-2, Q-3, Q-4, Q-5, Q-6, Q-7, Q-8, Q-9, Q-10, Q-12, Q-13, Q-14, Q-15, Q-16, Q-17, Q-24, Q-25, Q-26, Q-27, Q-28, Q-29, Q-30, Q-34, Q-35, Q-41, Q-42, Q-43, Q-44, Q-45, Q-46, Q-47, Q-48, Q-49, Q-50, Q-51, Q-52, Q-55, Q-59, Q-61, Q-66, Q-67, Q-68, Q-69, Q-70, Q-71, Q-72, Q-73, Q-74 and Q-75,

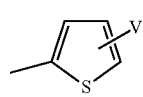
Q-1

Q-2

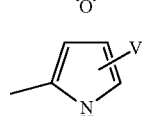
Q-3

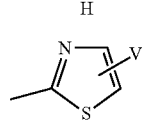
Q-4

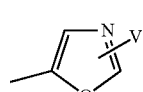
Q-5

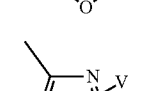
Q-6

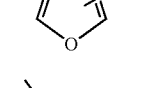
Q-7

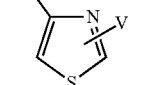
Q-8

Q-9

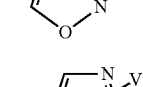

-continued

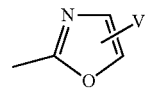
Q-10

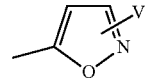
Q-12

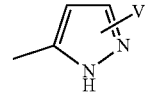
Q-13

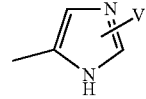
Q-14

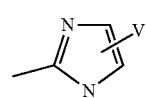
Q-15

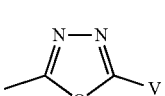
Q-16

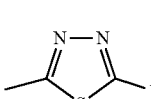
Q-17

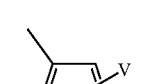
Q-24

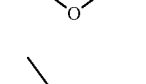
Q-25

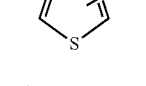
Q-26

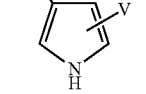
Q-27

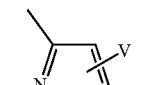
Q-28

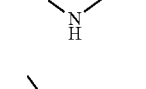
Q-29

-continued
Q-30 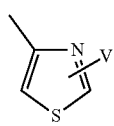
Q-34 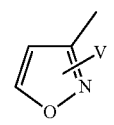
Q-35 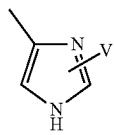
Q-41 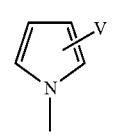
Q-42 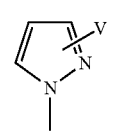
Q-43 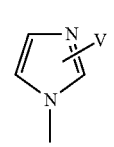
Q-44 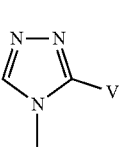
Q-45 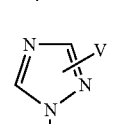
Q-46 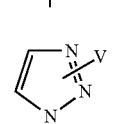
Q-47 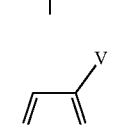
Q-48 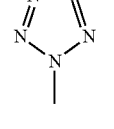
-continued
Q-49 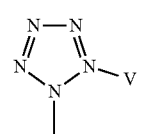
Q-50 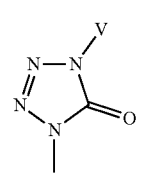
Q-51 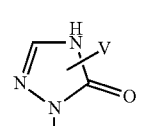
Q-52 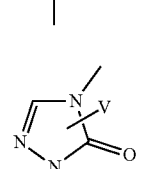
Q-55 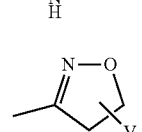
Q-59 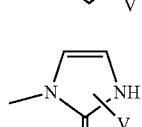
Q-61 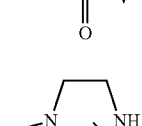
Q-66 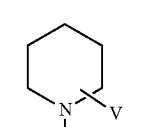
Q-67 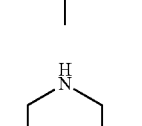
Q-68 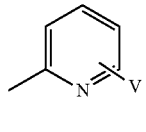
Q-69 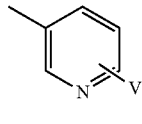

-continued

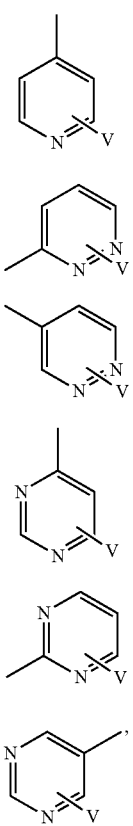

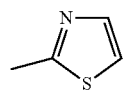

where optional substituents are in each case: cyano, fluorine, chlorine, methyl, ethyl, n-propyl, isopropyl, n-butyl, isobutyl, tert-butyl, trifluoromethyl, methoxy or trifluoromethoxy, where V represents a ring optionally mono- or disubstituted by identical or different substituents selected from cyano, fluorine, chlorine, bromine, methyl, ethyl, n-propyl, isopropyl, n-butyl, isobutyl, tert-butyl, trifluoromethyl, methoxy or trifluoromethoxy, or is selected from the group consisting of V-1, V-2, V-3, V-4, V-5, V-6, V-7, V-9, V-10, V-16, V-17, V-18, V-19, V-20, V-21, V-24, V-25, V-27, V-28, V-29, V-30, V-35, V-36, V-39, V-42, V-43, V-44, V-45, V-46, V-47, V-48, V-49, V-50, V-51, V-52, V-53, V-60, V-82, V-83, V-84, V-85, V-86, V-87, V-88, V-89, V-90, V-91, V-92, V-93, V-94, V-95, V-96, V-97, V-98, V-99, V-100 and V-101, -continued
V-27 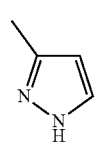
V-28 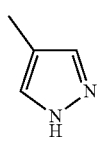
V-29 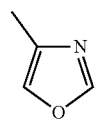
V-30 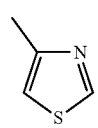
V-35 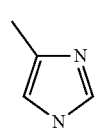
V-36 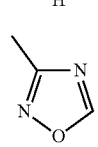
V-39 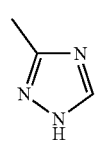
V-42 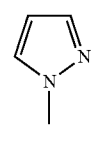
V-43 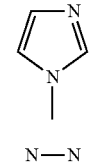
V-44 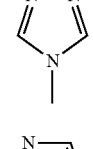
V-45 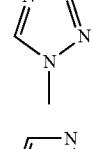
V-46 
-continued
V-47 
V-48 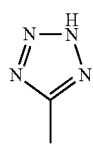
V-49 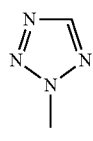
V-50 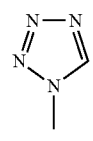
V-51 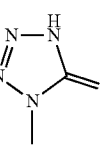
V-52 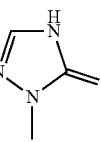
V-53 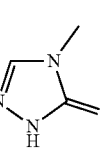
V-60 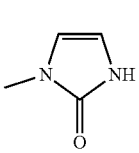
V-82 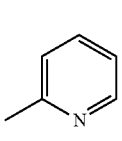
V-83 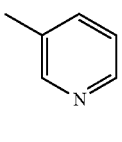
V-84 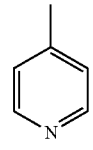

V-85 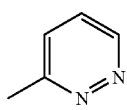

V-86 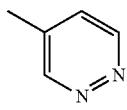

V-87 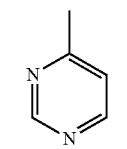

V-88 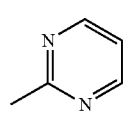

V-89 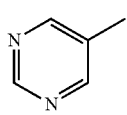

V-90 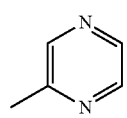

V-91 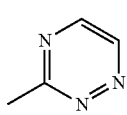

V-92 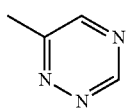

V-93 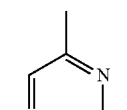

V-94 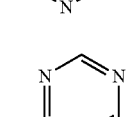

V-95 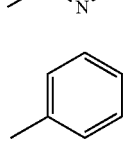

V-96 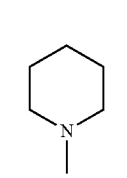

V-97 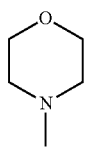

V-98 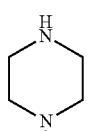

V-99 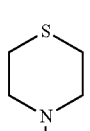

V-100 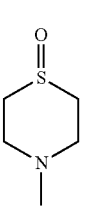

V-101 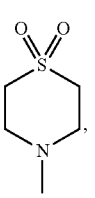

$R^3$ represents hydrogen, cyano, halogen, $(C_1-C_4)$alkyl, $(C_1-C_4)$haloalkyl, $(C_1-C_4)$haloalkoxy, $(C_1-C_4)$alkylthio, $(C_1-C_4)$alkylsulphinyl, $(C_1-C_4)$alkylsulphonyl, $(C_1-C_4)$haloalkylthio, $(C_1-C_4)$haloalkylsulphinyl, $(C_1-C_4)$haloalkylsulphonyl or NHCO—$(C_1-C_4)$alkyl $((C_1-C_4)$alkylcarbonylamino), X represents a heteroaromatic 9-membered or 12-membered fused bicyclic or tricyclic ring system selected from the group consisting of H1, H2, H3, H4, H5, H6, H7, H8, H9, H10, H11, H12, H13, H14, H15, H16, H17, H18, H19, and H20, H1 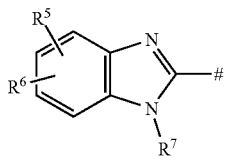

H2 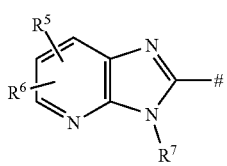

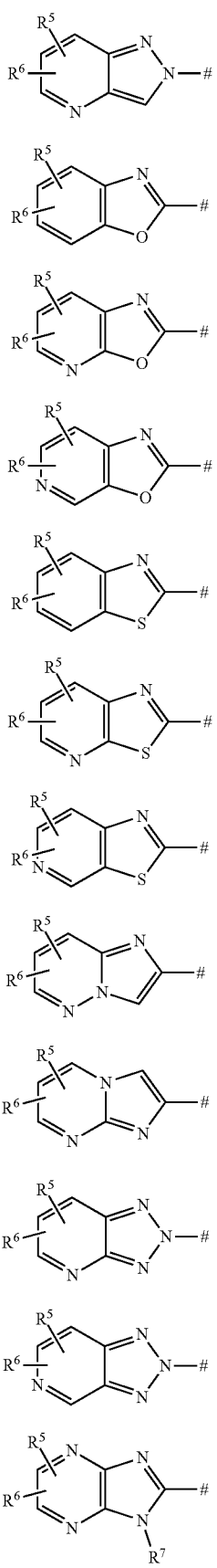

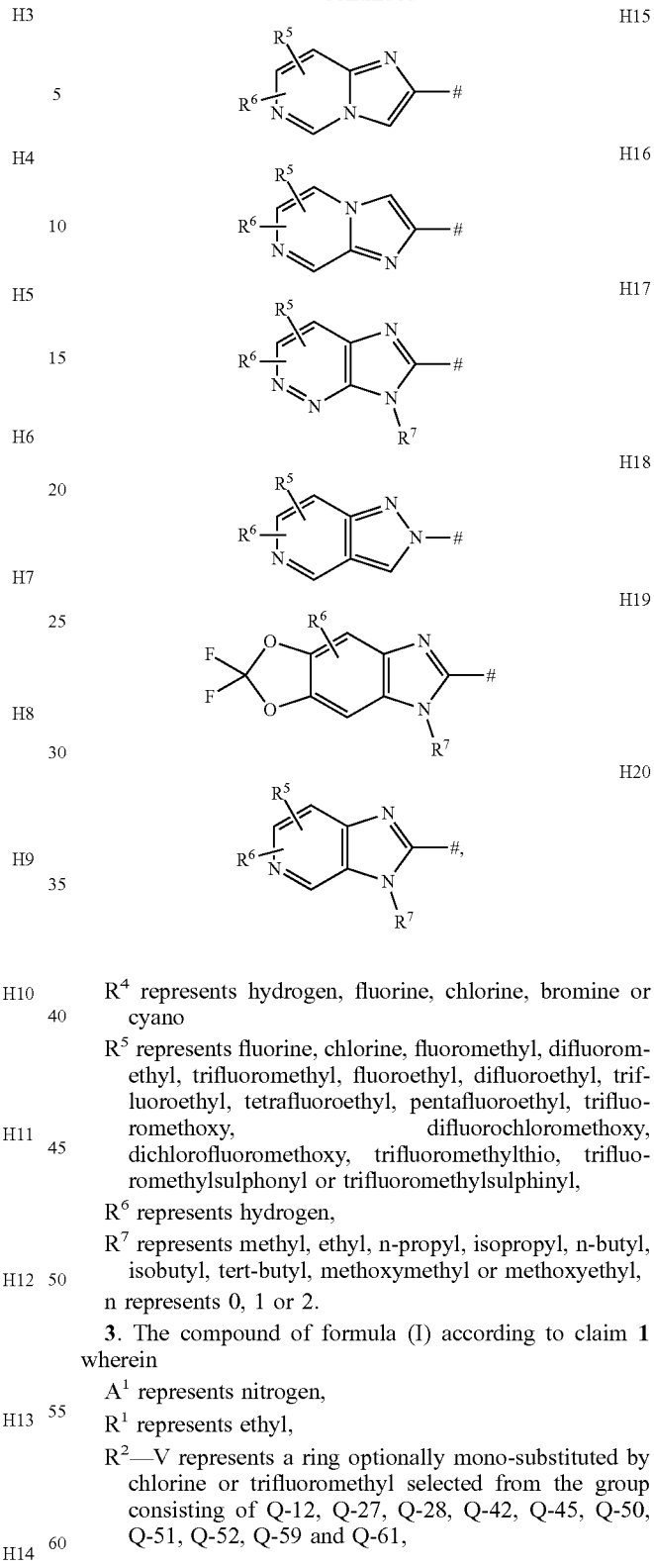

R[4] represents hydrogen, fluorine, chlorine, bromine or cyano

R[5] represents fluorine, chlorine, fluoromethyl, difluoromethyl, trifluoromethyl, fluoroethyl, difluoroethyl, trifluoroethyl, tetrafluoroethyl, pentafluoroethyl, trifluoromethoxy, difluorochloromethoxy, dichlorofluoromethoxy, trifluoromethylthio, trifluoromethylsulphonyl or trifluoromethylsulphinyl, R[6] represents hydrogen, R[7] represents methyl, ethyl, n-propyl, isopropyl, n-butyl, isobutyl, tert-butyl, methoxymethyl or methoxyethyl, n represents 0, 1 or 2.

3. The compound of formula (I) according to claim 1 wherein

A[1] represents nitrogen,

R[1] represents ethyl,

R[2]—V represents a ring optionally mono-substituted by chlorine or trifluoromethyl selected from the group consisting of Q-12, Q-27, Q-28, Q-42, Q-45, Q-50, Q-51, Q-52, Q-59 and Q-61,

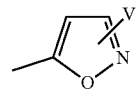

-continued

Q-27, Q-28, Q-42, Q-45, Q-50, Q-51, Q-52, Q-59, Q-61

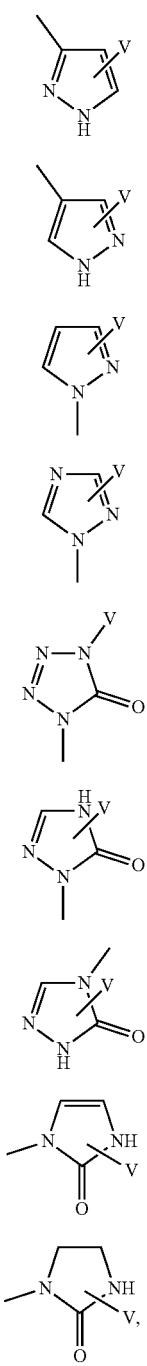

where
V represents a ring optionally mono- or disubstituted by identical or different substituents selected from fluorine, chlorine or bromine, selected from the group consisting of V-2, V-82, V-83 and V-95,

V-2

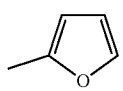

-continued

V-82, V-83, V-95

R³ represents hydrogen,
X represents a heteroaromatic ring system selected from the group consisting of H1, H2, H15 and H20,

H1, H2, H15, H20

$R^5$ represents trifluoromethyl,
$R^6$ represents hydrogen,
$R^7$ represents methyl,
n represents 2.

4. A product comprising the compound of formula (I) according to claim 1 or agrochemical formulation thereof for controlling one or more animal pests.

5. The compound of formula (I) according to claim 3, wherein
$R^2$—V represents Q-51,
V represents V-95 and is monosubstituted by chlorine, and
X represents H20.

6. The compound of formula (I) according to claim 1 wherein
$A^1$ represents nitrogen,
$R^2$—V represents Q51, optionally substituted by cyano, halogen, $(C_1\text{-}C_4)$alkyl, $(C_1\text{-}C_4)$haloalkyl, $(C_1\text{-}C_4)$alkoxy or $(C_1\text{-}C_4)$haloalkoxy, V represents V-95, optionally substituted by cyano, halogen, $(C_1-C_4)$alkyl, $(C_1-C_4)$haloalkyl, $(C_1-C_4)$alkoxy or $(C_1-C_4)$haloalkoxy, and X represents H20.

7. The compound of formula (I) according to claim 6, wherein V is monosubstituted by chlorine.

8. The compound of formula (I) according to claim 1, wherein $A^1$ represents nitrogen.

9. The compound of formula (I) according to claim 1, wherein $A^1$ represents $=N^+(O^-)-$.

10. The compound of formula (I) according to claim 1, wherein $A^1$ represents $=C(R^4)-$.

11. An agrochemical formulation comprising one or more compounds of the formula (I) according to claim 1 and also one or more extenders and/or surfactants.

12. The agrochemical formulation according to claim 11, additionally comprising a further agrochemically active compound.

13. A method for controlling one or more animal pests, comprising allowing a compound of the formula (I) according to claim 1 or an agrochemical formulation thereof to act on the animal pests and/or a habitat thereof.

* * * * *